US012459989B2

(12) United States Patent
Barouch et al.

(10) Patent No.: US 12,459,989 B2
(45) Date of Patent: Nov. 4, 2025

(54) ANTIBODY THERAPIES FOR HUMAN IMMUNODEFICIENCY VIRUS (HIV)

(71) Applicant: Beth Israel Deaconess Medical Center, Inc., Boston, MA (US)

(72) Inventors: Dan H. Barouch, Newton, MA (US); Bruce A. Kerwin, Bainbridge Island, WA (US); Randal R. Ketchem, Snohomish, WA (US); Alison J. Gillespie, Seattle, WA (US); Christine C. Siska, Seattle, WA (US); Rutilio H. Clark, Bainbridge Island, WA (US); Julee A. Floyd, Seattle, WA (US); Jeremy M. Shaver, Lake Forest Park, WA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1015 days.

(21) Appl. No.: 17/295,798

(22) PCT Filed: Nov. 19, 2019

(86) PCT No.: PCT/US2019/062203

§ 371 (c)(1),
(2) Date: May 20, 2021

(87) PCT Pub. No.: WO2020/106713

PCT Pub. Date: May 28, 2020

(65) Prior Publication Data

US 2022/0025021 A1 Jan. 27, 2022

Related U.S. Application Data

(60) Provisional application No. 62/770,541, filed on Nov. 21, 2018.

(51) Int. Cl.
*A61K 45/06* (2006.01)
*C07K 16/10* (2006.01)

(52) U.S. Cl.
CPC .......... *C07K 16/1045* (2013.01); *A61K 45/06* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,500,362 | A | 3/1996 | Robinson et al. | |
| 5,821,337 | A | 10/1998 | Carter et al. | |
| 6,737,056 | B1 | 5/2004 | Presta | |
| 9,017,691 | B2 | 4/2015 | Barouch et al. | |
| 9,464,131 | B2 | 10/2016 | Chan-Hui et al. | |
| 10,040,863 | B2 | 8/2018 | Uda et al. | |
| 10,087,239 | B2 * | 10/2018 | Chan-Hui | C07K 16/1063 |
| 10,093,720 | B2 | 10/2018 | Burton et al. | |
| 10,376,583 | B2 | 8/2019 | Barouch | |
| 2005/0130125 | A1 | 6/2005 | Zagyansky | |
| 2007/0298051 | A1 | 12/2007 | Barouch et al. | |
| 2009/0215639 | A1 | 8/2009 | Crea et al. | |
| 2009/0263382 | A1 | 10/2009 | Ewert et al. | |
| 2011/0295365 | A1 | 12/2011 | Hyde et al. | |
| 2012/0288502 | A1 | 11/2012 | Diskin et al. | |
| 2013/0071406 | A1 | 3/2013 | Goldenberg et al. | |
| 2013/0251726 | A1 | 9/2013 | Mascola et al. | |
| 2014/0302080 | A1 | 10/2014 | Barouch et al. | |
| 2014/0348791 | A1 | 11/2014 | Barouch et al. | |
| 2015/0291935 | A1 | 10/2015 | Barouch et al. | |
| 2016/0008374 | A1 | 1/2016 | Geleziunas et al. | |
| 2016/0213779 | A1 | 7/2016 | Barouch | |
| 2016/0264649 | A1 * | 9/2016 | Chan-Hui | A61K 39/21 |
| 2017/0190763 | A1 | 7/2017 | Balakrishnan et al. | |
| 2020/0129618 | A1 | 4/2020 | Barouch | |
| 2021/0206838 | A1 | 7/2021 | Barouch et al. | |

FOREIGN PATENT DOCUMENTS

| | | | |
|---|---|---|---|
| EP | 3052132 | A2 | 8/2016 |
| WO | WO-03/008332 | A1 | 1/2003 |
| WO | WO-2004/0044155 | A2 | 5/2004 |
| WO | WO-2007/104792 | A2 | 9/2007 |
| WO | WO-2012/030904 | A2 | 3/2012 |
| WO | WO-2014/047261 | A1 | 3/2014 |
| WO | WO-2015/048770 | A2 | 4/2015 |
| WO | WO-2015/051270 | A1 | 4/2015 |
| WO | WO-2016/014484 | A1 | 1/2016 |

(Continued)

OTHER PUBLICATIONS

Klein, et al. Nature. Dec. 6, 2012;492(7427):118-22. doi: 10.1038/nature11604. Epub Oct. 24, 2012. PMID: 23103874. (Year: 2012).*
Rudicell, et al. J Virol. Nov. 2014;88(21):12669-82. doi: 10.1128/JVI.02213-14. Epub Aug. 20, 2014. PMID: 2514260. (Year: 2014).*
Althaus et al., "Dynamics of immune escape during HIV/SIV infection," PLoS Comput Biol. 4(7):e1000103 (2008) (9 pages).
Andrade et al., "Three distinct phases of HIV-1 RNA decay in treatment-naive patients receiving raltegravir-based antiretroviral therapy: ACTG A5248," J Infect Dis. 208(6):884-91 (2013).
Appendix: Chain Variable Region Alignments to Response to Office Action for U.S. Appl. No. 15/025,961, dated Apr. 2, 2018 (3 Pages).
Bansal, "A summary of the workshop on passive immunization using monoclonal antibodies for HIV/AIDS, held at the National Institute of Allergy and Infectious Diseases, Bethesda, Mar. 10, 2006," Biologicals. 35(4):367-71 (2007).

(Continued)

*Primary Examiner* — Janet L Andres
*Assistant Examiner* — Jeffrey Mark Sifford
(74) *Attorney, Agent, or Firm* — Clark & Elbing LLP

(57) ABSTRACT

Featured are PGDM1400 variant antibodies or fragments thereof, which can be administered, e.g., as antibody therapies for treating human immunodeficiency virus (HIV) infection. In particular, featured are methods of treating or curing subjects infected with HIV and/or preventing HIV infections in subjects at risk of HIV transmission using the PGDM1400 variant antibodies or fragments thereof.

20 Claims, 6 Drawing Sheets

Specification includes a Sequence Listing.

(56) References Cited

FOREIGN PATENT DOCUMENTS

| | | | | |
|---|---|---|---|---|
| WO | WO-2016/149698 | A2 | 9/2016 | |
| WO | WO-2016/196740 | A1 | 12/2016 | |
| WO | WO-2017074878 | A1 * | 5/2017 | ............. A61K 39/42 |
| WO | WO-2017/096221 | A1 | 6/2017 | |
| WO | WO-2017/106346 | A2 | 6/2017 | |
| WO | WO-2019/226829 | A1 | 11/2019 | |
| WO | WO-2020/106713 | A1 | 5/2020 | |

OTHER PUBLICATIONS

Barnes et al., "Structural characterization of a highly-potent V3-glycan broadly neutralizing antibody bound to natively-glycosylated HIV-1 envelope," Nat Commun. 9(1):1251 (2018) (12 pages).

Barouch et al., "Immunologic strategies for HIV-1 remission and eradication," Science. 345(6193): 169-174 (2014).

Barouch et al., "Protective efficacy of a global HIV-1 mosaic vaccine against heterologous SHIV challenges in rhesus monkeys," available in PMC Oct. 24, 2014, published in final edited form as: Cell. 155(3):531-9 (2013) (16 pages).

Barouch et al., "Therapeutic efficacy of potent neutralizing HIV-1-specific monoclonal antibodies in SHIV-infected rhesus monkeys," Nature. 503(7475):224-228 (2013) (13 pages).

Barouch et al., "Vaccine protection against acquisition of neutralization-resistant SIV challenges in rhesus monkeys," available in PMC Aug. 2, 2012, published in final edited form as: Nature. 482(7383):89-93 (2012) (17 pages).

Barouch, et al., "Therapeutic efficacy of potent neutralizing HIV-1-specific monoclonal antibodies in SHIV-infected rhesus monkeys," available in PMC May 14, 2014, published in final edited form as: Nature. 503(7475):224-228 (2013) (24 pages).

Battistini et al., "HIV-1 latency: an update of molecular mechanisms and therapeutic strategies," Viruses. 6(4):1715-58 (2014).

Behrens et al. "Composition and Antigenic Effects of Individual Glycan Sites of a Trimeric HIV-1 Envelope Glycoprotein," Cell Rep. 14(11):2695-706 (2016) (31 pages).

Brief Communication for European Patent Application No. 14847004.0, dated Jun. 21, 2021 (2 pages).

Brooks et al., "Chapter 11: Clearance of Latent Reservoirs." HIV Chemotherapy: A Critical Review. Salvatore T. Butera, Calster Academic Press, 281-303 (2005) (24 pages).

Bruel et al., "Elimination of HIV-1-infected cells by broadly neutralizing antibodies," Nat Commun. 7:10844 (2016) (12 pages).

Burton et al., "Broadly neutralizing antibodies suggest new prospects to counter highly antigenically diverse viruses," available in PMC Jul. 13, 2013, published in final edited form as: Science. 337(6091):183-186 (2012) (13 pages).

Burton et al., "Efficient neutralization of primary isolates of HIV-1 by a recombinant human monoclonal antibody," Science. 266(5187):1024-7 (1994) (5 pages).

Chatellier et al., "Functional mapping of conserved residues located at the VL and VH domain interface of a fab," J Mol Biol. 264(1):1-6 (1996).

Chen et al., "Antibody-based candidate therapeutics against HIV-1: implications for virus eradication and vaccine design," Expert Opin Biol Ther. 13(5): 657-671 (2013) (5 pages).

Chen et al., "Generation and analysis of random point mutations in an antibody CDR2 sequence: many mutated antibodies lose their ability to bind antigen," J Exp Med. 176(3):855-66 (1992).

Communication of a notice of opposition for European Patent No. EP3052132, mailed May 6, 2021 (36 pages).

Communication pursuant to Article 94(3) EPC for European Patent Application No. 14847004.0, dated Jan. 15, 2018 (8 pages).

Communication pursuant to Article 94(3) EPC for European Patent Application No. 14847004.0, dated Oct. 25, 2019 (5 pages).

De Boer et al., "Current estimates for HIV-1 production imply rapid viral clearance in lymphoid tissues," PLoS Comput Biol. 6(9):e1000906 (2010) (9 pages).

Declaration of Dr. Barouch, European regional phase application EP 14847004.0. Oct. 4, 2019 (3 Pages).

Deshpande et al., "HIV-1 clade C escapes broadly neutralizing autologous antibodies with N332 glycan specificity by distinct mechanisms," Retrovirology. 13(1):60 (2016) (9 pages).

Diskin et al., "Increasing the potency and breadth of an HIV antibody by using structure-based rational design," Science. 334(6060):1289-93 (2011) (10 pages).

Diskin et al., "Restricting HIV-1 pathways for escape using rationally designed anti-HIV-1 antibodies," J Exp Med. 210(6):1235-49 (2013).

Extended European Search Report for European Patent Application No. 14847004.0, dated Apr. 19, 2017 (9 pages).

Gama et al., "Reactivation of simian immunodeficiency virus reservoirs in the brain of virally suppressed macaques," AIDS. 31(1):5-14 (2017).

Gautam et al., "Pathogenicity and mucosal transmissibility of the R5-tropic simian/human immunodeficiency virus SHIV(AD8) in rhesus macaques: implications for use in vaccine studies," J Virol. 86(16):8516-26 (2012) (11 pages).

Halper-Stromberg et al., "Broadly Neutralizing Antibodies and Viral Inducers Decrease Rebound from HIV-1 Latent Reservoirs in Humanized Mice," Cell. 158(5): 989-999 (2014).

Hansen et al., "Profound early control of highly pathogenic SIV by an effector memory T-cell vaccine," Nature. 473(7348):523-7 (2011).

Hatziioannou et al., "Animal models for HIV/AIDS research," available in PMC Feb. 19, 2015, published in final edited form as: Nat Rev Microbiol. 10(12):852-867 (2012) (37 pages).

Hellerstein et al., "Directly measured kinetics of circulating T lymphocytes in normal and HIV-1-infected humans," Nat Med. 5(1):83-9 (1999).

Ho et al., "Rapid turnover of plasma virions and CD4 lymphocytes in HIV-1 infection," Nature. 373:123-126 (1995).

Horwitz et al., "HIV-1 suppression and durable control by combining single broadly neutralizing antibodies and antiretroviral drugs in humanized mice," PNAS. 110(41):Supplementary information. (2013) (7 pages).

Horwitz et al., "HIV-1 suppression and durable control by combining single broadly neutralizing antibodies and antiretroviral drugs in humanized mice," Proc Natl Acad Sci U S A. 110(41):16538-43 (2013) (6 pages).

Huang et al., "Broad and potent neutralization of HIV-1 by a gp41-specific human antibody," Nature. 491(7424):406-12 (2012).

Igarashi et al., "Human immunodeficiency virus type 1 neutralizing antibodies accelerate clearance of cell-free virions from blood plasma," Nat Med. 5(2):211-6 (1999).

International Preliminary Report on Patentability for International Patent Application No. PCT/US2014/058383, issued Apr. 5, 2016 (7 pages).

International Preliminary Report on Patentability for International Patent Application No. PCT/US2019/062203, mailed Apr. 7, 2020 (10 pages).

International Search Report and Written Opinion for International Application No. PCT/US2019/033613, mailed Sep. 20, 2019 (27 pages).

International Search Report and Written Opinion for International Application No. PCT/US2019/062203, mailed Apr. 7, 2020 (15 pages).

International Search Report and Written Opinion for International Application No. PCT/US2019/33613, mailed Sep. 20, 2019 (27 pages).

International Search Report and Written Opinion for International Patent Application No. PCT/US2014/58383, mailed Dec. 19, 2014 (19 pages).

Invitation to Pay Additional Fees for International Application No. PCT/US2019/06223, mailed Feb. 11, 2020 (2 pages).

Jaworski et al., "Neutralizing polyclonal IgG present during acute infection prevents rapid disease onset in simian-human immunodeficiency virus SHIVSF162P3-infected infant rhesus macaques," J Virol. 87(19):10447-59 (2013) (13 pages).

(56) References Cited

OTHER PUBLICATIONS

Jayaraman et al., "Evidence for persistent, occult infection in neonatal macaques following perinatal transmission of simian-human immunodeficiency virus SF162P3," J Virol. 81(2):822-34 (2007) (13 pages).
Julg et al., "Broadly neutralizing antibodies targeting the HIV-1 envelope V2 apex confer robust protection against a clade C SHIV challenge," available in PMC Mar. 6, 2018, published in final edited form as: Sci Transl Med. 9(406): eaal1321 (2017) (26 pages).
Julien et al., "Broadly neutralizing antibody PGT121 allosterically modulates CD4 binding via recognition of the HIV-1 gp120 V3 base and multiple surrounding glycans," PLoS Pathog. 9(5):e1003342 (2013) (15 pages).
Kala et al., "Phage displayed antibodies to heat stable alkaline phosphatase: framework region as a determinant of specificity," J Biochem. 132(4):535-41 (2002).
Katlama et al., "Barriers to a Cure: New concepts in targeting and eradicating HIV-1 reservoirs," Lancet. 381(9883):2109-2117 (2013) (19 pages).
Kirschner et al., "Model of HIV-1 disease progression based on virus-induced lymph node homing and homing-induced apoptosis of CD4+ lymphocytes," J Acquir Immune Defic Syndr. 24(4):352-62 (2000).
Kirschner et al., "Role of the thymus in pediatric HIV-1 infection," J Acquir Immune Defic Syndr Hum Retrovirol. 18(2):95-109 (1998).
Klein et al., "Antibodies in HIV-1 vaccine development and therapy," available in PMC Mar. 31, 2014, published in final edited form as: Science. 341(6151):1199-1204 (2013) (17 pages).
Klein et al., "HIV therapy by a combination of broadly neutralizing antibodies in humanized mice," Nature. 492(7427):118-122 (2012) (11 pages).
Klein et al., "Somatic mutations of the immunoglobulin framework are generally required for broad and potent HIV-1 neutralization," Cell. 153(1):126-38 (2013).
Kong et al., "Supersite of immune vulnerability on the glycosylated face of HIV-1 envelope glycoprotein gp120," Nat Struct Mol Biol. 20(7):796-803 (2013) (22 pages).
Kraft et al., "Macaques infected with a CCR5-tropic simian/human immunodeficiency virus (SHIV) develop broadly reactive anti-HIV neutralizing antibodies," J Virol. 81(12):6402-11 (2007) (10 pages).
Kwong et al., "Broadly neutralizing antibodies and the search for an HIV-1 vaccine: the end of the beginning," Nat Rev Immunol. 13(9):693-701 (2013).
Kwong et al., "HIV-1 Vaccines Based on Antibody Identification, B Cell Ontogeny, and Epitope Structure," Immunity. 48(5):855-871 (2018).
Le Douce et al., "Achieving a cure for HIV infection: do we have reasons to be optimistic?" J Antimicrob Chemother. 67(5):1063-74 (2012).
Lee et al., "A Broadly Neutralizing Antibody Targets the Dynamic HIV Envelope Trimer Apex via a Long, Rigidified, and Anionic beta-Hairpin Structure," Immunity. 46(4):690-702 (2017).
Letvin et al., "Immune and genetic correlates of vaccine protection against mucosal infection by SIV in monkeys," Sci Transl Med. 3(81): 81ra36 (2011) (22 pages).
Li et al., "Durable mucosal simian immunodeficiency virus-specific effector memory T lymphocyte responses elicited by recombinant adenovirus vectors in rhesus monkeys," J Virol. 85(21):11007-15 (2011).
Lim et al., "TRIM5alpha modulates immunodeficiency virus control in Rhesus monkeys," PLos Pathog. 6(1):e1000738 (2010) (11 pages).
Liu et al., "Fine mapping of the antigen-antibody interaction of scFv215, a recombinant antibody inhibiting RNA polymerase II from *Drosophila melanogaster*," J Mol Recognit. 12(2):103-11 (1999).
Liu et al., "Immune control of an SIV challenge by a T-cell-based vaccine in rhesus monkeys," available in PMC Jul. 1, 2009, published in final edited form as: Nature. 457(7225):87-91 (2009) (17 pages).
Liu et al., "Magnitude and phenotype of cellular immune responses elicited by recombinant adenovirus vectors and heterologous prime-boost regimens in rhesus monkeys," J Virol. 82(10):4844-52 (2008).
Loffredo et al., "Mamu-B*08-positive macaques control simian immunodeficiency virus replication," J Virol. 81(16):8827-32 (2007).
McLellan et al., "Structure of HIV-1 gp120 V1/V2 domain with broadly neutralizing antibody PG9," available in PMC Dec. 15, 2012, published in final edited form as: Nature. 480(7377):336-343 (2011) (17 pages).
Mehandru et al., "Adjunctive passive immunotherapy in human immunodeficiency virus type 1-infected individuals treated with antiviral therapy during acute and early infection," J Virol. 81(20):11016-31 (2007).
Mendoza et al., "Combination therapy with anti-HIV-1 antibodies maintains viral suppression," available in PMC Mar. 26, 2019, published in final edited form as: Nature. 561(7724):479-84 (2018) (33 pages).
Mothe et al., "Expression of the major histocompatibility complex class I molecule Mamu-A*01 is associated with control of simian immunodeficiency virus SIVmac239 replication," J Virol. 77(4):2736-40 (2003).
Mouquet et al., "Complex-type N-glycan recognition by potent broadly neutralizing HIV antibodies," Proc Natl Acad Sci U.S.A. 109(47):E3268-77 (2012).
Mouquet et al., Supplementary information for "Complex-type N-glycan recognition by potent broadly neutralizing HIV antibodies," Proc Natl Acad Sci U S A. 109(47):E3268-77 (2012) (54 pages).
Moyo et al., "Targeting the N332-supersite of the HIV-1 envelope for vaccine design," Expert Opin Ther Targets. 24(6):499-509 (2020).
NCBI Blast for Accession No. NP_000607.1, retrieved May 10, 2016 (4 pages).
Ng et al., "Passive neutralizing antibody controls SHIV viremia and enhances B cell responses in infant macaques," available in PMC Apr. 3, 2011, published in final edited form as: Nat Med. 16(10):1117-1119 (2010) (14 pages).
Nishimura et al., "Generation of the pathogenic R5-tropic simian/human immunodeficiency virus SHIVAD8 by serial passaging in rhesus macaques," J Virol. 84(9):4769-81 (2010) (13 pages).
Okoye et al., "Progressive CD4+ central-memory T cell decline results in CD4+ effector-memory insufficiency and overt disease in chronic SIV infection," J Exp Med. 204(9):2171-85 (2007).
Pejchal et al., "A potent and broad neutralizing antibody recognizes and penetrates the HIV glycan shield," available in PMC Nov. 25, 2012, published in final edited form as: Science. 334(6059):1097-1103 (2011) (16 pages).
Perelson et al., "Dynamics of HIV infection of CD4+ T cells," Math Biosci. 114(1):81-125 (1993).
Perelson et al., "HIV-1 dynamics in vivo: virion clearance rate, infected cell life-span, and viral generation time," Science. 271(5255):1582-6 (1996).
Pitcher et al., "Development and homeostasis of t cell memory in rhesus macaque," J Immunol. 168(1):29-43 (2002) (16 pages).
Poignard et al., "Neutralizing antibodies have limited effects on the control of established HIV-1 infection in vivo," Immunity. 10(4):431-8 (1999).
Rajpal et al., "A general method for greatly improving the affinity of antibodies by using combinatorial libraries," Proc Natl Acad Sci U S A. 102(24):8466-71 (2005).
Roben et al., "Recognition properties of a panel of human recombinant Fab fragments to the CD4 binding site of gp120 that show differing abilities to neutralize human immunodeficiency virus type 1," J Virol. 68(8):4821-8 (1994).
Sadjadpour et al., "Emergence of gp120 V3 variants confers neutralization resistance in an R5 simian-human immunodeficiency virus-infected macaque elite neutralizer that targets the N332 glycan of the human immunodeficiency virus type 1 envelope glycoprotein," J Virol. 87(15):8798-804 (2013).
Scheid et al., "Broad diversity of neutralizing antibodies isolated from memory B cells in HIV-infected individuals," Nature. 458(7238):636-40 (2009).

(56) References Cited

OTHER PUBLICATIONS

Scheid et al., "Sequence and structural convergence of broad and potent HIV antibodies that mimic CD4 binding," Science. 333(6049):1633-7 (2011).
Shan et al., "From reactivation of latent HIV-1 to elimination of the latent reservoir: the presence of multiple barriers to viral eradication," available in PMC Apr. 6, 2015, published in final edited form as: Bioessays. 35(6):544-52 (2013) (17 pages).
Shan et al., "Unique characteristics of histone deacetylase inhibitors in reactivation of latent HIV-1 in Bcl-2-transduced primary resting CD4+ T cells," J Antimicrob Chemother. 69(1):28-33 (2014).
Sievers et al., "Antibody engineering for increased potency, breadth and half-life," Curr Opin HIV AIDS. 10(3):151-9 (2015).
Siliciano et al., "HIV Latency," Cold Spring Harb Perspect Med. 1(1):a007096 (2011) (19 pages).
Sok et al., "Recombinant HIV envelope trimer selects for quaternary-dependent antibodies targeting the trimer apex," Proc Natl Acad Sci U S A. 111(49):17624-9 (2014).
Sok et al., "The effects of somatic hypermutation on neutralization and binding in the PGT121 family of broadly neutralizing HIV antibodies," PLoS Pathog. 9(11):e1003754 (2013) (20 pages).
Stephenson et al., "Broadly Neutralizing Antibodies for HIV Eradication," Curr HIV/AIDS Rep. 13(1):31-7 (2016).
Stephenson et al., "Gag-specific cellular immunity determines in vitro viral inhibition and in vivo virologic control following simian immunodeficiency virus challenges of vaccinated rhesus monkeys," J Virol. 86(18):9583-9 (2012) (7 pages).
Supplementary Information for Walker et al., "Broad neutralization coverage of HIV by multiple highly potent antibodies," Nature. 477(7365):466-470 (2011) (15 pages).
Third Party Observation for International Patent Application No. 2019062203, dated Nov. 19, 2019 (8 pages).
Trkola et al., "Delay of HIV-1 rebound after cessation of antiretroviral therapy through passive transfer of human neutralizing antibodies," Nat Med. 11(6):615-22 (2005) (8 pages).
Van den Kerkhof et al., "HIV-1 escapes from N332-directed antibody neutralization in an elite neutralizer by envelope glycoprotein elongation and introduction of unusual disulfide bonds," Retrovirology. 13(1):48 (2016) (19 pages).
Walker et al., "Broad and potent neutralizing antibodies from an African donor reveal a new HIV-1 vaccine target," Science. 326(5950):285-9 (2009).
Walker et al., "Broad neutralization coverage of HIV by multiple highly potent antibodies," available in PMC Jul. 10, 2012, published in final edited form as: Nature. 477(7365):466-70 (2011) (14 pages).
Walker et al., "Broad neutralization coverage of HIV by multiple highly potent antibodies," Nature. 477(7365):466-470 (2011) (20 pages).
West et al., "Computational analysis of anti-HIV-1 antibody neutralization panel data to identify potential functional epitope residues," Proc Natl Acad Sci USA. 110(26):10598-603 (2013).
West et al., "Structural Insights on the Role of Antibodies in HIV-1 Vaccine and Therapy," Cell. 156(4):633-648 (2014).
Whitney et al., "T-cell vaccination reduces simian immunodeficiency virus levels in semen," J Virol. 83(20):10840-3 (2009).
Wu et al., "Rational design of envelope identifies broadly neutralizing human monoclonal antibodies to HIV-1," Science. 329(5993):856-61 (2010).
Yant et al., "The high-frequency major histocompatibility complex class I allele Mamu-B*17 is associated with control of simian immunodeficiency virus SIVmac239 replication," J Virol. 80(10):5074-7 (2006).
Yu et al., "Predicting the broadly neutralizing antibody susceptibility of the HIV reservoir," JCI Insight. 4(17):e130153 (2019) (18 pages).
Zettlitz et al., "IBC's 23rd Annual Antibody Engineering, 10th Annual Antibody Therapeutics International Conferences and the 2012 Annual Meeting of the Antibody Society," MAbs. 5(2):178-201 (2012).
Zhou et al., "Structural basis for broad and potent neutralization of HIV-1 by antibody VRC01," available in PMC Aug. 13, 2011, published in final edited format as: Science. 329(5993):811-7 (2010) (19 pages).
Devin Sok et al: "Recombinant HIV envelope trimer selects for quaternary-dependent antibodies targeting the trimer apex", Proceedings of the National Academy of Sciences, 111(49) Dec. 9, 2014 (Dec. 9, 2014), pp. 17624-17629 (17 pages).
Jeong Hyun Lee et al: "A Broadly Neutralizing Antibody Targets the Dynamic HIV Envelope Trimer Apex via a Long, Rigidified, and Anionic beta-Hairpin Structure", Immunity, 46(4), Apr. 18, 2017, pp. 690-702 (14 pages).
Extended European Search Report for European Patent Application No. 19886693.1, dated Mar. 14, 2023 (17 pages).
Communication pursuant to Rule 63(1) EPC for European Patent Application No. 19807138.3, dated Jan. 3, 2022 (4 pages).
Extended European Search Report for European Patent Application No. 19807138.3, dated Jun. 1, 2022 (10 pages).
Sela-Culang et al., "The structural basis of antibody-antigen recognition," Front Immunol. 4:302 (2013) (13 pages).
Tiller et al., "Arginine mutations in antibody complementarity-determining regions display context-dependent affinity/specificity trade-offs," J Biol Chem. 292(40):16638-16652 (2017).
Xiang et al., "Framework residues 71 and 93 of the chimeric B72.3 antibody are major determinants of the conformation of heavy-chain hypervariable loops," J Mol Biol. 253(3):385-90 (1995).
Hua et al., "Engineering broadly neutralizing antibodies for HIV prevention and therapy," Adv Drug Deliv Rev. 103:157-173 (2016) (42 pages).

* cited by examiner

FIG. 2

| Ab Structure | Kappa Light Chain | | | | | | | | | IgG1 Heavy Chain | | | | | | | | |
|---|---|---|---|---|---|---|---|---|---|---|---|---|---|---|---|---|---|---|
| | KV:F2 | KV:H9 | KV:S12 | KV:S18 | KV:R47 | KV:D73 | KV:K74 | KV:T85 | KV:T90 | HV:P25 | HV:N27 | HV:L29 | HV:Q46 | HV:D71 | HV:W72 | HV:Q82 | HV:T87 | HV:D113 |
| MS-66 | I | | | | | | | | | | | | | | | | | |
| MS-67 | | L | | | | | | | | | | | | | | | | |
| MS-68 | | | P | | | | | | | | | | | | | | | |
| MS-69 | | | | P | | | | | | | | | | | | | | |
| MS-70 | | | | | Q | | | | | | | | | | | | | |
| MS-71 | | | | | | G | | | | | | | | | | | | |
| MS-72 | | | | | | | T | | | | | | | | | | | |
| MS-73 | | | | | | | | A | | | | | | | | | | |
| MS-74 | | | | | | | | | V | | | | | | | | | |
| MS-75 | | | | | | | | | | S | | | | | | | | |
| MS-76 | | | | | | | | | | | Y | | | | | | | |
| MS-77 | | | | | | | | | | | | F | | | | | | |
| MS-78 | | | | | | | | | | | | | E | | | | | |
| MS-79 | | | | | | | | | | | | | | T | | | | |
| MS-80 | | | | | | | | | | | | | | | R | | | |
| MS-81 | | | | | | | | | | | | | | | | E | | |
| MS-82 | | | | | | | | | | | | | | | | | R | |
| MS-83 | | | | | | | | | | | | | | | | | | E |
| MS-84 | | L | P | P | Q | | | A | V | | | | | | | | R | |
| MS-85 | I | | | | | G | T | | | | | | | | | | | |
| MS-86 | | | | | | | | | | S | Y | F | | | | | | |
| MS-87 | | | | | | | | | | | | | | T | R | | | |
| MS-88 | | | | | | | | | | S | Y | F | | T | R | | | |
| MS-89 | | L | | | | | | | | | Y | | | T | | | | |
| MS-90 | | L | | | | | | | | S | Y | F | | | | | | |
| MS-91 | | L | | | | | T | | | S | Y | | | | | | | |
| MS-92 | I | | | | | | | | | | | | E | | R | | R | |

FIG. 3

| Ab Structure | Kappa Light Chain KV:F2 | KV:H9 | KV:S12 | KV:S18 | KV:R47 | KV:D73 | KV:K74 | KV:T85 | KV:T90 | IgG1 Heavy Chain HV:P25 | HV:N27 | HV:L29 | HV:Q46 | HV:D71 | HV:W72 | HV:Q82 | HV:T87 | HV:D113 |
|---|---|---|---|---|---|---|---|---|---|---|---|---|---|---|---|---|---|---|
| MS-93 | I | L | | | | | | | | | | | | | | | | |
| MS-94 | I | | | P | | | | | | | | | | | | | | |
| MS-95 | I | | | | | G | | | | | | | | | | | | |
| MS-96 | I | | | | | | | A | | | | | | | | | | |
| MS-97 | | L | | P | | | | | | | | | | | | | | |
| MS-98 | | L | | | | G | | | | | | | | | | | | |
| MS-99 | | L | | | | | | A | | | | | | | | | | |
| MS-100 | | | | P | | G | | | | | | | | | | | | |
| MS-101 | | | | P | | | | A | | | | | | | | | | |
| MS-102 | | | | | | G | | A | | | | | | | | | | |
| MS-103 | I | L | | P | | | | | | | | | | | | | | |
| MS-104 | I | L | | | | G | | | | | | | | | | | | |
| MS-105 | I | L | | | | | | A | | | | | | | | | | |
| MS-106 | I | | | P | | G | | | | | | | | | | | | |
| MS-107 | I | | | P | | | | A | | | | | | | | | | |
| MS-108 | I | | | | | G | | A | | | | | | | | | | |
| MS-109 | | L | | P | | G | | | | | | | | | | | | |
| MS-110 | | L | | P | | | | A | | | | | | | | | | |
| MS-111 | | L | | | | G | | A | | | | | | | | | | |
| MS-112 | | | | P | | G | | A | | | | | | | | | | |
| MS-113 | I | L | | P | | G | | | | | | | | | | | | |
| MS-114 | I | L | | P | | | | A | | | | | | | | | | |
| MS-115 | I | L | | | | G | | A | | | | | | | | | | |
| MS-116 | I | | | P | | G | | A | | | | | | | | | | |
| MS-117 | | L | | P | | G | | A | | | | | | | | | | |
| MS-118 | I | L | | P | | G | | A | | | | | | | | | | |

ANTIBODY THERAPIES FOR HUMAN IMMUNODEFICIENCY VIRUS (HIV)

SEQUENCE LISTING

The instant application contains a Sequence Listing which has been submitted electronically in ASCII format and is hereby incorporated by reference in its entirety. Said ASCII copy, created on Nov. 18, 2019 is named 01948-263WO2_Sequence_Listing_11.18.19_ST25 and is 416,700 bytes in size.

BACKGROUND OF THE INVENTION

Acquired immunodeficiency syndrome (AIDS) is a chronic, potentially life-threatening condition caused by the human immunodeficiency virus (HIV). In 2010, there were approximately 1.8 million deaths attributed to AIDS, and nearly 30 million people with AIDS have died worldwide since the epidemic began (Centers for Disease Control and Prevention. *HIV Surveillance Report*. Vol. 23, 2011).

Even though current therapies, such as antiretroviral therapies (ARTs), have reduced AIDS-related deaths in many developed nations, HIV infections continue to be a serious health issue. According to the latest estimates from the Centers for Disease Control and Prevention (CDC), an estimated 38,500 people became newly infected with HIV in the United States in 2015. At the end of 2015, an estimated 973,846 persons in the United States were living with diagnosed HIV infection, and the overall prevalence of people with diagnosed HIV was 303.5 per 100,000 people (Centers for Disease Control and Prevention. *HIV Surveillance Report,* 2016; vol. 28). Globally, about 36.9 million people were living with HIV in 2017, with about 1.8 million people becoming newly infected with HIV in 2017 (UNAIDS. Global HIV & AIDS statistics—2018 fact sheet).

Thus, there remains an unmet need in the field for therapies capable of treating an HIV-infected individual or blocking an HIV infection in a subject at risk of HIV transmission.

SUMMARY OF THE INVENTION

Featured herein are antibody variants (e.g., PGDM1400 variant antibodies) or antigen-binding fragments thereof that retain the ability of the native antibody to inactivate or neutralize viruses (e.g., HIV-1), while showing significant improvements in biophysical properties. Also featured are methods of treating or blocking human immunodeficiency virus (HIV) infection by administration of these antibodies or antigen-binding fragments thereof.

A first aspect features a PGDM1400 variant antibody or antigen-binding fragment thereof that has: (a) a heavy chain variable domain having a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 136; and (b) a light chain variable domain having a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 135, wherein the antibody or antigen-binding fragment thereof has: (i) at least one of the following mutations in the heavy chain variable domain sequence: HV:P25S, HV:N27Y, HV:L29F, HV:Q46E, HV:D71T, HV:W72R, HV:Q82E, HV:T87R, and HV:D113E; and/or (ii) at least one of the following mutations in the light chain variable domain sequence: KV:F2I, KV:H9L, KV:S12P, KV:S18P, KV:R47Q, KV:D73G, KV:K74T, KV:T85A, and KV:T90V. In some embodiments of the above aspect, the antibody or antigen-binding fragment thereof has at least one (e.g., at least one, at least two, at least three, at least four, at least five, at least six, or more) of the mutations (e.g., KV:F2I, KV:H9L, KV:S12P, KV:S18P, KV:R47Q, KV:D73G, KV:K74T, KV:T85A, and KV:T90V) in the light chain variable domain, and no mutation in the heavy chain variable domain. In other embodiments, the antibody or antigen-binding fragment thereof has at least one (e.g., at least one, at least two, at least three, at least four, at least five, at least six, or more) of the mutations (e.g., HV:P25S, HV:N27Y, HV:L29F, HV:Q46E, HV:D71T, HV:W72R, HV:Q82E, HV:T87R, and HV:D113E) in the heavy chain variable domain, and no mutation in the light chain variable domain. In additional embodiments, the antibody or antigen-binding fragment thereof has at least one (e.g., at least one, at least two, at least three, at least four, at least five, at least six, or more) of the mutations (e.g., HV:P25S, HV:N27Y, HV:L29F, HV:Q46E, HV:D71T, HV:W72R, HV:Q82E, HV:T87R, and HV:D113E) in the heavy chain variable domain, and at least one (e.g., at least one, at least two, at least three, at least four, at least five, at least six, or more) of the mutations (e.g., KV:F2I, KV:H9L, KV:S12P, KV:S18P, KV:R47Q, KV:D73G, KV:K74T, KV:T85A, and KV:T90V) in the light chain variable domain.

The antibody or antigen-binding fragment thereof may also include an Fc domain. The Fc domain of the antibody or antigen-binding fragment thereof may have the sequence of SEQ ID NO: 137, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 137. In other instances, the Fc domain of the antibody or antigen-binding fragment thereof described herein may have the sequence of SEQ ID NO: 138, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 138. In some embodiments, the Fc domain of the antibody or antigen-binding fragment thereof includes a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 137, and a M87L and/or a N93S mutation. In additional embodiments, the Fc domain of the antibody or antigen-binding fragment thereof described herein further includes the sequence of SEQ ID NO: 139, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 139. In some instances, the Fc domain of the antibody or antigen-binding fragments thereof described herein has: (i) the sequence of SEQ ID NO: 140, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 140; or (ii) the sequence of SEQ ID NO: 141, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 141.

In some embodiments, the antibody or antigen-binding fragment thereof further includes an Ig domain with the sequence of SEQ ID NO: 142, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 142; and/or a Hinge region with the sequence of SEQ ID NO: 143, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 143.

In some embodiments of the above aspect, the antibody or antigen-binding fragment thereof is a V2-specific antibody.

In particular embodiments, the featured antibody or antigen-binding fragment thereof is:

(a) MS-66, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 144 or amino acids 20-238 of SEQ ID NO: 18;

(b) MS-67, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 145 or amino acids 20-238 of SEQ ID NO: 20;

(c) MS-68, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 146 or amino acids 20-238 of SEQ ID NO: 22;

(d) MS-69, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 147 or amino acids 20-238 of SEQ ID NO: 24;

(e) MS-70, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 SEQ ID NO: 10, and a light chain variable domain having the sequence of SEQ ID NO: 148 or amino acids 20-238 of SEQ ID NO: 26;

(f) MS-71, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 149 or amino acids 20-238 of SEQ ID NO: 28;

(g) MS-72, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 150 or amino acids 20-238 of SEQ ID NO: 30;

(h) MS-73, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 151 or amino acids 20-238 of SEQ ID NO: 32;

(i) MS-74, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 152 or amino acids 20-238 of SEQ ID NO: 34;

(j) MS-75, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 153 or amino acids 20-490 of SEQ ID NO: 36, and a light chain variable domain having the sequence of SEQ ID NO: 135 or amino acids 20-238 of SEQ ID NO: 2;

(k) MS-76, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 154 or amino acids 20-490 of SEQ ID NO: 38, and a light chain variable domain having the sequence of SEQ ID NO: 135 or amino acids 20-238 of SEQ ID NO: 2;

(l) MS-77, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 155 or amino acids 20-490 of SEQ ID NO: 40, and a light chain variable domain having the sequence of SEQ ID NO: 135 or amino acids 20-238 of SEQ ID NO: 2;

(m) MS-78, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 156 or amino acids 20-490 of SEQ ID NO: 42, and a light chain variable domain having the sequence of SEQ ID NO: 135 or amino acids 20-238 of SEQ ID NO: 2;

(n) MS-79, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 157 or amino acids 20-490 of SEQ ID NO: 44, and a light chain variable domain having the sequence of SEQ ID NO: 135 or amino acids 20-238 of SEQ ID NO: 2;

(o) MS-80, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 158 or amino acids 20-490 of SEQ ID NO: 46, and a light chain variable domain having the sequence of SEQ ID NO: 135 or amino acids 20-238 of SEQ ID NO: 2;

(p) MS-81, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 159 or amino acids 20-490 of SEQ ID NO: 48, and a light chain variable domain having the sequence of SEQ ID NO: 135 or amino acids 20-238 of SEQ ID NO: 2;

(q) MS-82, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 160 or amino acids 20-490 of SEQ ID NO: 50, and a light chain variable domain having the sequence of SEQ ID NO: 135 or amino acids 20-238 of SEQ ID NO: 2;

(r) MS-83, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 54, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 54; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 161 or amino acids 20-490 of SEQ ID NO: 52, and a light chain variable domain having the sequence of SEQ ID NO: 135 or amino acids 20-238 of SEQ ID NO: 2;

(s) MS-84, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 163 or amino acids 20-490 of SEQ ID NO: 58, and a light chain variable domain having the sequence of SEQ ID NO: 162 or amino acids 20-238 of SEQ ID NO: 56;

(t) MS-85, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 164 or amino acids 20-238 of SEQ ID NO: 60;

(u) MS-86, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 165 or amino acids 20-490 of SEQ ID NO: 62, and a light chain variable domain having the sequence of SEQ ID NO: 135 or amino acids 20-238 of SEQ ID NO: 2;

(v) MS-87, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 166 or amino acids 20-490 of SEQ ID NO: 64, and a light chain variable domain having the sequence of SEQ ID NO: 135 or amino acids 20-238 of SEQ ID NO: 2;

(w) MS-88, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 167 or amino acids 20-490 of SEQ ID NO: 66, and a light chain variable domain having the sequence of SEQ ID NO: 135 or amino acids 20-238 of SEQ ID NO: 2;

(x) MS-89, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 169 or amino acids 20-490 of SEQ ID NO: 70, and a light chain variable domain having the sequence of SEQ ID NO: 168 or amino acids 20-238 of SEQ ID NO: 68;

(y) MS-90, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 171 or amino acids 20-490 of SEQ ID NO: 74, and a light chain variable domain having the sequence of SEQ ID NO: 170 or amino acids 20-238 of SEQ ID NO: 72;

(z) MS-91, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 173 or amino acids 20-490 of SEQ ID NO: 78, and a light chain variable domain having the sequence of SEQ ID NO: 172 or amino acids 20-238 of SEQ ID NO: 76;

(aa) MS-92, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 175 or amino acids 20-490 of SEQ ID NO: 82, and a light chain variable domain having the sequence of SEQ ID NO: 174 or amino acids 20-238 of SEQ ID NO: 80;

(bb) MS-119, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s)

(e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 135 or amino acids 20-238 of SEQ ID NO: 2;

(cc) MS-93, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 176 or amino acids 20-238 of SEQ ID NO: 84;

(dd) MS-94, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 177 or amino acids 20-238 of SEQ ID NO: 86;

(ee) MS-95, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 178 or amino acids 20-238 of SEQ ID NO: 88;

(ff) MS-96, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 179 or amino acids 20-238 of SEQ ID NO: 90;

(gg) MS-97, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 180 or amino acids 20-238 of SEQ ID NO: 92;

(hh) MS-98, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 181 or amino acids 20-238 of SEQ ID NO: 94;

(ii) MS-99, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 182 or amino acids 20-238 of SEQ ID NO: 96;

(jj) MS-100, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 183 or amino acids 20-238 of SEQ ID NO: 98;

(kk) MS-101, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 184 or amino acids 20-238 of SEQ ID NO: 100;

(ll) MS-102, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 185 or amino acids 20-238 of SEQ ID NO: 102;

(mm) MS-103, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 186 or amino acids 20-238 of SEQ ID NO: 104;

(nn) MS-104, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 187 or amino acids 20-238 of SEQ ID NO: 106;

(oo) MS-105, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 188 or amino acids 20-238 of SEQ ID NO: 108;

(pp) MS-106, which is:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 189 or amino acids 20-238 of SEQ ID NO: 110;

(qq) MS-107, which is:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 190 or amino acids 20-238 of SEQ ID NO: 112;

(rr) MS-108, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 191 or amino acids 20-238 of SEQ ID NO: 114;

(ss) MS-109, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 192 or amino acids 20-238 of SEQ ID NO: 116;

(tt) MS-110, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 193 or amino acids 20-238 of SEQ ID NO: 118;

(uu) MS-111, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 194 or amino acids 20-238 of SEQ ID NO: 120;

(vv) MS-112, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 195 or amino acids 20-238 of SEQ ID NO: 122;

(ww) MS-113, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 196 or amino acids 20-238 of SEQ ID NO: 124;

(xx) MS-114, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 197 or amino acids 20-238 of SEQ ID NO: 126;

(yy) MS-115, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 198 or amino acids 20-238 of SEQ ID NO: 128;

(zz) MS-116, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 199 or amino acids 20-238 of SEQ ID NO: 130;

(aaa) MS-117, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 200 or amino acids 20-238 of SEQ ID NO: 132; or (bbb) MS-118, which has:

(i) a heavy chain (HC) complementarity determining region (CDR) HC-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; and/or (ii) a heavy chain variable domain having the sequence of SEQ ID NO: 136 or amino acids 20-490 of SEQ ID NO: 10, and a light chain variable domain having the sequence of SEQ ID NO: 201 or amino acids 20-238 of SEQ ID NO: 134.

The light and heavy chain variable domain of the PGDM1400 variant antibody or antigen-binding fragment thereof featured herein may be preceded by a signal peptide. For example, amino acids 1-19 of the light and heavy chain domains of the PGDM1400 variant antibody or antigen-binding fragment thereof may correspond to the signal peptide (see, e.g., amino acids 1-19 of SEQ ID NOs: 2 and 10, respectively). The signal peptide may be included in the amino acid sequences for the light and heavy chain domains of the PGDM1400 variant antibody or antigen-binding fragment thereof (or encoded by a nucleic acid molecule corresponding to the PGDM1400 variant antibody or antigen-binding fragment thereof) for the purpose of expressing the PGDM1400 variant antibody or antigen-binding fragment thereof in an expression system (e.g., a mammalian expression system), in which the signal peptide is cleaved during maturation of the PGDM1400 variant antibody or antigen-binding fragment thereof and secretion from the cell expressing the PGDM1400 variant antibody or antigen-binding fragment thereof. The sequence identifiers for the amino acid sequences of the heavy and light chain variable domains of the PGDM1400 antibody variants or antigen-binding fragments thereof described herein may include amino acids 1-19 of the signal peptide. Thus, residue number 1 of the mature form of the heavy and light chain variable domains of the PGDM1400 antibody variants or antigen-binding fragments thereof described herein may begin at amino acid residue 20. All the mutations described herein refer to the location of the mutated residue in the mature linear form (the mature linear form lacking the signal peptide corresponding to residues 1-19; e.g., the light chain variable domain mutation KV:F2I refers to a F-to-I substitution at position 2 of the mature linear form of the antibody light chain domain (see, e.g., SEQ ID NO: 144 of MS-66), which corresponds to position 21 in the amino acid sequence with the signal peptide (see, e.g., SEQ ID NO: 18 of MS-66 from Table 1).

In specific embodiments, the PGDM1400 variant antibody or antigen-binding fragment thereof is selected from the group consisting of (a), (b), (d), (f), (h), (cc), (dd), (ee), (ff), (gg), (hh), (ii), (jj), (kk), (ll), (mm), (nn), (oo), (pp), (qq), (rr), (ss), (tt), (uu), (vv), (ww), (xx), (yy), (zz), (aaa), and (bbb) noted above. uu), (vv), (ww), (xx), (yy), (zz), (aaa), and (bbb). In preferred embodiments, the PGDM1400 variant antibody or antigen-binding fragment thereof featured herein may be selected from the group consisting of (cc), (dd), (ee), (ff), (gg), (hh), (ii), (jj), (kk), (ll), (mm), (nn), (oo), (pp), (qq), (rr), (ss), (tt), (uu), (vv), (ww), (xx), (yy), (zz), (aaa), and (bbb). In more preferred embodiments, the antibody or antigen-binding fragment is selected from the group consisting of (cc), (dd), (ee), (ff), (mm), (nn), (oo), (pp), (qq), (rr), (ww), (xx), (yy), (zz), and (bbb). In desired embodiments, the antibody or antigen-binding fragment is (cc) (e.g., MS-93). In some embodiments, the CDR sequences noted above for (a)-(bbb) may differ by one, two, three, four, five, six, seven, eight, nine, or ten amino acid residues from the recited sequences. In such embodiments, insertion, deletion, or substitution of one, two, three, four, five, six, seven, eight, nine, or ten amino acid residues may account for amino acid difference of the CDR sequences from the recited CDR sequences. The amino acid substitution in the CDR(s), if present, may be a conservative amino acid substitution.

In certain instances, as compared to an antibody or antigen-binding fragment thereof lacking the at least one mutation in the heavy chain variable domain and/or the light chain variable domain, the featured antibody or antigen-binding fragment thereof described herein exhibits one or more of the following properties: (i) neutralization of one or more of the following pseudoviruses of HIV: SC422661.8, RHPA4259.7, Du172.17, BB1012-11.TC21, CNE52, 0260.v5.c36, 263-8, SC05.8C11.2344, X1193_c1, Cell 76_A3, AC10.0.29, and 6952.v1.c20; (ii) increased solubility, in which at least about 1 mg/ml (e.g., about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 5.5 mg/ml, 6.0 mg/ml, 6.5 mg/ml, 7.0 mg/ml, 7.5 mg/ml, 8.0 mg/ml, 8.5 mg/ml, 9.0 mg/ml, 9.5 mg/ml, or 10.0 mg/ml) of the antibody or antigen-binding fragment thereof is soluble in a solution containing about 6-10% PEG 10,000 (e.g., about 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10% PEG 10,000), wherein preferably about 1 mg/ml of the antibody or fragment thereof is soluble in a solution with a concentration of about 9.4% PEG 10,000; (iii) increased stability (e.g., a reduction in aggregation and/or formation of high molecular weight species of at least about 1%, 2%, 3%, 4%, 5%, 6%, 7%, 8%, 9%, 10%, 15%, 20%, 25%, or 30%, or more) at low pH, such as at a pH of less than about 5.0 (e.g., pH less than 4.6, pH less than 4.3, pH less than 4.0, pH less than 3.6, or pH equal to about 3.3); (iv) increased thermal stability (e.g., an increase in the melting temperature of at least about 1° C., 2° C., 3° C., 4° C., 5° C., 6° C., 7° C., 8° C., 9° C., 10° C. or more, relative to a PGDM1400 antibody without the at least one mutation), such as stability at a temperature in the range of about 20-95° C., wherein preferably the temperature is about 68° C. or about 69.2° C.; and/or (v) increased chemical stability (e.g., as assessed by resistance of the PGDM1400 variant antibody or antigen-binding fragment thereof to chemical denaturation, such as by guanidine hydrochloride (GuHCl), such as GuHCl in an amount of greater than about 2 M (e.g., greater than 2.5 M, greater than 3.0 M, greater than 3.5 M, greater than 4.0 M, greater than 4.5 M, greater than 5.0 M, greater than 5.5 M, or equal to about 6.0 M). In certain embodiments, the featured antibody or antigen-binding fragment thereof exhibits reduced aggregation (e.g., the monomer content is more than about 60% (e.g., more than about 65%, 70%, 75%, 80%, 85%, 90%, 95%, 96%, or 97%), and/or the oligomer content is less than about 10% (e.g., less than about 9%, 8%, 7%, 6%, 5%, 4%, 3%, 2%, 1%, 0.5%, 0.4%, or 0.3%)). The antibody or antigen-binding fragment thereof exhibits improved manufacturability (e.g., reduced aggregation during manufacture) and storage stability (e.g., does not aggregate during storage over a period of time (e.g., storage over about 2 days, 3 days, 4 days, 5 days, 6 days, 1 week, 2 weeks, 3 weeks, 1 month, 2 months, 3 months, 4 months, 5 months, 6 months, 1 year, 2 years, 3 years, 4 years, 5 years, or more)), such as at a temperature of about −20° C. to about 25° C. (e.g., about −30° C., −25° C., −20° C., −15° C., −10° C., −5° C., 0° C., 5° C., 10° C., 15° C., 20° C., 25° C., 30° C., or 35° C.).

In some embodiments, the antibody or antigen-binding fragment thereof featured herein has a half-life of at least about 1 hour (e.g., at least about 1 hour, 2 hour, 3 hour, 4 hour, 5 hour, 6 hour, 7 hour, 8 hour, 9 hour, 10 hour, 11 hour, 12 hour, 13 hour, 14 hour 15 hour, 16 hour, 17 hour, 18 hour, 19 hour, 20 hour, 21 hour, 22 hour, 23 hour, 1 day, 2 day, 3 day, 4 day, 5 day, 6 day, 7 day, 8 day, 9 day, 10 day, 11 day, 12 day, 13 day, 14 day, 15 day, 16 day, 17 day, 18 day, 19 day, 20 day, 21 day, 22 day, 23 day, 24 day, 25 day, 26 day, 27 day, 28 day, or more) in vitro or in vivo (e.g., in a fluid, such as blood, following administration to a subject (e.g., a human)).

In some embodiments, the antibody or antigen-binding fragment thereof featured herein binds to a parental PGDM1400 anti-idiotype (ID) antibody. In some embodiments, the PGDM1400 variant antibodies or antigen-binding fragments thereof described herein exhibit the same affinity (e.g., binding affinity) for the parental PGDM1400 anti-ID antibody as antibody PGDM1400 or have an affinity (e.g., binding affinity) for the parental PGDM1400 anti-ID antibody that is about ±10% of the affinity exhibited by antibody PGDM1400.

In some embodiments, the antibody or antigen-binding fragment thereof is one or more of a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a NANOBODY™, an antibody-like protein scaffold, a domain antibody, a Fv fragment, a Fab fragment, a F(ab')2 molecule, and a tandem scFv (taFv).

Also featured is a polynucleotide encoding the antibody or antigen-binding fragment thereof, and a vector (e.g., an expression vector, such as a prokaryotic or eukaryotic expression vector) containing the polynucleotide. In certain embodiments, the vector is a viral vector, such as an adenovirus (Ad) vector (e.g., a serotype 2, 5, 11, 12, 24, 26, 34, 35, 40, 48, 49, 50, 52, or Pan9 adenovirus, or a human, chimpanzee, or rhesus adenovirus), a retrovirus (e.g., a γ-retrovirus or a lentivirus), a poxvirus, an adeno-associated virus, a baculovirus, a herpes simplex virus, and a vaccinia virus (e.g., a modified vaccinia Ankara (MVA)). Further featured is a host cell, such as a prokaryotic cell or a eukaryotic cell (e.g., a mammalian cell, such as a Chinese Hamster Ovary (CHO) cell or a Human Embryonic Kidney 293 (HEK293) cell) containing the polynucleotide or the vector.

Also featured herein is a composition with the aforementioned antibody or antigen-binding fragment thereof, the polynucleotide encoding the antibody or antigen-binding fragment thereof, the vector containing the polynucleotide, or the host cell with the polynucleotide or the vector (e.g., a prokaryotic cell or a eukaryotic cell (e.g., a mammalian cell, such as a CHO or a HEK293 cell)). In some instances, the composition further includes a pharmaceutically acceptable carrier, excipient, or diluent.

In additional instances, the composition further includes an immunomodulator (e.g., AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, a gp120-depleted, inactivated $HZ_{321}$ virus (e.g.

REMUNE™), CD4 (e.g., recombinant soluble CD4), rCD4-IgG hybrids, SK&F106528 Soluble T4, Thymopentin, Tumor Necrosis Factor, or Infliximab. In added embodiments, the composition further includes at least one reservoir activator, such as a PKC agonist (e.g., a phorbol ester, a macrocyclic lactone such as bryostatin-1, or a diterpene such as an ingenol compound), a cytokine or chemokine (e.g., interleukin (IL)-7, IL-15, or interferon-alpha (IFN-$\alpha$)), a Toll-like receptor (TLR) agonist (e.g., a TLR 1/2 agonist (e.g., Pam3CSK4), a TLR3 agonist (e.g., Poly-ICLC), a TLR5 agonist (e.g., flagellin), a TLR7 agonist (e.g., GS-9620), or a TLR9 agonist (e.g., MGN1703 and CpG7909)), an immune checkpoint inhibitor (e.g., anti-PD-1 monoclonal antibody, an anti-PD-1 ligand (PD-L1) monoclonal antibody, or an anti-CTLA-4 monoclonal antibody), a histone deacetylase (HDAC) inhibitor (e.g., romidepsin, vorinostat, belinostat, LAQ824, panobinostat, entinostat, C1994, or mocetinostat), or a small molecule reservoir activator (e.g., disulfiram, a benzotriazole derivative (e.g., 3-Hydroxy-1,2,3-benzotriazin-4 ((3H)-one (HODHBt); a SMAC mimetic), or a BRG-Brahma Associated Factor (BAF) inhibitor (e.g., caffeic acid phenethyl ester or pyrimethamine)). In additional instances, the composition further includes an antiretroviral agent (ARV) (e.g., lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc, raltegravir, ibalizumab, IL-2, IL-12, or alpha-epibromide). In some embodiments, the composition further includes one, two, three, or more different HIV-specific broadly neutralizing antibodies (bnAb), such as a CD4 binding site (CD4bs)-specific antibody (e.g., 3BNC117 or VRC07-523), an N332 glycan-dependent antibody (e.g., PGT121, or a variant thereof; see WO/2015/048770; US 2017/0190763; and U.S. Patent Application No. 62/675,102, which are incorporated herein by reference in entirety), or a V2-specific antibody (e.g., CAP256-VRC26 or the parental PGDM1400; see U.S. Pat. No. 10,093,720 B2; Sok et al., *Proct. Natl. Acad. Sci.* 111:17624-17629, 2014; and Julg et al., *Sci. Transl. Med.* 9: eaal1321, 2017, which are incorporated herein by reference in their entirety).

In some embodiments, the composition includes the antibody or antigen-binding fragment thereof in an amount of about 0.01-5000 mg (e.g., about 0.01-1000 mg, about 0.01-500 mg, about 0.05-500 mg, about 0.05-100 mg, about 0.1-100 mg, about 0.1-50 mg, about 0.1-10 mg, or about 1-10 mg). In some instances, the composition is formulated for subcutaneous, intramuscular, intradermal, transdermal, intranasal, or oral administration, or administration as an infusion (e.g., a continuous infusion or a bolus infusion). In some embodiments, the composition is formulated in a volume of about 1000 ml or less (e.g., about 900 ml, 800 ml, 700 ml, 600 ml, 500 ml, 400 ml, 300 ml, 200 ml, 100 ml, 50 ml, 10 ml, 9 ml, 8 ml, 7 ml, 6 ml, 5 ml, 4 ml, 3 ml, 2 ml, or 1 ml, or a volume between about 0.1-1 ml (e.g., about 0.2 ml, 0.3 ml, 0.4 ml, 0.5 ml, 0.6 ml, 0.7 ml, 0.8 ml, or 0.9 ml)). For example, the composition may include an amount of the antibody or antigen-binding fragment thereof of 0.01-500 mg in a volume of 0.1 ml to 500 ml.

Also featured is a method of treating or blocking an HIV infection in a subject by administering to the subject the antibody or antigen-binding fragment thereof, or a composition comprising the same. In some embodiments, the antibody or antigen-binding fragment thereof or the composition is administered to the subject in a dosage form, such as a dose of about 0.01-5000 mg (e.g., about 0.01-4000 mg, about 0.01-3000 mg, about 0.01-2000 mg, about 0.05-2000 mg, about 0.05-1000 mg, or about 0.1-1000 mg). In some instances, about 0.01-100 mg/kg (e.g., about 0.05-100 mg/kg, about 0.1-100 mg/kg, or about 0.5-40 mg/kg) of the antibody or antigen-binding fragment thereof is administered to the subject.

In some embodiments, the antibody or antigen-binding fragment thereof is administered to the subject two or more times. In some instances, the antibody or antigen-binding fragment thereof is administered to the subject one or more times daily, weekly, every two weeks, every three weeks, or monthly. In some embodiments, a single dose of the antibody or antigen-binding fragment thereof is administered to the subject. In different embodiments, more than one dose (e.g., a second dose) of the antibody or antigen-binding fragment thereof is administered to the subject (e.g., two weeks, three weeks, four weeks, or five weeks after administration of the first dose). In some embodiments, the antibody or antigen-binding fragment thereof is administered to the subject for at least one week, 2 weeks, 3 weeks, 1 month, 2 months, 6 months, 1 year, 2 years, or more. In some embodiments, administration of the antibody or antigen-binding fragment thereof reduces proviral DNA in a tissue (e.g., lymph node tissue, gastrointestinal tissue, and/or peripheral blood) of the subject relative to an untreated control, such as to below about 1,000 DNA copies/$10^6$ cells (e.g., below about 100 DNA copies/$10^6$ cells, below about 10 DNA copies/$10^6$ cells, below about 1 DNA copy/$10^6$ cells, or to an undetectable level). In some instances, following administration of the antibody or antigen-binding fragment thereof, the subject has a plasma viral load of less than about 3,500 RNA copies/ml (e.g., less than about 2,000 RNA copies/ml, less than about 400 RNA copies/ml, less than about 50 RNA copies/ml, or less than about 1 RNA copy/ml), or an undetectable plasma viral load. In some instances, following administration of the antibody or antigen-binding fragment thereof, the subject has an undetectable plasma viral load for at least about 2 months (e.g., at least about 6 months, at least about 1 year, or at least about 5 years, or more). In some instances, the administration of the antibody or antigen-binding fragment thereof increases HIV-specific cell-mediated immune response and/or humoral immune response in the subject relative to an untreated control. In additional instances, administration of the antibody or antigen-binding fragment thereof decreases viral replication in the subject relative to an untreated control.

In some embodiments, the antibody or antigen-binding fragment thereof is administered intravenously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. In some instances, the antibody or antigen-binding fragment thereof is administered in combination with one or more immunomodulators (e.g., AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, a gp120-depleted, inactivated $HZ_{321}$ virus (e.g., REMUNE™), CD4 (e.g., recombinant soluble CD4), rCD4-IgG hybrids, SK&F106528 Soluble T4, Thymopentin, Tumor Necrosis Factor, or Infliximab. In added embodiments, the composition further includes at least one reservoir activator, such as a PKC agonist (e.g., a phorbol ester, a macrocyclic lactone such as bryostatin-1, or a diterpene such as an ingenol compound), a cytokine or chemokine (e.g., interleukin (IL)-7, IL-15, or interferon-alpha (IFN-$\alpha$)), a Toll-like receptor (TLR) agonist (e.g., a TLR 1/2 agonist (e.g., Pam3CSK4), a TLR3 agonist (e.g., Poly-ICLC), a TLR5 agonist (e.g., flagellin), a TLR7 agonist (e.g., GS-9620), or a TLR9 agonist (e.g., MGN1703 and CpG7909)), an immune checkpoint inhibitor (e.g., anti-PD-1 monoclonal antibody, an anti-PD-1 ligand (PD-L1) monoclonal antibody, or an anti-CTLA-4 monoclonal antibody), a histone deacetylase (HDAC) inhibitor (e.g., romidepsin, vorinostat, belinostat, LAQ824, panobinostat, entinostat, C1994, or mocetinostat), or a small molecule reservoir activator (e.g., disulfiram, a benzotriazole derivative (e.g., 3-Hydroxy-1,2,3-benzotriazin-4 ((3H)-one (HO-DHBt); a SMAC mimetic), or a BRG-Brahma Associated Factor (BAF) inhibitor (e.g., caffeic acid phenethyl ester or pyrimethamine)). In additional instances, the composition further includes an antiretroviral agent (ARV) (e.g., lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc, raltegravir, ibalizumab, IL-2, IL-12, or alpha-epibromide). In some embodiments, the composition further includes one, two, three, or more different HIV-specific broadly neutralizing antibodies (bnAb), such as a CD4 binding site (CD4bs)-specific antibody (e.g., 3BNC117 or VRC07-523), an N332 glycan-dependent antibody (e.g., PGT121, or a variant thereof; see WO/2015/048770; US 2017/0190763; and U.S. Patent Application No. 62/675,102, which are incorporated herein by reference in entirety), or a V2-specific antibody (e.g., CAP256-VRC26 or the parental PGDM1400; see U.S. Pat. No. 10,093,720 B2; Sok et al., *Proct. Natl. Acad. Sci.* 111:17624-17629, 2014; and Julg et al., *Sci. Transl. Med.* 9: eaal1321, 2017, which are incorporated herein by reference in their entirety). In some embodiments, the reservoir activator, the ARV, and/or the HIV-specific bnAb is/are administered prior to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour prior to), concurrently with and/or after (e.g., about 1 year, 9 months, 6 months, 3 months, 1 month, 3 weeks, 2 weeks, 1 week, 5 days, 3 days, 1 day, 18 hours, 12 hours, 6 hours, or 1 hour after) the administration of the antibody or antigen-binding fragment thereof.

In some embodiments, the methods described herein also includes detection of viral or proviral DNA in blood to assess viral titer, and treatment when results indicate need.

In some embodiments of the above aspect, the subject (e.g., a human) is infected with HIV (e.g., HIV type 1 (HIV-1) and/or HIV type 2 (HIV-2)), or is at risk of HIV transmission (e.g., a fetus of an HIV-infected pregnant female, a newborn having an HIV-infected mother, a subject having a needlestick injury, or a subject being sexually exposed to one or more HIV-infected individuals).

Also featured herein are kits that include the aforementioned PGDM1400 antibody variant or antigen-binding fragment thereof, the polynucleotide encoding the PGDM1400 antibody variant or antigen-binding fragment thereof, the vector containing the polynucleotide, the host cell with the polynucleotide or the vector (e.g., a prokaryotic cell or a eukaryotic cell (e.g., a mammalian cell, such as a CHO or a HEK293 cell)), or the aforementioned composition (e.g., composition containing the aforementioned PGDM1400 antibody variant or antigen-binding fragment thereof, the polynucleotide encoding the antibody or antigen-binding fragment thereof, the vector containing the polynucleotide, or the host cell with the polynucleotide or the vector (e.g., a prokaryotic cell or a eukaryotic cell (e.g., a mammalian cell, such as a CHO or a HEK293 cell)), and, e.g., a pharmaceutically-acceptable carrier, in a therapeutically effective amount for preventing or treating HIV infection (e.g., HIV-1 infection) in a subject (e.g., a human, such as a human infected with HIV). Such kits can include instructions directing a clinician (e.g., a physician or nurse) in methods for administering to the subject the PGDM1400 antibody variant or antigen-binding fragment thereof, the polynucleotide, the vector, the host cell or the composition contained therein.

DEFINITIONS

As used herein, the term "about" refers to a value that is ±10% of the recited value.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and $F(ab')_2$, Fd, Fvs, single-chain Fvs (scFv), rIgG, single-chain antibodies, disulfide-linked Fvs (sdFv), fragments including either a $V_L$ or $V_H$ domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and $F(ab')_2$ fragments) that are capable of specifically binding to a target protein. Fab and $F(ab')_2$ fragments lack the Fc fragment of an intact antibody.

The term "antigen-binding fragment," or "fragments" as used herein, refers to one or more fragments of an immunoglobulin that retain the ability to specifically bind to a target antigen. The antigen-binding function of an immunoglobulin can be performed by fragments of a full-length antibody. The antibody fragments can be a Fab, $F(ab')_2$, scFv, SMIP, diabody, a triabody, an affibody, a NANOBODY™, an aptamer, or a domain antibody. Examples of binding fragments encompassed by the term "antigen-binding fragment" of an antibody include, but are not limited to: (i) a Fab fragment, a monovalent fragment consisting of the $V_L$, $V_H$, $C_L$, and $C_H1$ domains; (ii) a $F(ab')_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb (Ward et al., Nature 341:544-546, 1989) including $V_H$ and $V_L$ domains; (vi) a dAb fragment that consists of a $V_H$ domain; (vii) a dAb that consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv)). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

By "antiretroviral agent" or "ARV" is meant any of the therapeutic agents used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc and raltegravir. ART drugs can also include antibodies, such as ibalizumab, that target HIV proteins or cellular proteins associated with disease progression. Also included are immune-based therapeutic agents, such as IL-2, IL-12, and alpha-epibromide. Each of these drugs can be administered alone or in combination with any other ARV or any HIV-specific neutralizing antibody, such as a broadly neutralizing antibody, e.g., an N332 glycan-dependent antibody (e.g., PGT121, or a variant thereof; see WO/2015/048770; US 2017/0190763; and U.S. Patent Application No. 62/675,102, which are incorporated herein by reference in entirety) or V2-specific antibody (e.g., CAP256-VRC26, PGDM1400, or one or more of the antibody variants, or a fragment thereof, described herein). "Antiretroviral therapy" or "ART" refers to the therapy that uses or involves administration of one or more of these ARVs.

By "reservoir activator" is meant an agent (e.g., a compound, complex, drug, protein, nucleic acid, or pharmaceutical composition) that has the effect of activating a viral reservoir (e.g., an HIV reservoir) or reversing viral latency (e.g., latency of HIV). Reservoir activators are also known in the art as latency reversing agents (LTAs). Examples of reservoir activators are disclosed in Spivak and Planelles (Annu Rev Med, 69:421-436, 2018), Stoszko et al (EBioMedicine, 3:108-121, 2016), and Delagreverie et al (Open Forum Infectious Diseases, DOI: 10.1093/ofid/ofw189); incorporated herein by reference. Exemplary reservoir activators include PKC agonists, cytokines and chemokines, Toll-like receptor (TLR) agonists, immune checkpoint inhibitors, histone deacytelase (HDAC) inhibitors, and dedicated small molecule agents.

As used herein, by "blocking" a retroviral (e.g., human immunodeficiency virus (HIV) (e.g., HIV Type 1 or HIV Type 2)) infection in a subject (e.g., a human, including a human fetus, at risk of retroviral infection) is meant preventing or reducing retroviral establishment and propagation in the subject following exposure to HIV. Blocking an HIV infection may be, in some instances, a means of post-exposure prophylaxis (PEP).

By "broadly neutralizing antibody" or "bnAb," with respect to HIV (e.g., HIV-1), is meant an antibody that recognizes a specific antigen (e.g., gp120 of HIV) and inhibits the effect(s) of the antigen of at least 2, 3, 4, 5, 6, 7, 8, 9 or more different strains of HIV, the strains belonging to the same or different clades, in the host subject (e.g., human). As used herein, the antibody can be a single antibody or a plurality of antibodies.

By "CD4" or "cluster of differentiation 4" is meant an isolated, soluble, or cell surface-attached glycoprotein that is capable of binding and/or forming a complex with gp120. CD4 includes, for example, human CD4 protein (NCBI RefSeq No. NP_000607.1).

As used herein, by "CD4 binding site-specific antibody" or "CD4bs-specific antibody" is meant an antibody, or antibody fragment thereof, that specifically binds to gp120 of HIV (e.g., HIV Type 1 or HIV Type 2) at an epitope that overlaps partially or completely with that recognized by CD4, and/or that competes with CD4 for binding to gp120 of HIV. Examples of CD4bs-specific antibodies include 3BNC117 (Scheid et al., *Nature.* 458: 636-640, 2009), b12 (Roben et al., *J Virol.* 68: 4821-4828, 1994), and the other antibodies disclosed at Table 1 of U.S. Pub. No. 2012/0288502, which is incorporated herein by reference in its entirety.

As used herein, the term "clade" refers to related human immunodeficiency viruses (HIVs) classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, methods of the invention as described herein can be used to cure a subject (e.g., a human) infected with HIV (e.g., HIV-1) or to block HIV (e.g., HIV-1) infection in subject (e.g., a human) at risk of HIV transmission. The HIV may be of two, three, four, five, six, seven, eight, nine, ten, or more clades and/or two or more groups of HIV.

As used herein, the term "complementarity determining regions" or "CDRs" refers to the amino acid residues of an antibody variable domain that is involved in antigen binding. Each variable domain typically has three CDR regions identified as CDR-1, CDR-2 and CDR-3. Each complementarity determining region may comprise amino acid residues from a "complementarity determining region" as defined by Kabat (i.e., about residues 24-34 (CDR-L1), 50-56 (CDR-L2) and 89-97 (CDR-L3) in the light chain variable domain and about residues 31-35 (CDR-H1), 50-65 (CDR-H2) and 95-102 (CDR-H3) in the heavy chain variable domain; Kabat et al. *Sequences of Proteins of Immunological Interest,* 5th Ed. Public Health Service, National Institutes of Health, Bethesda, Md. (1991)) and/or those residues from a "hypervariable loop" (i.e., about residues 26-32 (CDR-L1), 50-52 (CDR-L2) and 91-96 (CDR-L3) in the light chain variable domain and about residues 26-32 (CDR-H1), 53-55 (CDR-H2) and 96-101 (CDR-H3) in the heavy chain variable domain; Chothia and Lesk, *J. Mol. Biol.* 196:901-917 (1987)). In some instances, a complementarity determining region can include amino acids from both a CDR region defined according to Kabat and a hypervariable loop.

Throughout this specification and claims, the terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is, therefore, interpreted to be an open term meaning "at least the following," and is also interpreted not to exclude additional features, limitations, aspects, etc. Thus, for example, "a process involving steps a, b, and c" means that the process includes at least steps a, b and c.

Wherever the terms "a" or "an" are used, "one or more" is understood, unless such interpretation is nonsensical in context.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into the gp120 and gp41 envelope (Env) proteins. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

The terms "human immunodeficiency virus" or "HIV," as used herein, refer generally to a retrovirus that is the causative agent for acquired immunodeficiency syndrome (AIDS), variants thereof, and diseases, conditions, or opportunistic infections associated with AIDS or its variants, and includes HIV-Type 1 (HIV-1) and HIV-Type 2 (HIV-2) of any clade or strain therein, related retroviruses, and variants thereof (e.g., engineered retroviruses, e.g., chimeric HIV viruses). Previous names for HIV include human T-lymphotropic virus-Ill (HTLV-III), lymphadenopathy-associated virus (LAV), and AIDS-associated retrovirus (ARV).

By "immunomodulator" is meant an agent, such as a protein or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Examples of immunomodulators include those disclosed at Table 1 of WO 01/38332, which is incorporated herein by reference in its entirety. An immunomodulator may be administered in conjunction with (e.g., prior to, concurrently with, or subsequent to, or within the context of a treatment regimen that includes the administration of an antibody or antigen-binding fragment thereof described herein (e.g., one or more of the PGDM1400 variant antibodies described herein).

As used herein, by "V2-specific antibody" is meant an antibody, or antibody fragment thereof, that specifically binds to the V2 apex antigenic region of the HIV Env trimer (e.g., HIV Type 1 or HIV Type 2) for specific recognition of HIV. These antibodies bind to the intact trimer with a stoichiometry of one per trimer and interact with glycans at position N160 and, to a lesser extent, N156. They also have a very long heavy-chain complementarity-determining region 3 (CDR-H3), which allows them to effectively penetrate the glycan shield (Julg et al., *Sci Transl. Med.* 9: eaal1321, 2017; incorporated herein by reference in entirety). V2-specific antibody specifically includes CAP256-VRC26, the parental PGDM1400, and one or more of the PGDM1400 variant antibodies and fragments thereof described herein.

As used herein, by "parental PGDM1400" is meant an antibody or fragment thereof that includes the following six complementarity determining regions (CDRs): a heavy chain (HC)-CDR1 with the amino acid sequence of SEQ ID NO: 12, a HC-CDR2 with the amino acid sequence of SEQ ID NO: 14, a HC-CDR3 with the amino acid sequence of SEQ ID NO: 16, a light chain (LC)-CDR1 with the amino acid sequence of SEQ ID NO: 4, a LC-CDR2 with the amino acid sequence of SEQ ID NO: 6, a LC-CDR3 with the amino acid sequence of SEQ ID NO: 8, a heavy chain variable domain having the sequence of SEQ ID NO: 136 or amino acids 20-490 of SEQ ID NO: 10, and a light chain variable domain having the sequence of SEQ ID NO: 135 or amino acids 20-238 of SEQ ID NO: 2. The HC-CDR1, the HC-CDR2, the HC-CDR3, the LC-CDR1, the LC-CDR2, the LC-CDR3, the heavy chain variable domain, and the light chain variable domain of the parental PGDM1400 or antigen-binding fragment thereof are encoded by the nucleotide sequences of SEQ ID NOs: 11, 13, 15, 3, 5, 7, 9, and 1, respectively. Parental PGDM1400 has been described in U.S. Pat. No. 10,093,720 B2; Sok et al., *Proct. Natl, Acad, Sci.* 111: 17624-17629, 2014; and Julg et al., *Sci. Transl. Med.* 9: eaal1321, 2017, which are incorporated herein by reference in their entirety.

As used herein, by "N332 glycan-dependent antibody" is meant an antibody, or antibody fragment thereof, that specifically binds to gp120 of HIV (e.g., HIV Type 1 or HIV Type 2) at residue N332 when the residue contains a glycan for specific recognition of HIV, and specifically includes PGT family antibodies (e.g., PGT121, or a variant thereof disclosed in WO/2015/048770; US 2017/0190763; and U.S. Patent Application No. 62/675,102, which are incorporated herein by reference in entirety).

As used herein, by "PGT family antibody" is meant an antibody, or antibody fragment thereof, including PGT121 and PGT121 derivatives and clonal relatives thereof (e.g., antibody 10-1074), such as those disclosed in WO 2012/030904; WO 2013/055908; Walker et al. *Nature.* 477: 466-470, 2011; Mouquet et al. *Proc. Natl. Acad. Sci.* 109(47): E3268-E3277, 2012; Julien et al., *PLoS Pathog.* 9: e1003342, 2013; and Kong et al., *Nat. Struc. Mol. Biol.* 20: 796-803, 2013, which are incorporated herein by reference in their entirety.

By "needlestick injury" is meant any wound of any size caused by a needle that intentionally or accidentally punctures the skin.

The term "plasma viral load," as used herein, means the amount of HIV in the circulating blood of a mammal, such as a human. The amount of HIV in the blood of a mammal can be determined by measuring the quantity of HIV RNA copies in the blood using methods known to those of ordinary skill in the art.

By "pharmaceutical composition" is meant a composition containing a compound described herein (e.g., one or more of the PGDM1400 variant antibodies described herein) that can be formulated, for example, for intravenous administration (e.g., as a sterile solution free of particulate emboli and in a solvent system suitable for intravenous use); for oral administration in unit dosage form (e.g., a tablet, capsule, caplet, gelcap, or syrup); for topical administration (e.g., as a cream, gel, lotion, or ointment); or in any other formulation described herein.

A "pharmaceutically acceptable carrier" is meant a carrier which is physiologically acceptable to a mammal (e.g., a human) while retaining the therapeutic properties of the compound (e.g., one or more of the PGDM1400 variant antibodies described herein) with which it is administered. One exemplary pharmaceutically acceptable carrier is physiological saline. Other physiologically acceptable carriers and their formulations are known to one skilled in the art and described, for example, in *Remington's Pharmaceutical Sciences* (18th edition, A. Gennaro, 1990, Mack Publishing Company, Easton, PA), incorporated herein by reference.

By "proviral DNA" is meant viral (e.g., retroviral, e.g., HIV, e.g., HIV-1) genomic DNA that is integrated into the DNA of a host cell, such as a tissue cell (e.g., a lymph node, gastrointestinal, or peripheral blood tissue cell).

As used herein, the term "reduce" with respect to proviral DNA level in tissue of a subject refers to a decrease of proviral DNA level by about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more in a subject administered one or more of the PGDM1400 variant antibodies described herein, as compared to that of a control subject (e.g., a subject not administered one or more of the PGDM1400 variant antibodies described herein) or a subject administered a placebo). Administration of one or more of the PGDM1400 variant antibodies described herein, or a fragment thereof, may, for example, result in a decrease in proviral DNA level in tissue to below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells).

The term "retrovirus," as used herein, refers to a virus belonging to the viral family Retroviridae, which includes viruses that possess an RNA genome, and that replicate via a DNA intermediate.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q −1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid or nucleotide residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For polypeptides, the length of comparison sequences will generally be at least 5, 6, 7, 8, 9, 10, 11, 12, 13, 14, 15, 16, 17, 18, 19, 20, 25, 50, 75, 90, 100, 110, 120, 130, 140, or 150 or more contiguous amino acids.

By "specifically binds" is meant the preferential association of an antibody, or fragment thereof, to a target molecule (e.g., a viral protein, e.g., gp120, e.g., the V2 apex antigenic region of gp120) in a sample (e.g., a biological sample) or in vivo or ex vivo. It is recognized that a certain degree of non-specific interaction may occur between an antibody and a non-target molecule. Nevertheless, specific binding may be distinguished as mediated through specific recognition of the target molecule. Specific binding results in a stronger association between the antibody, or fragment thereof, and, e.g., an antigen (e.g., gp120, e.g., the N160 glycan of the V2 apex antigenic region of gp120) than between the antibody and, e.g., a non-target molecule (e.g., non-viral polypeptide). In one example, the antibody may specifically bind to the N160 glycan of envelope glycoprotein gp120 of HIV. In another example, the antibody may specifically bind to the CD4 binding site (CD4bs) of envelope glycoprotein gp120 of HIV. The antibody (e.g., one or more of the PGDM1400 variant antibodies described herein) may have, e.g., at least about 2-fold greater affinity (e.g., about 2, 3, 4, 5, 6, 7, 8, 9, 10, $10^2$-, $10^3$-, $10^4$-, $10^5$-, $10^6$-, $10^7$-, $10^8$-, $10^9$-, or $10^{10}$-fold greater affinity) to the gp120 protein than to other viral or non-viral polypeptides (e.g., one or more of the PGDM1400 variant antibodies described herein has at least 2-fold greater affinity to gp120 than a comparable IgG antibody).

A "subject" is a mammal, such as a human. Mammals also include, but are not limited to, primates (e.g., monkeys, e.g., rhesus monkeys) farm animals (e.g., cows), sport animals (e.g., horses), pets (e.g., cats and dogs), mice, rats, rabbits, and guinea pigs.

As used herein, and as well understood in the art, "treatment" is an approach for obtaining beneficial or desired results, such as clinical results. Beneficial or desired results can include, but are not limited to, cure or eradication of disease, disorder, or condition (e.g., HIV infection); alleviation or amelioration of one or more symptoms or conditions (e.g., HIV infection); diminishment of extent of disease, disorder, or condition (e.g., HIV infection); stabilization (i.e., not worsening) of a state of disease, disorder, or condition (e.g., HIV infection); prevention or reduction of spread or transmission of disease, disorder, or condition (e.g., HIV infection); delay or slowing the progress of the disease (e.g., by about 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more), disorder, or condition (e.g., HIV infection); amelioration or palliation of the disease, disorder, or condition (e.g., HIV infection); and remission (whether partial or total), whether detectable or undetectable (e.g., undetectable for a length of time, such as for over about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more).

As used herein, by "treating" a subject (e.g., a human) infected with a retrovirus (e.g., HIV-1 or HIV-2) is meant obtaining and maintaining virologic control, e.g., in the absence of an ART, for a period of at least about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more.

"Cure," as used herein, can refer to one or more of the following: (i) sterilizing cure, e.g., in which virus is killed to undetectable levels in a subject (e.g., a human), (ii) functional cure, in which viral load is undetectable in a subject (e.g., a human) without ART, and/or (iii) reduction of viral reservoirs (e.g., partial reduction of viral reservoirs, in which the infection is not reduced to undetectable levels in the subject, for example, in which the subject shows undetectable plasma load but detectable proviral DNA) in a subject (e.g., a human) for a period of at least about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more. In an embodiment, "cure" means killing the virus to undetectable levels in a subject (e.g., a human), as determined by methods well known in the art.

As used herein, "storage stability" refers to the stability of a compound, such as a protein (e.g., an antibody, such as one or more of the PGDM1400 variant antibodies or antigen-binding fragments thereof described herein) over extended periods. Therapeutic proteins (e.g., therapeutic antibodies) with storage stability have longer shelf lives and are resistant to degradation over time. Proteins (e.g., antibodies) in solution can degrade by means of several mechanisms during extended storage, and a common degradation route is aggregation of the protein over time. Storage stability is a factor in determining pharmaceutical success of therapeutic proteins antibodies (e.g., therapeutic antibodies). Hence, biopharmaceutical developers aim to create liquid biopharmaceutical formulations (e.g., liquid formulations of antibodies) with long shelf lives and resistance to the formation of aggregates. Proteins (e.g., antibodies) with storage stability are resistant to aggregation over time (e.g., over about 2 days, 3 days, 4 days, 5 days, 6 days, 1 week, 2 weeks, 3 weeks, 1 month, 2 months, 3 months, 4 months, 5 months, 6 months, 1 year, 2 years, 3 years, 4 years, 5 years, or more at a temperature of about −20° C. to about 25° C. (e.g., about −30° C., −25° C., −20° C., −15° C., −10° C., −5° C., 0° C., 5° C., 10° C., 15° C., 20° C., 25° C., 30° C., or 35° C.)), and, thus, are suitable for extended storage and safe therapeutic application.

As used herein, "manufacturability" refers to ease of manufacture of proteins (e.g., therapeutic proteins such as antibodies) is determined by design and biophysical properties of the protein that contribute to easy and successful manufacture of the same. Manufacturability of protein (e.g., antibody) is determined by stability at low pH, intramolecular stability, thermodynamic stability, and resistance to aggregation. Proteins (e.g., therapeutic proteins such as antibodies) are exposed to a wide range of non-physiological processes and conditions during production (including variations of temperature, pH, protein concentrations, ionic strength, exposure to air-water interfaces and mechanical stress) that can dramatically increase their propensity to aggregate. Resistance to aggregation and/or reduced aggregation of proteins ensures ease of manufacture or manufacturability. Thus, successful production of a protein therapeutic (e.g., antibodies) requires balancing the potency and pharmacokinetics of the candidate therapeutic with its manufacturing capability or manufacturability.

As used herein, "variable domain" of an antibody, or fragment thereof, refers to the portions of the light and heavy chains of antibody molecules that include amino acid sequences of complementarity determining regions (CDRs; i.e., CDR-1, CDR-2, and CDR-3, e.g., CDR-H1, CDR-H2, CDR-H3, CDR-L1, CDR-L2, and CDR-L3), and surrounding framework regions (FRs). VH refers to the variable domain of the heavy chain. VL refers to the variable domain of the light chain. The amino acid residues assigned to CDRs are defined according to Kabat (*Sequences of Proteins of Immunological Interest,* 5th Ed. Public Health Service, National Institutes of Health, Bethesda, Md. (1991)). Amino acid numbering of antibodies or antigen binding fragments is also according to that of Kabat.

As used herein, the term "virologic control" is meant a condition characterized by undetectable proviral DNA level in tissue (e.g., lymph node tissue, gastrointestinal tissue, and/or peripheral blood), such as below about 1,000 DNA copies/$10^6$ cells (e.g., below about 100 DNA copies/$10^6$ cells, below about 10 DNA copies/$10^6$ cells, or below about 1 DNA copy/$10^6$ cells), and/or undetectable plasma viral load, such as less than about 3,500 RNA copies/ml (e.g., less than about 2,000 RNA copies/ml, less than about 400 RNA copies/ml, less than about 50 RNA copies/ml, or less than about 1 RNA copy/ml).

The term "virus," as used herein, is defined as an infectious agent that is unable to grow or reproduce outside a host cell (e.g., a mammalian cell) and that infects an animal (e.g., a mammal, such as a human).

BRIEF DESCRIPTION OF DRAWINGS

FIG. 2 is a mutation grid showing substitution of different amino acid residues on the heavy and light chain variable domains of the Round 1 PGDM1400 antibody variants.

FIG. 3 is a mutation grid showing substitution of different amino acid residues on the light chain variable domain of the Round 2 PGDM1400 antibody variants.

DETAILED DESCRIPTION OF THE INVENTION

Figure 1:
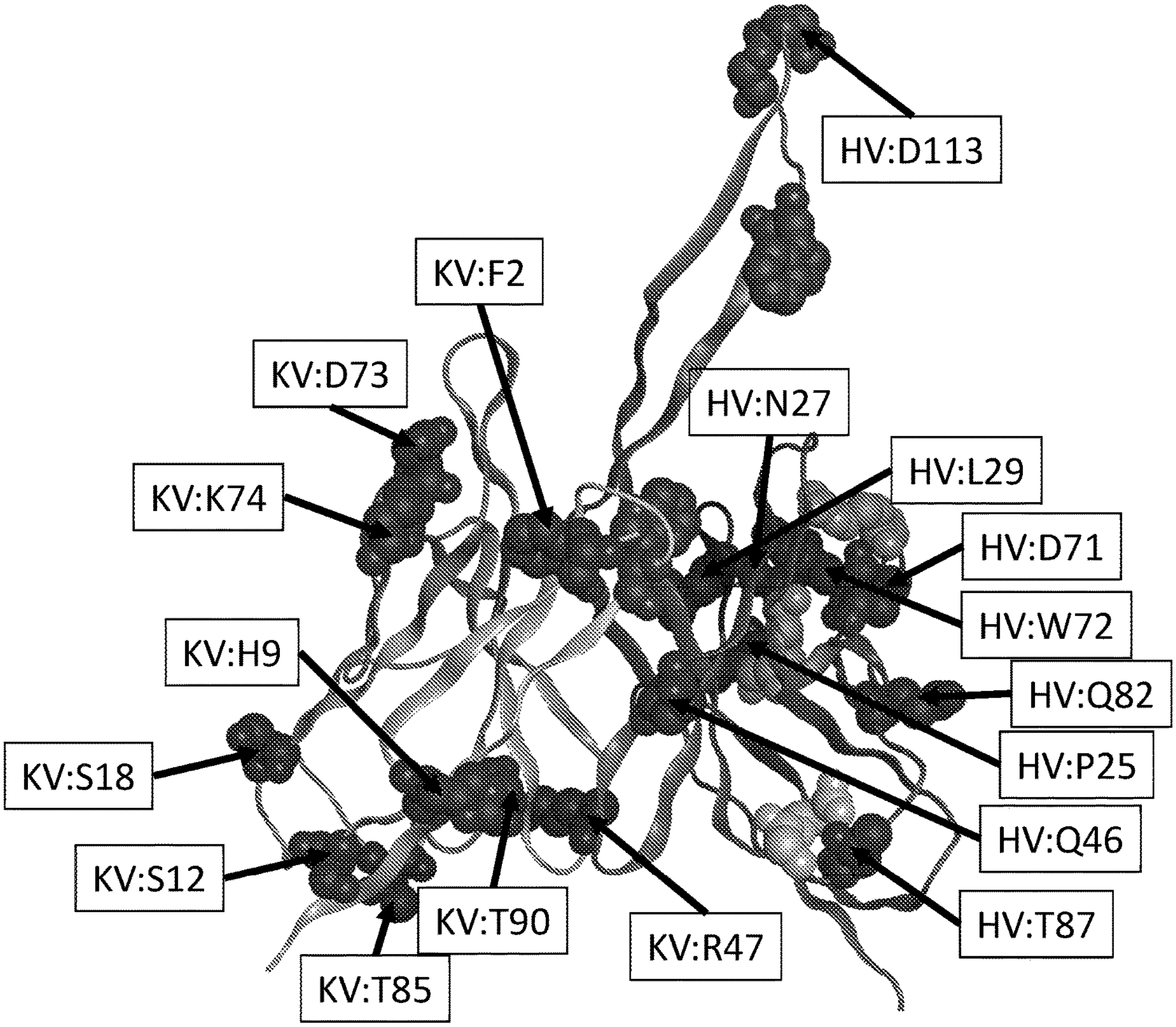
FIG. 1 is a schematic representation of the residues modified in the parental PGDM1400 antibody to produce the PGDM1400 antibody variants described herein.

We have identified and mutated potentially destabilizing residues in the variable domain (Fv) of the PGDM1400 antibody. These residues of the antibody, by themselves or in combination, may lead to instability at low pH, increased susceptibility to chemical degradation, or aggregation during production or long term storage. Based on our discovery, we generated a series of antibody variants with mutations of one or more of the destabilizing residues. The antibody variants produced by such combinatorial residue replacement techniques retained potency (e.g., viral inactivation or neutralization potency) while exhibiting desired biophysical characteristics, in particular, increased stability at low pH, reduced susceptibility to chemical degradation, and reduced aggregation. Featured herein are PGDM1400 variant antibodies and antigen-binding fragments thereof that retain the ability of the native PGDM1400 antibody to inactivate or neutralize viruses (e.g., HIV-1), while showing significant improvement in production efficiency (e.g., increased production titer), manufacturability, and storage stability relative to the native PGDM1400 antibody.

I. Antibodies and Antigen-Binding Fragments Thereof

Featured are PGDM1400 variant antibodies and antigen-binding fragments thereof that exhibit improved properties. The PGDM1400 variant antibodies or fragment thereof contain: (a) a heavy chain variable domain having a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 136; and (b) a light chain variable domain having a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 135; and wherein the antibody or antigen-binding fragment thereof has: (i) at least one of the following mutations in the heavy chain variable domain sequence: HV:P25S, HV:N27Y, HV:L29F, HV:Q46E, HV:D71T, HV:W72R, HV:Q82E, HV:T87R, and HV:D113E; and/or (ii) at least one of the following mutations in the light chain variable domain sequence: KV:F2I, KV:H9L, KV:S12P, KV:S18P, KV:R47Q, KV:D73G, KV:K74T, KV:T85A, and KV:T90V.

For example, the PGDM1400 variant antibody or fragment thereof may contain (i) a heavy chain variable domain having a sequence with at least 85% sequence identity to SEQ ID NO: 136; and (ii) a light chain variable domain having a sequence with at least 85% sequence identity to SEQ ID NO: 135, and at least one (e.g., at least one, at least two, at least three, at least four, at least five, at least six, or more) of the following mutations in the light chain variable domain: KV:F2I, KV:H9L, KV:S12P, KV:S18P, KV:R47Q, KV:D73G, KV:K74T, KV:T85A, and KV:T90V. Alternatively, the PGDM1400 variant antibody or fragment thereof may have (i) a heavy chain variable domain having a sequence with at least 85% sequence identity to SEQ ID NO: 136, and at least one (e.g., at least one, at least two, at least three, at least four, at least five, at least six, or more) of the following mutations in the heavy chain variable domain: HV:P25S, HV:N27Y, HV:L29F, HV:Q46E, HV:D71T, HV:W72R, HV:Q82E, HV:T87R, and HV:D113E; and (ii) a light chain variable domain having a sequence with at least 85% sequence identity to SEQ ID NO: 135. In some embodiments, the PGDM1400 variant antibody or fragment thereof may have (i) a heavy chain variable domain having a sequence with at least 85% sequence identity to SEQ ID NO: 136, and at least one (e.g., at least one, at least two, at least three, at least four, at least five, at least six, or more) of the following mutations in the heavy chain variable domain: HV:P25S, HV:N27Y, HV:L29F, HV:Q46E, HV:D71T, HV:W72R, HV:Q82E, HV:T87R, and HV:D113E; and (ii) a light chain variable domain having a sequence with at least 85% sequence identity to SEQ ID NO: 135, and at least one (e.g., at least one, at least two, at least three, at least four, at least five, at least six, or more) of the following mutations in the light chain variable domain: KV:F2I, KV:H9L, KV:S12P, KV:S18P, KV:R47Q, KV:D73G, KV:K74T, KV:T85A, and KV:T90V. In other embodiments, the PGDM1400 variant antibody or fragment thereof may have (i) a heavy chain variable domain having a sequence with at least 85% sequence identity to SEQ ID NO: 136; (ii) a light chain variable domain having a sequence with at least 85% sequence identity to SEQ ID NO: 135; (iii) at least one (e.g., at least one, at least two, at least three, at least four, at least five, at least six, or more) of the following mutations in the heavy chain variable domain: HV:P25S, HV:N27Y, HV:L29F, HV:Q46E, HV:D71T, HV:W72R, HV:Q82E, HV:T87R, and HV:D113E; and (iv) at least one (e.g., at least one, at least two, at least three, at least four, at least five, at least six, or more) of the following mutations in the light chain variable domain: KV:F2I, KV:H9L, KV:S12P, KV:S18P, KV:R47Q, KV:D73G, KV:K74T, KV:T85A, and KV:T90V. Alternatively, the PGDM1400 variant antibody or fragment thereof may contain (i) a heavy chain variable domain having a sequence with at least 85% sequence identity to SEQ ID NO: 136; and (ii) a light chain variable domain having a sequence with at least 85% sequence identity to SEQ ID NO: 135.

In some embodiments, the PGDM1400 variant antibody or fragment thereof may have (i) a heavy chain variable domain having a sequence with at least 85% sequence identity to SEQ ID NO: 136; (ii) a light chain variable domain having a sequence with at least 85% sequence identity to SEQ ID NO: 135; and (iii) a KV:F2I mutation in the light chain variable domain. Such a PGDM1400 variant antibody or fragment thereof may further comprise: at least one (e.g., at least one, at least two, at least three, at least four, at least five, at least six, or more) of the following mutations in the heavy chain variable domain: HV:P25S, HV:N27Y, HV:L29F, HV:Q46E, HV:D71T, HV:W72R, HV:Q82E, HV:T87R, and HV:D113E; and/or at least one (e.g., at least one, at least two, at least three, at least four, at least five, at least six, or more) of the following mutations in the light chain variable domain: KV:H9L, KV:S12P, KV:S18P, KV:R47Q, KV:D73G, KV:K74T, KV:T85A, and KV:T90V.

The Fc domain of any of the PGDM1400 variant antibodies or fragments thereof described herein may include the sequence of SEQ ID NO: 137, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 137. Alternatively, the Fc domain of any of the PGDM1400 variant antibodies or fragments thereof described herein may include the sequence of SEQ ID NO: 138, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 138. Preferentially, the Fc domain of the PGDM1400 variant antibody or fragment thereof includes the sequence of SEQ ID NO: 138, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 138. Alternatively, the Fc domain of the PGDM1400 variant antibody or fragment thereof may include a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 137, and a M87L and/or a N93S mutation. The Fc domain of any of the PGDM1400 variant antibodies or fragments thereof described herein may further include the sequence of SEQ ID NO: 139, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 139. Together, the Fc domain of any of the PGDM1400 variant antibodies or fragments thereof described herein may have: (i) the sequence of SEQ ID NO: 140, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 140; or (ii) the sequence of SEQ ID NO: 141, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 141.

The featured PGDM1400 variant antibody or fragment thereof may further include an Ig domain with the sequence of SEQ ID NO: 142, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 142. Additionally, the antibody or antigen-binding fragment thereof described herein may further include a Hinge region with the sequence of SEQ ID NO: 143, or a sequence with at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity to SEQ ID NO: 143.

In specific embodiments:

(a) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 144 or amino acids 20-238 of SEQ ID NO: 18. The antibody or antigen-binding fragment thereof has M87L and N93S mutations in the heavy chain Fc region, and a KV:F2I mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 17, respectively;

(b) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 145 or amino acids 20-238 of SEQ ID NO: 20. The antibody or antigen-binding fragment thereof has M87L and N93S mutations in the heavy chain Fc region, and a KV:H9L mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 19, respectively;

(c) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 146 or amino acids 20-238 of SEQ ID NO: 22. The antibody or antigen-binding fragment thereof has M87L and N93S mutations in the heavy chain Fc region, and a KV:S12P mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 21, respectively;

(d) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 147 or amino acids 20-238 of SEQ ID NO: 24. The antibody or antigen-binding fragment thereof has M87L and N93S mutations in the heavy chain Fc region, and a KV:S18P mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 23, respectively;

(e) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 148 or amino acids 20-238 of SEQ ID NO: 26. The antibody or antigen-binding fragment thereof has M87L and N93S mutations in the heavy chain Fc region, and a KV:R47Q mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 25, respectively;

(f) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 149 or amino acids 20-238 of SEQ ID NO: 28. The antibody or antigen-binding fragment thereof has M87L and N93S mutations in the heavy chain Fc region, and a KV:D73G mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 27, respectively;

(g) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 150 or amino acids 20-238 of SEQ ID NO: 30. The antibody or antigen-binding fragment thereof has M87L and N93S mutations in the heavy chain Fc region, and a KV:K74T mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 29, respectively;

(h) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 151 or amino acids 20-238 of SEQ ID NO: 32. The antibody or antigen-binding fragment thereof has M87L and N93S mutations in the heavy chain Fc region, and a KV:T85A mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 31, respectively;

(i) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 152 or amino acids 20-238 of SEQ ID NO: 34. The antibody or antigen-binding fragment thereof has M87L and N93S mutations in the heavy chain Fc region, and a KV:T90V mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 33, respectively;

(j) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 153 or amino acids 20-490 of SEQ ID NO: 36, and a light chain variable domain having the sequence of SEQ ID NO: 135 or amino acids 20-238 of SEQ ID NO: 2. The antibody or antigen-binding fragment thereof has a HV:P25S mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC- CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 35, and 1, respectively;

(k) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 154 or amino acids 20-490 of SEQ ID NO: 38, and a light chain variable domain having the sequence of SEQ ID NO: 135 or amino acids 20-238 of SEQ ID NO: 2. The antibody or antigen-binding fragment thereof has a HV:N27Y mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 37, and 1, respectively;

(l) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 155 or amino acids 20-490 of SEQ ID NO: 40, and a light chain variable domain having the sequence of SEQ ID NO: 135 or amino acids 20-238 of SEQ ID NO: 2. The antibody or antigen-binding fragment thereof has a HV:L29F mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 39, and 1, respectively;

(m) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 156 or amino acids 20-490 of SEQ ID NO: 42, and a light chain variable domain having the sequence of SEQ ID NO: 135 or amino acids 20-238 of SEQ ID NO: 2. The antibody or antigen-binding fragment thereof has a HV:Q46E mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 41, and 1, respectively;

(n) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 157 or amino acids 20-490 of SEQ ID NO: 44, and a light chain variable domain having the sequence of SEQ ID NO: 135 or amino acids 20-238 of SEQ ID NO: 2. The antibody or antigen-binding fragment thereof has a HV:D71T mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 43, and 1, respectively;

(o) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 158 or amino acids 20-490 of SEQ ID NO: 46, and a light chain variable domain having the sequence of SEQ ID NO: 135 or amino acids 20-238 of SEQ ID NO: 2. The antibody or antigen-binding fragment thereof has a HV:W72R mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 45, and 1, respectively;

(p) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 159 or amino acids 20-490 of SEQ ID NO: 48, and a light chain variable domain having the sequence of SEQ ID NO: 135 or amino acids 20-238 of SEQ ID NO: 2. The antibody or antigen-binding fragment thereof has a HV:Q82E mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 47, and 1, respectively;

(q) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 160 or amino acids 20-490 of SEQ ID NO: 50, and a light chain variable domain having the sequence of SEQ ID NO: 135 or amino acids 20-238 of SEQ ID NO: 2. The antibody or antigen-binding fragment thereof has a HV:T87R mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 49, and 1, respectively;

(r) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 54, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 54; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 161 or amino acids 20-490 of SEQ ID NO: 52, and a light chain variable domain having the sequence of SEQ ID NO: 135 or amino acids 20-238 of SEQ ID NO: 2. The antibody or antigen-binding fragment thereof has a HV:D113E mutation in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 53, 3, 5, 7, 51, and 1, respectively;

(s) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 163 or amino acids 20-490 of SEQ ID NO: 58, and a light chain variable domain having the sequence of SEQ ID NO: 162 or amino acids 20-238 of SEQ ID NO: 56. The antibody or antigen-binding fragment thereof has a HV:T87R mutation in the heavy chain variable domain, M87L and N93S mutations in the heavy chain Fc region, and KV:H9L, KV:S12P, KV:S18P, KV:R47Q, KV:T85A and KV:T90V mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 57, and 55, respectively;

(t) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 164 or amino acids 20-238 of SEQ ID NO: 60. The antibody or antigen-binding fragment thereof has M87L and N93S mutations in the heavy chain Fc region, and KV:F2I, KV:D73G and KV:K74T mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 59, respectively;

(u) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 165 or amino acids 20-490 of SEQ ID NO: 62, and a light chain variable domain having the sequence of SEQ ID NO: 135 or amino acids 20-238 of SEQ ID NO: 2. The antibody or antigen-binding fragment thereof has HV:P25S, HV:N27Y and HV:L29F mutations in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 61, and 1, respectively;

(v) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 166 or amino acids 20-490 of SEQ ID NO: 64, and a light chain variable domain having the sequence of SEQ ID NO: 135 or amino acids 20-238 of SEQ ID NO: 2. The antibody or antigen-binding fragment thereof has HV:D71T and HV:W72R mutations in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 63, and 1, respectively;

(w) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 167 or amino acids 20-490 of SEQ ID NO: 66, and a light chain variable domain having the sequence of SEQ ID NO: 135 or amino acids 20-238 of SEQ ID NO: 2. The antibody or antigen-binding fragment thereof has HV:P25S, HV:N27Y, HV:L29F, HV:D71T and HV:W72R mutations in the heavy chain variable domain, and M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 65, and 1, respectively;

(x) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 169 or amino acids 20-490 of SEQ ID NO: 70, and a light chain variable domain having the sequence of SEQ ID NO: 168 or amino acids 20-238 of SEQ ID NO: 68. The antibody or antigen-binding fragment thereof has HV:N27Y and HV:D71T mutations in the heavy chain variable domain, M87L and N93S mutations in the heavy chain Fc region, and a KV:H9L mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 69, and 67, respectively;

(y) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 171 or amino acids 20-490 of SEQ ID NO: 74, and a light chain variable domain having the sequence of SEQ ID NO: 170 or amino acids 20-238 of SEQ ID NO: 72. The antibody or antigen-binding fragment thereof has HV:P25S, HV:N27Y and HV:L29F mutations in the heavy chain variable domain, M87L and N93S mutations in the heavy chain Fc region, and a KV:H9L mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 73, and 71, respectively;

(z) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 173 or amino acids 20-490 of SEQ ID NO: 78, and a light chain variable domain having the sequence of SEQ ID NO: 172 or amino acids 20-238 of SEQ ID NO: 76. The antibody or antigen-binding fragment thereof has HV:P25S and HV:N27Y mutations in the heavy chain variable domain, M87L and N93S mutations in the heavy chain Fc region, and KV:H9L and KV:K74T mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 77, and 75, respectively;

(aa) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; tor (ii) a heavy chain variable domain having the sequence of SEQ ID NO: 175 or amino acids 20-490 of SEQ ID NO: 82, and a light chain variable domain having the sequence of SEQ ID NO: 174 or amino acids 20-238 of SEQ ID NO: 80. The antibody or antigen-binding fragment thereof has HV:Q46E, HV:W72R and HV:T87R mutations in the heavy chain variable domain, M87L and N93S mutations in the heavy chain Fc region, and a KV:F2I mutation in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 81, and 79, respectively;

(bb) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 135 or amino acids 20-238 of SEQ ID NO: 2. The antibody or antigen-binding fragment thereof has M87L and N93S mutations in the heavy chain Fc region. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 1, respectively;

(cc) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 176 or amino acids 20-238 of SEQ ID NO: 84. The antibody or antigen-binding fragment thereof has M87L and N93S mutations in the heavy chain Fc region, and KV:F2I and KV:H9L mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 83, respectively;

(dd) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 177 or amino acids 20-238 of SEQ ID NO: 86. The antibody or antigen-binding fragment thereof has M87L and N93S mutations in the heavy chain Fc region, and KV:F2I and KV:S18P mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 85, respectively;

(ee) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 178 or amino acids 20-238 of SEQ ID NO: 88. The antibody or antigen-binding fragment thereof has M87L and N93S mutations in the heavy chain Fc region, and KV:F2I and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 87, respectively;

(ff) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 179 or amino acids 20-238 of SEQ ID NO: 90. The antibody or antigen-binding fragment thereof has M87L and N93S mutations in the heavy chain Fc region, and KV:F2I and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 89, respectively;

(gg) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 180 or amino acids 20-238 of SEQ ID NO: 92. The antibody or antigen-binding fragment thereof has M87L and N93S mutations in the heavy chain Fc region, and KV:H9L and KV:S18P mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 91, respectively;

(hh) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 181 or amino acids 20-238 of SEQ ID NO: 94. The antibody or antigen-binding fragment thereof has M87L and N93S mutations in the heavy chain Fc region, and KV:H9L and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 93, respectively;

(ii) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 182 or amino acids 20-238 of SEQ ID NO: 96. The antibody or antigen-binding fragment thereof has M87L and N93S mutations in the heavy chain Fc region, and KV:H9L and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 95, respectively;

(jj) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 183 or amino acids 20-238 of SEQ ID NO: 98. The antibody or antigen-binding fragment thereof has M87L and N93S mutations in the heavy chain Fc region, and KV:S18P and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 97, respectively;

(kk) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 184 or amino acids 20-238 of SEQ ID NO: 100. The antibody or antigen-binding fragment thereof has M87L and N93S mutations in the heavy chain Fc region, and KV:S18P and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 99, respectively;

(ll) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 185 or amino acids 20-238 of SEQ ID NO: 102. The antibody or antigen-binding fragment thereof has M87L and N93S mutations in the heavy chain Fc region, and KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 101, respectively;

(mm) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 186 or amino acids 20-238 of SEQ ID NO: 104. The antibody or antigen-binding fragment thereof has M87L and N93S mutations in the heavy chain Fc region, and KV:F2I, KV:H9L and KV:S18P mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 103, respectively;

(nn) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 187 or amino acids 20-238 of SEQ ID NO: 106. The antibody or antigen-binding fragment thereof has M87L and N93S mutations in the heavy chain Fc region, and KV:F2I, KV:H9L and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 105, respectively;

(oo) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 188 or amino acids 20-238 of SEQ ID NO: 108. The antibody or antigen-binding fragment thereof has M87L and N93S mutations in the heavy chain Fc region, and KV:F2I, KV:H9L and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 107, respectively;

(pp) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 189 or amino acids 20-238 of SEQ ID NO: 110. The antibody or antigen-binding fragment thereof has M87L and N93S mutations in the heavy chain Fc region, and KV:F2I, KV:S18P and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 109, respectively;

(qq) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 190 or amino acids 20-238 of SEQ ID NO: 112. The antibody or antigen-binding fragment thereof has M87L and N93S mutations in the heavy chain Fc region, and KV:F2I, KV:S18P and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 111, respectively;

(rr) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 191 or amino acids 20-238 of SEQ ID NO: 114. The antibody or antigen-binding fragment thereof has M87L and N93S mutations in the heavy chain Fc region, and KV:F2I, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 113, respectively;

(ss) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 192 or amino acids 20-238 of SEQ ID NO: 116. The antibody or antigen-binding fragment thereof has M87L and N93S mutations in the heavy chain Fc region, and KV:H9L, KV:S18P and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 115, respectively;

(tt) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 193 or amino acids 20-238 of SEQ ID NO: 118. The antibody or antigen-binding fragment thereof has M87L and N93S mutations in the heavy chain Fc region, and KV:H9L, KV:S18P and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 117, respectively;

(uu) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 194 or amino acids 20-238 of SEQ ID NO: 120. The antibody or antigen-binding fragment thereof has M87L and N93S mutations in the heavy chain Fc region, and KV:H9L, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 119, respectively;

(vv) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 195 or amino acids 20-238 of SEQ ID NO: 122. The antibody or antigen-binding fragment thereof has M87L and N93S mutations in the heavy chain Fc region, and KV:S18P, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 121, respectively;

(ww) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 196 or amino acids 20-238 of SEQ ID NO: 124. The antibody or antigen-binding fragment thereof has M87L and N93S mutations in the heavy chain Fc region, and KV:F2I, KV:H9L, KV:S18P and KV:D73G mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 123, respectively;

(xx) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 197 or amino acids 20-238 of SEQ ID NO: 126. The antibody or antigen-binding fragment thereof has M87L and N93S mutations in the heavy chain Fc region, and KV:F2I, KV:H9L, KV:S18P and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 125, respectively;

(yy) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 198 or amino acids 20-238 of SEQ ID NO: 128. The antibody or antigen-binding fragment thereof has M87L and N93S mutations in the heavy chain Fc region, and KV:F2I, KV:H9L, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 127, respectively;

(zz) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 199 or amino acids 20-238 of SEQ ID NO: 130. The antibody or antigen-binding fragment thereof has M87L and N93S mutations in the heavy chain Fc region, and KV:F2I, KV:S18P, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 129, respectively;

(aaa) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 200 or amino acids 20-238 of SEQ ID NO: 132. The antibody or antigen-binding fragment thereof has M87L and N93S mutations in the heavy chain Fc region, and KV:H9L, KV:S18P, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 131, respectively; or (bbb) a PGDM1400 variant antibody or antigen-binding fragment thereof featured herein includes: (i) the following six complementarity determining regions (CDRs): a heavy chain (HC)-CDR1 with the amino acid sequence of SEQ ID NO: 12, or 3 or fewer (e.g., 2 or 1) amino acid modification(s) (e.g., insertion, deletion, or substitution) relative to the amino acid sequence of SEQ ID NO: 12; a HC-CDR2 with the amino acid sequence of SEQ ID NO: 14, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 14; a HC-CDR3 with the amino acid sequence of SEQ ID NO: 16, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 16; a light chain (LC)-CDR1 with the amino acid sequence of SEQ ID NO: 4, or 10 or fewer (e.g., 9, 8, 7, 6, 5, 4, 3, 2 or 1) amino acid modification(s) (e.g., insertion, deletion, or substitution) relative to the amino acid sequence of SEQ ID NO: 4; a LC-CDR2 with the amino acid sequence of SEQ ID NO: 6, or 5 or fewer (e.g., 4, 3, 2 or 1) amino acid modification(s) (e.g., insertion, deletion, or substitution) relative to the amino acid sequence of SEQ ID NO: 6; and a LC-CDR3 with the amino acid sequence of SEQ ID NO: 8, or 5 or fewer (e.g., 4, 3, 2 or 1) amino acid modification(s) (e.g., insertion, deletion, or substitution) relative to the amino acid sequence of SEQ ID NO: 8; or (ii) a heavy chain variable domain having the sequence of SEQ ID NO: 136 or amino acids 20-490 of SEQ ID NO: 10, and a light chain variable domain having the sequence of SEQ ID NO: 201 or amino acids 20-238 of SEQ ID NO: 134. The antibody or antigen-binding fragment thereof has M87L and N93S mutations in the heavy chain Fc region, and KV:F2I, KV:H9L, KV:S18P, KV:D73G and KV:T85A mutations in the light chain variable domain. In a particular antibody or antigen-binding fragment thereof, the HC-CDR1, the HC-CDR2, the HC-CDR3, the LC-CDR1, the LC-CDR2, the LC-CDR3, the heavy chain variable domain, and the light chain variable domain of the antibody or antigen-binding fragment thereof are encoded by the nucleotide sequences of SEQ ID NOs: 11, 13, 15, 3, 5, 7, 9, and 133, respectively.

For manufacturing an antibody or antigen-binding fragment thereof of (a)-(bbb) above (e.g., using an expression system), the heavy and light chain amino acid sequences noted above may include a signal peptide. The signal peptide corresponds to residues 1-19 of the sequences noted above. During maturation, the signal peptide is cleaved. Hence, the mature form of the antibody or antigen-binding fragment thereof lacks the first 1-19 amino acids of the sequence of the respective heavy and light chain domain. The residue numbering corresponds to the amino acid position of the mature linear sequence for the heavy and light chain variable domains of the antibodies described herein, which excludes the signal peptide sequence (amino acids 1-19). For example, position 2 of the mature linear sequence of the light chain variable domain of MS-66 (i.e., SEQ ID NO: 144) begins at amino acid position 21 of SEQ ID NO: 18. Position 21 of SEQ ID NO: 18 corresponds to the KV:F2I substitution.

Residues 1-57 of the nucleotide sequence of heavy and light chain variable domains of the PGDM1400 variant antibody or antigen-binding fragment thereof featured herein (e.g., residue 1-57 of SEQ ID NOs: 1, 9, 17, 19, 21, 23, 25, 27, 29, 31, 33, 35, 37, 39, 41, 43, 45, 47, 49, 51, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and 133) encode signal peptides, which, as noted in the foregoing section, are cleaved during maturation, and henceforth, are not a part of the mature linear sequence of the heavy and light chain variable domains of the PGDM1400 variant antibody or antigen-binding fragment thereof featured herein.

In specific embodiments, the PGDM1400 variant antibody or antigen-binding fragment thereof featured herein may be selected from the group consisting of the aforementioned: (a), (b), (d), (f), (h), (cc), (dd), (ee), (ff), (gg), (hh), (ii), (jj), (kk), (ll), (mm), (nn), (oo), (pp), (qq), (rr), (ss), (tt), (uu), (vv), (ww), (xx), (yy), (zz), (aaa), and (bbb). Specifically, the PGDM1400 variant antibody or antigen-binding fragment thereof featured herein may be selected from the group consisting of the aforementioned: (cc), (dd), (ee), (ff), (gg), (hh), (ii), (jj), (kk), (ll), (mm), (nn), (oo), (pp), (qq), (rr), (ss), (tt), (uu), (vv), (ww), (xx), (yy), (zz), (aaa), and (bbb). Preferentially, the PGDM1400 variant antibody or antigen-binding fragment thereof featured herein may be selected from the group consisting of the aforementioned: (cc), (dd), (ee), (ff), (mm), (nn), (oo), (pp), (qq), (rr), (ww), (xx), (yy), (zz), and (bbb). Preferably, the PGDM1400 variant antibody or antigen-binding fragment thereof featured herein is (cc) (e.g., MS-93).

In specific embodiments, the PGDM1400 variant antibody or antigen-binding fragment thereof featured herein may be selected from the group consisting of the following from Tables 1 and 2: MS-66, MS-67, MS-69, MS-71, MS-73, MS-93, MS-94, MS-95, MS-96, MS-97, MS-98, MS-99, MS-100, MS-101, MS-102, MS-103, MS-104, MS-105, MS-106, MS-107, MS-108, MS-109, MS-110, MS-111, MS-112, MS-113, MS-114, MS-115, MS-116, MS-117, and MS-118. In selective embodiments, the PGDM1400 variant antibody or antigen-binding fragment thereof featured herein may be selected from the group consisting of the following from Table 2: MS-93, MS-94, MS-95, MS-96, MS-97, MS-98, MS-99, MS-100, MS-101, MS-102, MS-103, MS-104, MS-105, MS-106, MS-107, MS-108, MS-109, MS-110, MS-111, MS-112, MS-113, MS-114, MS-115, MS-116, MS-117, and MS-118. Preferentially, the PGDM1400 variant antibody or antigen-binding fragment thereof featured herein may be selected from the group consisting of the following from Table 2: MS-93, MS-94, MS-95, MS-96, MS-103, MS-104, MS-105, MS-106, MS-107, MS-108, MS-113, MS-114, MS-115, MS-116, and MS-118. Preferably, the PGDM1400 variant antibody or antigen-binding fragment thereof featured herein is MS-93.

In some embodiments, the CDR sequences noted above for the PGDM1400 variant antibodies (a)-(bbb) may differ by one, two, three, four, five, six, seven, eight, nine, or ten amino acid residues from the recited sequences. In such embodiments, insertion (e.g., insertion of one, two, three, four, five, six, seven, eight, nine, or ten amino acid residues), deletion (e.g., deletion of one, two, three, four, five, six, seven, eight, nine, or ten amino acid residues), or substitution (e.g., substitution of one, two, three, four, five, six, seven, eight, nine, or ten amino acid residues) may account for the amino acid difference (e.g., difference of one, two, three, four, five, six, seven, eight, nine, or ten amino acid residues) of the CDR sequences from the recited CDR sequences noted herein. The amino acid substitution in the CDR(s), if present, may be a conservative amino acid substitution.

II. Design of the PGDM1400 Variant Antibodies

Antibody variants (e.g., PGDM1400 variant antibodies) or antigen-binding fragments thereof, described herein may be produced by an optimization process. The optimization process may be broken up into different stages with the first being identification of single residues in the framework region that may be responsible for destabilization of the parental PGDM1400 antibody. A series of variants can be produced by transient expression (e.g., transient expression in Human Embryonic Kidney 293 (HEK293) or Chinese Hamster Ovary (CHO) cells), each containing a single residue modification of amino acids, or in a few variants, combinations of amino acids based on proximity to each other (e.g., one or more of the Round-1 variants of Table 1). These variants may be characterized for retention of neutralization activity (e.g., neutralization activity against pseudoviruses of human immunodeficiency virus (HIV), such as SC422661.8, RHPA4259.7, Du172.17, BB1012-11.TC21, CNE52, 0260.v5.c36, 263-8, SC05.8C11.2344, X1193_c1, Ce1176_A3, AC10.0.29, and 6952.v1.c20) and for desired biophysical characteristics (e.g., low-pH stability, solubility, thermal stability, chemical unfolding, and reduced aggregation).

We identified several single residues at the light chain/heavy chain interface that significantly reduce low-pH instability (e.g., instability at pH 3.3) of the parental PGDM1400 antibody. Additionally, we identified amino acid residue combinations the substitution of which promoted an increase in desirable biophysical characteristics, while not impacting neutralization characteristics (e.g., neutralization or inactivation of viruses). Together, these residues were used to produce a library of variants (e.g., one or more of the Round-2 variants of Table 2) encompassing combinatorial residue replacements. The variants can be produced by transient expression (e.g., transient expression in HEK293 or CHO cells) and the purified combinatorial variants can be analyzed for retention of neutralization activity (e.g., neutralization activity against pseudoviruses of human immunodeficiency virus (HIV), such as SC422661.8, RHPA4259.7, Du172.17, BB1012-11.TC21, CNE52, 0260.v5.c36, 263-8, SC05.8C11.2344, X1193_c1, Ce1176_A3, AC10.0.29, and 6952.v1.c20) and for desired biophysical characteristics (e.g., low-pH stability, solubility, thermal stability, chemical unfolding, and reduced aggregation). From this combinatorial library a subset of variants may be used to construct a library. Together, the combinatorial libraries of variants allow for identification of antibody variants or fragments thereof with desired biophysical characteristics, such as with significantly increased low-pH stability (e.g., stability at about pH 3.3), increased thermal stability (e.g., tested during thermal ramping between about 20-95° C.), increased solubility (e.g., in a final PEG 10,000 concentration of about 9.4%), reduced aggregation (e.g., reduced levels of aggregation following low-pH (e.g., about pH 3.3) incubation) as evaluated by monomer and/or oligomer content (e.g., monomer content more than about 60% (e.g., more than about 65%, 70%, 75%, 80%, 85%, 90%, 95%, 96%, or 97%), and/or oligomer content less than about 10% (e.g., less than about 9%, 8%, 7%, 6%, 5%, 4%, 3%, 2%, 1%, 0.5%, 0.4%, or 0.3%)), and increased intramolecular and thermodynamic stability, such as chemical stability, as determined by chemical unfolding (e.g., tested by guanidine hydrochloride (GuHCl) or urea concentrations, preferably by GuHCl concentrations).

TABLE 1

Round-1 variants.

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| PGDM1400 | LC-CDR 1-3<br>aa: 4, 6, 8<br>nt: 3, 5, 7<br>HC-CDR 1-3<br>aa: 12, 14, 16<br>nt: 11, 13, 15 | aa: 135<br>nt: 1[1] | aa: 136<br>nt: 9 | No modification | No modification | No modification |
| MS-119 | LC-CDR 1-3<br>aa: 4, 6, 8<br>nt: 3, 5, 7<br>HC-CDR 1-3<br>aa: 12, 14, 16<br>nt: 11, 13, 15 | aa: 135<br>nt: 1 | aa: 136<br>nt: 9 | No modification | No modification | M87L; N93S |
| MS-66 | LC-CDR 1-3<br>aa: 4, 6, 8<br>nt: 3, 5, 7<br>HC-CDR 1-3<br>aa: 12, 14, 16<br>nt: 11, 13, 15 | aa: 144<br>nt: 17 | aa: 136<br>nt: 9 | KV: F2I | No modification | M87L; N93S |
| MS-67 | LC-CDR 1-3<br>aa: 4, 6, 8<br>nt: 3, 5, 7<br>HC-CDR 1-3<br>aa: 12, 14, 16<br>nt: 11, 13, 15 | aa: 145<br>nt: 19 | aa: 136<br>nt: 9 | KV: H9L | No modification | M87L; N93S |
| MS-68 | LC-CDR 1-3<br>aa: 4, 6, 8<br>nt: 3, 5, 7<br>HC-CDR 1-3<br>aa: 12, 14, 16<br>nt: 11, 13, 15 | aa: 146<br>nt: 21 | aa: 136<br>nt: 9 | KV: S12P | No modification | M87L; N93S |
| MS-69 | LC-CDR 1-3<br>aa: 4, 6, 8<br>nt: 3, 5, 7<br>HC-CDR 1-3<br>aa: –12, 14, 16<br>nt: 11, 13, 15 | aa: 147<br>nt: 23 | aa: 136<br>nt: 9 | KV: S18P | No modification | M87L; N93S |
| MS-70 | LC-CDR 1-3<br>aa: 4, 6, 8<br>nt: 3, 5, 7<br>HC-CDR 1-3<br>aa: 12, 14, 16<br>nt: 11, 13, 15 | aa: 148<br>nt: 25 | aa: 136<br>nt: 9 | KV: R47Q | No modification | M87L; N93S |
| MS-71 | LC-CDR 1-3<br>aa: 4, 6, 8<br>nt: 3, 5, 7<br>HC-CDR 1-3<br>aa: 12, 14, 16<br>nt: 11, 13, 15 | aa: 149<br>nt: 27 | aa: 136<br>nt: 9 | KV: D73G | No modification | M87L; N93S |
| MS-72 | LC-CDR 1-3<br>aa: 4, 6, 8<br>nt: 3, 5, 7<br>HC-CDR 1-3<br>aa: 12, 14, 16<br>nt: 11, 13, 15 | aa: 150<br>nt: 29 | aa: 136<br>nt: 9 | KV: K74T | No modification | M87L; N93S |
| MS-73 | LC-CDR 1-3<br>aa: 4, 6, 8<br>nt: 3, 5, 7<br>HC-CDR 1-3<br>aa: 12, 14, 16<br>nt: 11, 13, 15 | aa: 151<br>nt: 31 | aa: 136<br>nt: 9 | KV: T85A | No modification | M87L; N93S |
| MS-74 | LC-CDR 1-3<br>aa: 4, 6, 8<br>nt: 3, 5, 7<br>HC-CDR 1-3<br>aa: 12, 14, 16<br>nt: 11, 13, 15 | aa: 152<br>nt: 33 | aa: 136<br>nt: 9 | KV: T90V | No modification | M87L; N93S |

TABLE 1-continued

Round-1 variants.

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| MS-75 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 153 nt: 35 | No modification | HV: P25S | M87L; N93S |
| MS-76 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 154 nt: 37 | No modification | HV: N27Y | M87L; N93S |
| MS-77 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 155 nt: 39 | No modification | HV: L29F | M87L; N93S |
| MS-78 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 156 nt: 41 | No modification | HV: Q46E | M87L; N93S |
| MS-79 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 157 nt: 43 | No modification | HV: D71T | M87L; N93S |
| MS-80 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 158 nt: 45 | No modification | HV: W72R | M87L; N93S |
| MS-81 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 159 nt: 47 | No modification | HV: Q82E | M87L; N93S |
| MS-82 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 160 nt: 49 | No modification | HV: T87R | M87L; N93S |
| MS-83 | LC-CDR 1-3 aa: 4, 6, 8 nt: 3, 5, 7 HC-CDR 1-3 aa: 12, 14, 54 nt: 11, 13, 53 | aa: 135 nt: 1 | aa: 161 nt: 51 | No modification | HV: D113E | M87L; N93S |
| MS-84 | LC-CDR 1-3 aa: 4, 6, 8 nt: 3, 5, 7 HC-CDR 1-3 aa: 12, 14, 16 nt: 11, 13, 15 | aa: 162 nt: 55 | aa: 163 nt: 57 | KV: H9L, KV: S12P, KV: S18P, KV: R47Q, KV: T85A, KV: T90V | HV: T87R | M87L; N93S |
| MS-85 | LC-CDR 1-3 aa: 4, 6, 8 nt: 3, 5, 7 HC-CDR 1-3 aa: 12, 14, 16 nt: 11, 13, 15 | aa: 164 nt: 59 | aa: 136 nt: 9 | KV: F2I, KV: D73G, KV: K74T | No modification | M87L; N93S |

TABLE 1-continued

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| Round-1 variants. | | | | | | |
| MS-86 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 165 nt: 61 | No modification | HV: P25S, HV: N27Y, HV: L29F | M87L; N93S |
| MS-87 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 166 nt: 63 | No modification | HV: D71T, HV: W72R | M87L; N93S |
| MS-88 | LC-CDR 1-3 aa: 4, 6, 8 nt: 3, 5, 7 HC-CDR 1-3 aa: 12, 14, 16 nt: 11, 13, 15 | aa: 135 nt: 1 | aa: 167 nt: 65 | No modification | HV: P25S, HV: N27Y, HV: L29F, HV: D71T, HV: W72R | M87L; N93S |
| MS-89 | LC-CDR 1-3 aa: 4, 6, 8 nt: 3, 5, 7 HC-CDR 1-3 aa: 12, 14, 16 nt: 11, 13, 15 | aa: 168 nt: 67 | aa: 169 nt: 69 | KV: H9L | HV: N27Y, HV: D71T | M87L; N93S |
| MS-90 | LC-CDR 1-3 aa: 4, 6, 8 nt: 3, 5, 7 HC-CDR 1-3 aa: 12, 14, 16 nt: 11, 13, 15 | aa: 170 nt: 71 | aa: 171 nt: 73 | KV: H9L | HV: P25S, HV: N27Y, HV: L29F | M87L; N93S |
| MS-91 | LC-CDR 1-3 aa: 4, 6, 8 nt: 3, 5, 7 HC-CDR 1-3 aa: 12, 14, 16 nt: 11, 13, 15 | aa: 172 nt: 75 | aa: 173 nt: 77 | KV: H9L, KV: K74T | HV: P25S, HV: N27Y | M87L; N93S |
| MS-92 | LC-CDR 1-3 aa: 4, 6, 8 nt: 3, 5, 7 HC-CDR 1-3 aa: 12, 14, 16 nt: 11, 13, 15 | aa: 174 nt: 79 | aa: 175 nt: 81 | KV: F2I | HV: Q46E, HV: W72R, HV: T87R | M87L; N93S |

[1]Residues 1-57 of the nucleotide sequence for the heavy and light chain variable domains encode signal peptides, which are not a part of the mature sequence for the heavy and light chain variable domains indicated by the sequence identifiers in this table.

IgG1 LC: light chain sequence modification

IgG1 HC: heavy chain sequence modification

TABLE 2

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| Round-2 variants. | | | | | | |
| MS-93 | LC-CDR 1-3 aa: 4, 6, 8 nt: 3, 5, 7 HC-CDR 1-3 aa: 12, 14, 16 nt: 11, 13, 15 | aa: 176 nt: 83[2] | aa: 136 nt: 9 | KV: F2I, KV: H9L | No modification | M87L; N93S |

TABLE 2-continued

Round-2 variants.

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| MS-94 | LC-CDR 1-3 aa: 4, 6, 8 nt: 3, 5, 7 HC-CDR 1-3 aa: 12, 14, 16 nt: 11, 13, 15 | aa: 177 nt: 85 | aa: 136 nt: 9 | KV: F2I, KV: S18P | No modification | M87L; N93S |
| MS-95 | LC-CDR 1-3 aa: 4, 6, 8 nt: 3, 5, 7 HC-CDR 1-3 aa: 12, 14, 16 nt: 11, 13, 15 | aa: 178 nt: 87 | aa: 136 nt: 9 | KV: F2I, KV: D73G | No modification | M87L; N93S |
| MS-96 | LC-CDR 1-3 aa: 4, 6, 8 nt: 3, 5, 7 HC-CDR 1-3 aa: 12, 14, 16 nt: 11, 13, 15 | aa: 179 nt: 89 | aa: 136 nt: 9 | KV: F2I, KV: T85A | No modification | M87L; N93S |
| MS-97 | LC-CDR 1-3 aa: 4, 6, 8 nt: 3, 5, 7 HC-CDR 1-3 aa: 12, 14, 16 nt: 11, 13, 15 | aa: 180 nt: 91 | aa: 136 nt: 9 | KV: H9L, KV: S18P | No modification | M87L; N93S |
| MS-98 | LC-CDR 1-3 aa: 4, 6, 8 nt: 3, 5, 7 HC-CDR 1-3 aa: 12, 14, 16 nt: 11, 13, 15 | aa: 181 nt: 93 | aa: 136 nt: 9 | KV: H9L, KV: D73G | No modification | M87L; N93S |
| MS-99 | LC-CDR 1-3 aa: 4, 6, 8 nt: 3, 5, 7 HC-CDR 1-3 aa: 12, 14, 16 nt: 11, 13, 15 | aa: 182 nt: 95 | aa: 136 nt: 9 | KV: H9L, KV: T85A | No modification | M87L; N93S |
| MS-100 | LC-CDR 1-3 aa: 4, 6, 8 nt: 3, 5, 7 HC-CDR 1-3 aa: 12, 14, 16 nt: 11, 13, 15 | aa: 183 nt: 97 | aa: 136 nt: 9 | KV: S18P, KV: D73G | No modification | M87L; N93S |
| MS-101 | LC-CDR 1-3 aa: 4, 6, 8 nt: 3, 5, 7 HC-CDR 1-3 aa: 12, 14, 16 nt: 11, 13, 15 | aa: 184 nt: 99 | aa: 136 nt: 9 | KV: S18P, KV: T85A | No modification | M87L; N93S |
| MS-102 | LC-CDR 1-3 aa: 4, 6, 8 nt: 3, 5, 7 HC-CDR 1-3 aa: 12, 14, 16 nt: 11, 13, 15 | aa: 185 nt: 101 | aa: 136 nt: 9 | KV: D73G, KV: T85A | No modification | M87L; N93S |
| MS-103 | LC-CDR 1-3 aa: 4, 6, 8 nt: 3, 5, 7 HC-CDR 1-3 aa: 12, 14, 16 nt: 11, 13, 15 | aa: 186 nt: 103 | aa: 136 nt: 9 | KV: H9L, KV: S18P | No modification | M87L; N93S |
| MS-104 | LC-CDR 1-3 aa: 4, 6, 8 nt: 3, 5, 7 HC-CDR 1-3 aa: 12, 14, 16 nt: 11, 13, 15 | aa: 187 nt: 105 | aa: 136 nt: 9 | KV: F2I, KV: H9L, KV: D73G | No modification | M87L; N93S |

TABLE 2-continued

Round-2 variants.

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| MS-105 | LC-CDR 1-3 aa: 4, 6, 8 nt: 3, 5, 7 HC-CDR 1-3 aa: 12, 14, 16 nt: 11, 13, 15 | aa: 188 nt: 107 | aa: 136 nt: 9 | KV: F2I, KV: H9L, KV: T85A | No modification | M87L; N93S |
| MS-106 | LC-CDR 1-3 aa: 4, 6, 8 nt: 3, 5, 7 HC-CDR 1-3 aa: 12, 14, 16 nt: 11, 13, 15 | aa: 189 nt: 109 | aa: 136 nt: 9 | KV: F2I, KV: S18P, KV: D73G | No modification | M87L; N93S |
| MS-107 | LC-CDR 1-3 aa: 4, 6, 8 nt: 3, 5, 7 HC-CDR 1-3 aa: 12, 14, 16 nt: 11, 13, 15 | aa: 190 nt: 111 | aa: 136 nt: 9 | KV: F2I, KV: S18P, KV: T85A | No modification | M87L; N93S |
| MS-108 | LC-CDR 1-3 aa: 4, 6, 8 nt: 3, 5, 7 HC-CDR 1-3 aa: 12, 14, 16 nt: 11, 13, 15 | aa: 191 nt: 113 | aa: 136 nt: 9 | KV: F2I, KV: D73G, KV: T85A | No modification | M87L; N93S |
| MS-109 | LC-CDR 1-3 aa: 4, 6, 8 nt: 3, 5, 7 HC-CDR 1-3 aa: 12, 14, 16 nt: 11, 13, 15 | aa: 192 nt: 115 | aa: 136 nt: 9 | KV: H9L, KV: S18P, KV: D73G | No modification | M87L; N93S |
| MS-110 | LC-CDR 1-3 aa: 4, 6, 8 nt: 3, 5, 7 HC-CDR 1-3 aa: 12, 14, 16 nt: 11, 13, 15 | aa: 193 nt: 117 | aa: 136 nt: 9 | KV: H9L, KV: S18P, KV: T85A | No modification | M87L; N93S |
| MS-111 | LC-CDR 1-3 aa: 4, 6, 8 nt: 3, 5, 7 HC-CDR 1-3 aa: 12, 14, 16 nt: 11, 13, 15 | aa: 194 nt: 119 | aa: 136 nt: 9 | KV: H9L, KV: D73G, KV: T85A | No modification | M87L; N93S |
| MS-112 | LC-CDR 1-3 aa: 4, 6, 8 nt: 3, 5, 7 HC-CDR 1-3 aa: 12, 14, 16 nt: 11, 13, 15 | aa: 195 nt: 121 | aa: 136 nt: 9 | KV: S18P, KV: D73G, KV: T85A | No modification | M87L; N93S |
| MS-113 | LC-CDR 1-3 aa: 4, 6, 8 nt: 3, 5, 7 HC-CDR 1-3 aa: 12, 14, 16 nt: 11, 13, 15 | aa: 196 nt: 123 | aa: 136 nt: 9 | KV: F2I, KV: H9L, KV: S18P, KV: D73G | No modification | M87L; N93S |
| MS-114 | LC-CDR 1-3 aa: 4, 6, 8 nt: 3, 5, 7 HC-CDR 1-3 aa: 12, 14, 16 nt: 11, 13, 15 | aa: 197 nt: 125 | aa: 136 nt: 9 | KV: F2I, KV: H9L, KV: S18P, KV: T85A | No modification | M87L; N93S |
| MS-115 | LC-CDR 1-3 aa: 4, 6, 8 nt: 3, 5, 7 HC-CDR 1-3 aa: 12, 14, 16 nt: 11, 13, 15 | aa: 198 nt: 127 | aa: 136 nt: 9 | KV: F2I, KV: H9L, KV: D73G, KV: T85A | No modification | M87L; N93S |

TABLE 2-continued

Round-2 variants.

| Molecule Set | Light Chain (LC)-CDR 1-3 Amino acid (aa) SEQ ID NO: Nucleotide (nt) SEQ ID NO: Heavy Chain (HC)-CDR 1-3 Amino acid (aa) SEQ ID NO: Nucleotide (nt) SEQ ID NO: | Light Chain Variable Domain Amino acid (aa) SEQ ID NO: Nucleotide (nt) SEQ ID NO: | Heavy Chain Variable Domain Amino acid (aa) SEQ ID NO: Nucleotide (nt) SEQ ID NO: | IgG1 Light Chain Modification (Relative to SEQ ID NO: 135) | IgG1 Heavy Chain Modification (Relative to SEQ ID NO: 136) | Fc Domain Modification (Relative to SEQ ID NO: 137) |
|---|---|---|---|---|---|---|
| MS-116 | LC-CDR 1-3<br>aa: 4, 6, 8<br>nt: 3, 5, 7<br>HC-CDR 1-3<br>aa: 12, 14, 16<br>nt: 11, 13, 15 | aa: 199<br>nt: 129 | aa: 136<br>nt: 9 | KV: F2I, KV: S18P, KV: D73G, KV: T85A | No modification | M87L; N93S |
| MS-117 | LC-CDR 1-3<br>aa: 4, 6, 8<br>nt: 3, 5, 7<br>HC-CDR 1-3<br>aa: 12,14,16<br>nt: 11, 13, 15 | aa: 200<br>nt: 131 | aa: 136<br>nt: 9 | KV: H9L, KV: S18P, KV: D73G, KV: T85A | No modification | M87L; N93S |
| MS-118 | LC-CDR 1-3<br>aa: 4, 6, 8<br>nt: 3, 5, 7<br>HC-CDR 1-3<br>aa: 12,14,16<br>nt: 11, 13, 15 | aa: 201<br>nt: 133 | aa: 136<br>nt: 9 | KV: F2I, KV: H9L, KV: S18P, KV: D73G, KV: T85A | No modification | M87L; N93S |

[2]Residues 1-57 of the nucleotide sequence for the heavy and light chain variable domains encode signal peptides, which are not a part of the mature sequence for the heavy and light chain variable domains indicated by the sequence identifiers in this table.
IgG1 LC: light chain sequence modification
IgG1 HC: heavy chain sequence modification III. Biophysical Properties of the PGDM1400 Antibody Variants PGDM1400 variant antibodies and antigen-binding fragments thereof that are produced by the optimization program described herein exhibit one or more of the following biophysical characteristics: increased low-pH stability; increased thermal stability; increased solubility; reduced aggregation; and increased intramolecular and thermodynamic stability, such as chemical stability, as determined by chemical unfolding. These biophysical attributes have been shown to be linked to improved manufacturability and storage stability.

Solubility

The PGDM1400 variant antibodies or fragments thereof described herein exhibit improved solubility, e.g., relative to the parental PGDM1400 antibody. The featured PGDM1400 variant antibodies or fragments thereof described herein exhibit solubility of at least about 1 mg/ml (e.g., about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 5.5 mg/ml, 6.0 mg/ml, 6.5 mg/ml, 7.0 mg/ml, 7.5 mg/ml, 8.0 mg/ml, 8.5 mg/ml, 9.0 mg/ml, 9.5 mg/ml, or 10.0 mg/ml) in a solution containing about 6-10% PEG 10,000 (e.g., about 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% PEG 10,000). In particular, at least 1 mg/ml of the antibody or fragment thereof is soluble in a solution with a concentration of 9.4% PEG 10,000. Improved solubility of the PGDM1400 variant antibodies and fragments thereof, relative to the native PGDM1400 antibody, increases efficient production (e.g., higher production titer) of the antibodies by minimizing the amounts of antibodies lost through precipitation (e.g., aggregation).

Thermal Stability

The PGDM1400 variant antibodies or fragments thereof described herein exhibit high thermal stability, e.g., relative to the parental PGDM1400 antibody. The PGDM1400 variant antibodies and fragments thereof described herein exhibit reduced degradation or resistance to degradation upon exposure to a wide range of temperature variations (e.g., thermal ramping at temperatures of between about 20-95° C.). Specifically, the PGDM1400 variant antibodies and fragments thereof described herein exhibit reduced degradation or resistance to degradation upon exposure to about 68° C. and/or about 69.2° C. Thermal stability of the PGDM1400 variant antibodies or fragments thereof described herein ensure their stability and sustainability when exposed to extreme non-physiologic conditions, such as conditions during manufacture or production of the antibodies. The improved thermal stability of the PGDM1400 variant antibodies or fragments thereof described herein contributes to their improved manufacturability. Improved thermal stability of the PGDM1400 variant antibodies or fragments thereof described herein also contributes to improved storage stability (e.g., stability when stored at a temperature of about −30° C. to about 25° C. (e.g., about −30° C., −25° C., −20° C., −15° C., −10° C., −5° C., 0° C., 5° C., 10° C., 15° C., 20° C., 25° C., 30° C., or 35° C.) over about 2 days, 3 days, 4 days, 5 days, 6 days, 1 week, 2 weeks, 3 weeks, 1 month, 2 months, 3 months, 4 months, 5 months, 6 months, 1 year, 2 years, 3 years, 4 years, 5 years, or more), making them more suitable for extended storage and subsequent therapeutic application.

Chemical Stability

The PGDM1400 variant antibodies or fragments thereof described herein exhibit increased chemical stability, e.g., relative to the parental PGDM1400 antibody. The featured PGDM1400 variant antibodies and fragments thereof exhibit chemical stability, as determined by chemical unfolding (e.g., as tested by guanidine hydrochloride (GuHCl) or urea concentrations, preferably by GuHCl concentrations). For example, the PGDM1400 variant antibodies described herein exhibit increased chemical stability at a final concentration of the antibody or fragment thereof of about 0.01-5.0 mg/ml (e.g., about 0.02 mg/ml, 0.03 mg/ml, 0.04 mg/ml, 0.05 mg/ml, 0.06 mg/ml, 0.07 mg/ml, 0.08 mg/ml, 0.09 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, or 5.0 mg/ml, for example at a final concentration of about 0.05 mg/ml) in the presence of GuHCl (e.g., a concentration of GuHCL of greater than about 0.001 M to about 6 M GuHCL), relative to the parental PGDM1400 antibody. In specific embodiments, the PGDM1400 variant antibody or fragment thereof (e.g., at a concentration of about 0.05 mg/ml) may exhibit reduced chemical unfolding in the presence of about 2.0 M or greater GuHCL (e.g., greater than 2.5 M, greater than 3.0 M, greater than 3.5 M, greater than 4.0 M, greater than 4.5 M, greater than 5.0 M, or greater than 5.5 M) GuHCl. For example, the PGDM1400 variant antibody or fragment thereof at a final concentration of about 0.05 mg/ml may exhibit reduced chemical unfolding relative to the parental PGDM1400 antibody (e.g., an equilibrium denaturation point) at a GuHCl concentration of about 2.0-2.5 M. The improved chemical stability of the PGDM1400 variant antibodies or fragments thereof described herein indicates that the PGDM1400 variant antibodies and fragments thereof exhibit improved stability and sustainability under various conditions, such as those during manufacture or production of the antibodies or fragments thereof. The chemical stability of the PGDM1400 variant antibodies or fragments thereof described herein thus contributes to the improved manufacturability of the same.

Low-pH Stability

The PGDM1400 variant antibodies or fragments thereof described herein exhibit improved stability at low pH, e.g., relative to the parental PGDM1400 antibody. The featured PGDM1400 variant antibodies and fragments thereof exhibit improved stability (e.g., reduced aggregation) when exposed to low pH, such as a pH less than about pH 5.0 (e.g., less than pH 4.6, less than pH 4.3, less than pH 4.0, less than pH 3.6, less than pH 3.3, or at pH 3.0 (e.g., at pH 3.3)). In preferred embodiments the featured PGDM1400 variant antibodies or fragments thereof exhibit improved stability at about pH 3.3, e.g., relative to the parental PGDM1400 antibody. The stability of the PGDM1400 variant antibodies or fragments thereof at low pH is measured in terms of reduced aggregation or resistance to aggregation upon exposure to the low pH conditions (for e.g., as assessed following neutralization to a higher pH). The featured PGDM1400 variant antibodies or fragments thereof do not aggregate or exhibit reduced aggregation (e.g., high molecular weight species) upon neutralization from low pH exposure, which in preferred embodiments is about pH 3.3. The improved low-pH stability of the PGDM1400 variant antibodies or fragments thereof described herein ensures their stability and sustainability when exposed to low pH or acidic conditions, e.g., during manufacture or production of the antibodies and fragments thereof. Low-pH stability of the PGDM1400 variant antibodies or fragments thereof described herein thus contributes to the improved manufacturability of the same.

Reduced Aggregation

The PGDM1400 variant antibodies or fragments thereof described herein exhibit reduced aggregation (e.g., reduced aggregation when exposed to low pH, solubilizing or chaotropic chemicals, and/or increased temperatures), e.g., relative to the parental PGDM1400 antibody. Aggregation can be evaluated by monitoring monomer content and/or oligomer content over time (e.g., over days, weeks, months, or years). The featured PGDM1400 variant antibodies and fragments thereof exhibit reduced aggregation (e.g., reduced levels of aggregation following low-pH (e.g., pH 3.3) incubation), as evaluated by monomer and/or oligomer content (e.g., monomer content more than about 60% (e.g., more than about 65%, 70%, 75%, 80%, 85%, 90%, 95%, 96%, or 97%), and/or oligomer content less than about 10% (e.g., less than about 9%, 8%, 7%, 6%, 5%, 4%, 3%, 2%, 1%, 0.5%, 0.4%, or 0.3%)). Reduced aggregation of the PGDM1400 variant antibodies or fragments thereof described herein ensure their stability and sustainability when exposed to chemicals, low pH conditions, and extreme temperatures (e.g., large temperature variations or increased temperatures, e.g., in range of about −30° C. to about 35° C.) during manufacture or production of the antibodies or fragments thereof. Reduced aggregation of the PGDM1400 variant antibodies or fragments thereof described herein thus contributes to improved manufacturability of the same. Reduced aggregation of the PGDM1400 variant antibodies or fragments thereof described herein also ensures their stability during storage (e.g., storage for over about 2 days, over about 3 days, over about 4 days, over about 5 days, over about 6 days, over about 1 week, over about 2 weeks, over about 3 weeks, over about 1 month, over about 2 months, over about 3 months, over about 4 months, over about 5 months, over about 6 months, over about 7 months, over about 8 months, over about 9 months, over about 10 months, over about 11 months, over about 1 year, over about 2 years, over about 3 years, over about 4 years, over about 5 years, or more, at a temperature of about −30° C. to about 35° C. (e.g., about −30° C., −25° C., −20° C., −15° C., −10° C., −5° C., 0° C., 5° C., 10° C., 15° C., 20° C., 25° C., 30° C., or 35° C.)). Storage stability of the PGDM1400 variant antibodies or fragments thereof also ensures longer shelf life, retention of efficacy and safer therapeutic application of the same. With improved manufacturability and storage stability, the PGDM1400 variant antibodies or antigen-binding fragments thereof, featured herein, exhibit improved characteristics relative to the native PGDM1400 antibody.

Pharmacokinetics and Binding Affinity

The PGDM1400 variant antibodies or antigen-binding fragments thereof described herein exhibit a half-life of at least about 1 hour (e.g., at least about 1 hour, 2 hour, 3 hour, 4 hour, 5 hour, 6 hour, 7 hour, 8 hour, 9 hour, 10 hour, 11 hour, 12 hour, 13 hour, 14 hour 15 hour, 16 hour, 17 hour, 18 hour, 19 hour, 20 hour, 21 hour, 22 hour, 23 hour, 1 day, 2 day, 3 day, 4 day, 5 day, 6 day, 7 day, 8 day, 9 day, 10 day, 11 day, 12 day, 13 day, 14 day, 15 day, 16 day, 17 day, 18 day, 19 day, 20 day, 21 day, 22 day, 23 day, 24 day, 25 day, 26 day, 27 day, 28 day, or more) in vitro or in vivo (e.g., following administration to a subject (e.g., a human)). For example, the PGDM1400 variant antibodies or antigen-binding fragments thereof described herein may exhibit a half-life of at least about 1 hour in vivo (e.g., in a fluid, such as blood) following administration (e.g., intravenous administration) to a subject (e.g., a human).

The PGDM1400 variant antibodies or antigen-binding fragments thereof described herein may bind to a parental PGDM1400 anti-idiotype (ID) antibody. The PGDM1400 variant antibodies or antigen-binding fragments thereof described herein may exhibit the same affinity (e.g., binding affinity) for the parental PGDM1400 anti-ID antibody as the parental PGDM1400 antibody or have an affinity (e.g., binding affinity) for the parental PGDM1400 anti-ID antibody that is about ±10% of the affinity exhibited by the parental PGDM1400 antibody.

IV. Production of the PGDM1400 Antibody Variants

The PGDM1400 antibody variant or antigen-binding fragment thereof described herein may be in the form of a single-chain polypeptide, such as a scFv fragment. Single chain polypeptides may alternatively contain one or more CDRs described herein covalently bound to one another using conventional bond-forming techniques known in the art, for instance, by an amide bond, a thioether bond, a carbon-carbon bond, or by a linker, such as a peptide linker or a linker formed by nucleophilic substitution of a multivalent electrophile (e.g., a bis(bromomethyl) arene derivative, such as a bis(bromomethyl)benzene or bis(bromomethyl)pyridine) described herein or known in the art.

Single-chain polypeptides can be produced by a variety of recombinant and synthetic techniques, such as by recombinant gene expression or solid-phase peptide synthesis procedures described herein or known in the art. For instance, one of skill in the art can design polynucleotides encoding, e.g., two or more CDRs operably linked to one another in frame so as to produce a continuous, single-chain peptide containing these CDRs. Optionally, the CDRs may be separated by a spacer, such as by a framework region (e.g., a framework sequence described herein or a framework region of a germline consensus sequence of a human antibody) or a flexible linker, such as a poly-glycine or glycine/serine linker described herein or known in the art. When produced by chemical synthesis methods, native chemical ligation can optionally be used as a strategy for the synthesis of long peptides (e.g., greater than 50 amino acids). Native chemical ligation protocols are known in the art and have been described, e.g., by Dawson et al. (Science, 266:776-779, 1994); incorporated herein by reference. A detailed description of techniques for the production of single-chain polypeptides, full-length antibodies, and antibody fragments is provided in the sections that follow.

The PGDM1400 antibody variant or antigen-binding fragment thereof described herein can be prepared by any of a variety of established techniques. For instance, an antibody or antigen-binding fragment thereof described herein can be prepared by recombinant expression of immunoglobulin light and heavy chain genes in a host cell. To express an antibody recombinantly, a host cell can be transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel et al., eds., Greene Publishing Associates, 1989), and in U.S. Pat. No. 4,816,397; the disclosures of each of which are incorporated herein by reference.

Expression Vectors

Some methods for producing a PGDM1400 antibody variant or antigen-binding fragment thereof described herein involve expression in mammalian cells, although recombinant proteins can also be produced using insect cells, yeast, bacteria, or other cells under the control of appropriate promoters. Mammalian expression vectors may include non-transcribed elements such as an origin of replication, a suitable promoter and enhancer, and other 5' or 3' flanking non-transcribed sequences, and 5' or 3' non-translated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, Molecular Cloning: A Laboratory Manual (Fourth Edition), Cold Spring Harbor Laboratory Press 2012.

Various mammalian cell culture systems can be employed to express and manufacture recombinant protein. Examples of mammalian expression systems include CHO cells, COS cells, HEK293, HeLA and BHK cell lines. Processes of culturing host cell for production of protein therapeutics are described in Zhou and Kantardjieff (Eds.), Mammalian Cell Cultures for Biologics Manufacturing (Advances in Biochemical Engineering/Biotechnology), Springer 2014.

Viral genomes also provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments described herein include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030); the disclosures of each of which are incorporated herein by reference.

Genome Editing Techniques

In addition to viral vectors, a variety of additional methods have been developed for the incorporation of genes, e.g., those encoding antibody light and heavy chains, single-chain polypeptides, single-chain variable fragments (scFvs), tandem scFvs, Fab domains, $F(ab')_2$ domains, diabodies, and triabodies, among others, into the genomes of target cells for polypeptide expression. One such method that can be used for incorporating polynucleotides encoding antibody variants, or antigen-binding fragments thereof (e.g., single-chain polypeptides, antibodies, antigen-binding fragments thereof, or constructs), into prokaryotic or eukaryotic cells includes transposons. Transposons are polynucleotides that encode transposase enzymes and contain a polynucleotide sequence or gene of interest flanked by excision sites at the 5' and 3' positions. Once a transposon has been delivered into a cell, expression of the transposase gene commences and results in active enzymes that cleave the gene of interest from the transposon. This activity is mediated by the site-specific recognition of transposon excision sites by the transposase. In some embodiments, these excision sites may be terminal repeats or inverted terminal repeats. Once excised from the transposon, the gene of interest can be integrated into the genome of a prokaryotic or eukaryotic cell by transposase-catalyzed cleavage of similar excision sites that exist within nuclear genome of the cell. This allows the gene encoding the antibody variant described in the invention or fragment or domain thereof to be inserted into the cleaved nuclear DNA at the excision sites, and subsequent ligation of the phosphodiester bonds that join the gene of interest to the DNA of the prokaryotic or eukaryotic cell genome completes the incorporation process. In some embodiments, the transposon may be a retrotransposon, such that the gene encoding the antibody is first transcribed to an RNA product and then reverse-transcribed to DNA before incorporation in the prokaryotic or eukaryotic cell genome. Exemplary transposon systems include the piggybac transposon (described in detail in WO 2010/085699) and the sleeping beauty transposon (described in detail in US20050112764); the disclosures of each of which are incorporated herein by reference.

Another useful method for the integration of nucleic acid molecules encoding the antibody or antigen-binding fragments thereof (e.g., single-chain polypeptides, antibodies, or antigen-binding fragments thereof) into the genome of a prokaryotic or eukaryotic cell is the clustered regularly interspaced short palindromic repeats (CRISPR)/Cas system, which is a system that originally evolved as an adaptive defense mechanism in bacteria and archaea against infection by viruses. The CRISPR/Cas system consists of palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al., Nat. Biotech., 31:227-229, 2013) and can be used as an efficient means of site-specifically editing eukaryotic or prokaryotic genomes in order to cleave DNA prior to the incorporation of a polynucleotide encoding a PGDM1400 antibody variant (e.g., single-chain polypeptides, antibodies, or antigen-binding fragments thereof) described herein. The use of CRISPR/Cas to modulate gene expression has been described in U.S. Pat. No. 8,697,359, the disclosure of which is incorporated herein by reference.

Alternative methods for site-specifically cleaving genomic DNA prior to the incorporation of a polynucleotide encoding an antibody or antibody fragment described herein include the use of zinc finger nucleases and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. Zinc finger nucleases and TALENs for use in genome editing applications are described in Urnov et al. (Nat. Rev. Genet., 11:636-646, 2010); and in Joung et al., (Nat. Rev. Mol. Cell. Bio. 14:49-55, 2013); incorporated herein by reference. Additional genome editing techniques that can be used to incorporate polynucleotides encoding antibodies described herein into the genome of a prokaryotic or eukaryotic cell include the use of ARCUS™ meganucleases that can be rationally designed so as to site-specifically cleave genomic DNA. The use of these enzymes for the incorporation of polynucleotides encoding antibodies (e.g., antibodies, antigen-binding fragments thereof, or constructs) described herein into the genome of a prokaryotic or eukaryotic cell is particularly advantageous in view of the structure-activity relationships that have been established for such enzymes. Single-chain meganucleases can thus be modified at certain amino acid positions in order to create nucleases that selectively cleave DNA at desired locations. These single-chain nucleases have been described extensively, e.g., in U.S. Pat. Nos. 8,021,867 and 8,445,251; the disclosures of each of which are incorporated herein by reference.

Polynucleotide Sequence Elements

To express antibodies (e.g., single-chain polypeptides, antibodies, antigen-binding fragments thereof, or constructs) described herein, polynucleotides encoding partial or full-length light and heavy chains, e.g., polynucleotides that encode one or more, or all, of the CDR sequences of a PGDM1400 antibody variant or antigen-binding fragment thereof described herein can be inserted into an expression vector such that the nucleic acid molecules encoding the PGDM1400 antibody variant sequences are operatively linked to transcriptional and translational control sequences. The expression vector and expression control sequences are chosen to be compatible with the expression host cell used. Polynucleotides encoding the light chain and the heavy chain domains of a PGDM1400 antibody variant or fragment thereof described herein can be inserted into separate vectors, or, optionally, both polynucleotides can be incorporated into the same expression vector using established techniques described herein or known in the art.

In addition to polynucleotides encoding the heavy and light chains of a PGDM1400 antibody variant (or a polynucleotide encoding a single-chain polypeptide, an antibody fragment, such as a scFv molecule, or a construct described herein), the recombinant expression vectors described herein may carry regulatory sequences that control the expression of the antibody chain polynucleotides in a host cell. The design of the expression vector, including the selection of regulatory sequences, may depend on such factors as the choice of the host cell to be transformed or the level of expression of protein desired. For instance, suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Viral regulatory elements, and sequences thereof, are described in detail, for instance, in U.S. Pat. Nos. 5,168,062, 4,510,245, and 4,968,615, the disclosures of each of which are incorporated herein by reference.

In addition to the antibody heavy and light chain polynucleotides and regulatory sequences, the recombinant expression vectors described herein can carry additional sequences, such as sequences that regulate replication of the vector in host cells (e.g., origins of replication) and selectable marker genes. A selectable marker gene facilitates selection of host cells into which the vector has been introduced (see e.g., U.S. Pat. Nos. 4,399,216, 4,634,665 and 5,179,017). For example, typically the selectable marker gene confers resistance to cytotoxic drugs, such as G418, puromycin, blasticidin, hygromycin or methotrexate, to a host cell into which the vector has been introduced. Suitable selectable marker genes include the dihydrofolate reductase (DHFR) gene (for use in DHFR" host cells with methotrexate selection/amplification) and the neo gene (for G418 selection). In order to express the light and heavy chain domains of a PGDM1400 antibody or antigen-binding fragment thereof, the expression vector(s) containing polynucleotides encoding the heavy and light chain domains can be transfected into a host cell by standard techniques.

V. Antiretroviral Agents (ARVs) for Use in Combination with PGDM1400 Variant Antibodies In certain instances, a PGDM1400 variant antibody or fragment thereof featured herein may be used in combination with one or more (e.g., 2, 3, 4, 5, 6, 7, 8, 9, 10, or more) antiretroviral agents (ARVs), such as, without limitation, any one or more ARVs set forth in Table 3 below.

TABLE 3

| Antiretroviral Agents | |
|---|---|
| Generic Name (Brand Name) | Class |
| efavirenz, emtricitabine and tenofovir disoproxil fumarate (Atripla) | Multi-class |
| emtricitabine, rilpivirine, and tenofovir disoproxil fumarate (Complera) | Multi-class |
| elvitegravir, cobicistat, emtricitabine, tenofovir disoproxil fumarate (Stribild) | Multi-class |
| lamivudine and zidovudine (Combivir) | NRTI |
| emtricitabine, FTC (Emtriva) | NRTI |
| lamivudine, 3TC (Epivir) | NRTI |
| abacavir and lamivudine (Ebzicom) | NRTI |
| zalcitabine, dideoxycytidine, ddC (Hivid) | NRTI |
| zidovudine, azidothymidine, AZT, ZDV (Retrovir) | NRTI |
| abacavir, zidovudine, and lamivudine (Trizivir) | NRTI |
| tenofovir disoproxil fumarate and emtricitabine (Truvada) | NRTI |
| enteric coated didanosine, ddI EC (Videx EC) | NRTI |
| didanosine, dideoxyinosine, ddI (Videx) | NRTI |
| tenofovir disoproxil fumarate, TDF (Viread) | NRTI |
| stavudine, d4T (Zerit) | NRTI |
| abacavir sulfate, ABC (Ziagen) | NRTI |
| Rilpivirine (Edurant) | NNRTI |
| Etravirine (Intelence) | NNRTI |
| delavirdine, DLV (Rescriptor) | NNRTI |
| efavirenz, EFV (Sustiva) | NNRTI |
| nevirapine, NVP (Viramune) | NNRTI |
| nevirapine, NVP (Viramune XR) | NNRTI |
| amprenavir, APV (Agenerase) | PI |
| tipranavir, TPV (Aptivus) | PI |
| indinavir, IDV (Crixivan) | PI |

TABLE 3-continued

| Antiretroviral Agents | |
|---|---|
| Generic Name (Brand Name) | Class |
| saquinavir (Fortovase) | PI |
| saquinavir mesylate, SQV (Invirase) | PI |
| lopinavir and ritonavir, LPV/RTV (Kaletra) | PI |
| Fosamprenavir Calcium, FOS-APV (Lexiva) | PI |
| ritonavir, RTV (Norvir) | PI |
| Darunavir (Prezista) | PI |
| atazanavir sulfate, ATV (Reyataz) | PI |
| nelfinavir mesylate, NFV (Viracept) | PI |
| enfuvirtide, T-20 (Fuzeon) | Fusion Inhibitor |
| maraviroc (Selzentry) | Entry Inhibitor - CCR5 co-receptor antagonist |
| raltegravir (Isentress) | HIV integrase strand transfer inhibitors |
| dolutegravir (Tivicay) | HIV integrase strand transfer inhibitors |

One or more of the above ARVs may be used (e.g., administered to a subject in need thereof) in combination with a PGDM1400 variant antibody or fragment thereof featured herein, and, optionally, one or more (e.g., 2, 3, 4, 5, 6, 7, 8, 9, 10, or more) HIV-specific broadly neutralizing antibody (bnAb), such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400). One or more of the above ARVs may be administered to a subject (e.g., a human), either alone, or in combination with the bnAb, prior to, concurrently with, and/or subsequent to administration of the antibody (e.g., a PGDM1400 variant antibody or fragment thereof) featured herein.

VI. Immunomodulators for Use in Combination with PGDM1400 Variant Antibodies

A PGDM1400 variant antibody or fragment thereof featured herein may be used in combination with one or more (e.g., 2, 3, 4, 5, 6, 7, 8, 9, 10, or more) immunomodulators, such as, without limitation, any one or more immunomodulators set forth in Table 4 below.

TABLE 4

| Exemplary Immunomodulators Drug Name |
|---|
| AS-101 |
| Bropirimine |
| Acemannan |
| CL246,738 |
| EL10 |
| FP-21399 |
| Gamma Interferon |
| Granulocyte Macrophage Colony Stimulating Factor |
| HIV Core Particle Immunostimulant |
| Interleukin-2 (IL-2) |
| Immune Globulin Intravenous (human) |
| IMREG-1 |
| IMREG-2 |
| Imuthiol Diethyl Dithio Carbamate |
| Alpha-2 Interferon |
| Methionine-Enkephalin |
| MTP-PE Muramyl-Tripeptide |
| Granulocyte Colony Stimulating Factor |
| a gp120-depleted, inactivated $HZ_{321}$ virus (e.g., REMUNE ™) |
| rCD4-IgG hybrids |
| Recombinant Soluble Human CD4 |
| SK&F106528 Soluble T4 |
| Thymopentin |

TABLE 4-continued

| Exemplary Immunomodulators Drug Name |
|---|
| Tumor Necrosis Factor |
| Infliximab |

One or more of the above immunomodulators may be used (e.g., administered to a subject in need thereof) in combination with a PGDM1400 variant antibody or fragment thereof featured herein, and, optionally, one or more (e.g., 2, 3, 4, 5, 6, 7, 8, 9, 10, or more) HIV-specific bnAb, such as a CD4bs-specific antibody (e.g., 3BNC117 or VRC07-523), an N332 glycan-dependent antibody (e.g., PGT121, or a variant thereof), a V2-specific antibody (e.g., CAP256-VRC26 and/or the parental PGDM1400), and/or one or more (e.g., 2, 3, 4, 5, 6, 7, 8, 9, 10, or more) ARVs. One or more of the above immunomodulators may be administered to a subject (e.g., a human), either alone, or in combination with the bnAb and/or the ARV, prior to, concurrently with, and/or subsequent to administration of the PGDM1400 variant antibody or antigen-binding fragment thereof featured herein.

VII. Reservoir Activators for Use in Combination with PGDM1400 Variant Antibodies A PGDM1400 variant antibody or fragment thereof featured herein may be used in combination with one or more (e.g., 2, 3, 4, 5, 6, 7, 8, 9, 10, or more) reservoir activators, such as, without limitation, any one or more reservoir activators described by Spivak and Planelles (Annu Rev Med, 69:421-436, 2018), Stoszko et al (EBioMedicine, 3:108-121, 2016), and Delagreverie et al (Open Forum Infectious Diseases, DOI: 10.1093/ofid/ofw189); incorporated herein by reference. Examples of reservoir activators that may be used in combination with a PGDM1400 variant antibody or fragment thereof featured herein are set forth in Table 5 below.

TABLE 5

Exemplary reservoir activators

| Class of agents | Agents |
|---|---|
| PKC agonists | (i) Phorbol esters, including phorbol 12-myristate 13-acetate (PMA), prostratin and 12-deoxyphorbol 13-phenylacetate (DPP);<br>(ii) Macrocyclic lactones including bryostatin-1 and analogs<br>(iii) Diterpenes, including ingenol compounds |
| Cytokines and chemokines | IL-7, IFN-α, IL-15 superagonist ALT-803 (IL-15N72D + IL-15RαSu/Fc fusion protein) |
| Toll-like receptor (TLR) agonists | (i) TLR 1/2 agonists, including Pam3CSK4<br>(ii) TLR3 agonists, including Poly-ICLC<br>(iii) TLR5 agonists, including flagellin<br>(iv) TLR7 agonists, including GS-9620<br>(v) TLR9 agonists, including MGN1703 and CpG7909 |
| Immune checkpoint inhibitors | Anti-PD-1 monoclonal antibodies, anti-PD-1 ligand (PD-L1) monoclonal antibodies, anti-CTLA-4 monoclonal antibodies |
| HDAC inhibitors | romidepsin, vorinostat, belinostat, LAQ824, panobinostat, entinostat, CI994, mocetinostat |
| Small molecules | (i) Disulfiram<br>(ii) Benzotriazole derivatives, including 3-Hydroxy-1,2,3-benzotriazin-4((3H)-one (HO-DHBt)<br>(iii) SMAC mimetics<br>(iv) BRG-Brahma Associated Factor (BAF) inhibitors, including caffeic acid phenethyl ester and pyrimethamine |

One or more of the above reservoir activators may be used (e.g., administered to a subject in need thereof) in combination with a PGDM1400 variant antibody or fragment thereof featured herein, and, optionally, one or more (e.g., 2, 3, 4, 5, 6, 7, 8, 9, 10, or more) HIV-specific bnAb, such as a CD4bs-specific antibody (e.g., 3BNC117 or VRC07-523), an N332 glycan-dependent antibody (e.g., PGT121, or a variant thereof), a V2-specific antibody (e.g., CAP256-VRC26 and/or the parental PGDM1400), one or more (e.g., 2, 3, 4, 5, 6, 7, 8, 9, 10, or more) ARVs, and/or one or more (e.g., 2, 3, 4, 5, 6, 7, 8, 9, 10, or more) immunomodulators. One or more of the above reservoir activators may be administered to a subject (e.g., a human), either alone, or in combination with the bnAb, the ARV, and/or the immunomodulator, prior to, concurrently with, and/or subsequent to administration of the PGDM1400 variant antibody or fragment thereof featured herein.

VIII. Therapeutic Methods

The PGDM1400 variant antibodies or fragments thereof described herein can be administered to a subject in need thereof to treat or block HIV infection in the subject. In one or more methods described herein, the featured PGDM1400 variant antibody or fragment thereof can be administered, either alone, or in combination with one or more of a bnAb, ARV, reservoir activator and/or immunomodulator, to a subject (e.g., a human) in need thereof to cure HIV infection in the subject. In particular, featured are methods of treating a subject (e.g., a human) infected with HIV (e.g., HIV-1), in which the methods include administering to the subject one or more of the PGDM1400 variant antibodies or antigen-binding fragments thereof described hereinabove. These methods are supported by the findings that the PGDM1400 variant antibodies or fragments thereof described herein are capable of neutralizing pseudoviruses of HIV, such as SC422661.8, RHPA4259.7, Du172.17, BB1012-11.TC21, CNE52, 0260.v5.c36, 263-8, SC05.8C11.2344, X1193_c1, Ce1176_A3, AC10.0.29, and 6952.v1.c20.

Included are methods of blocking an HIV (e.g., HIV-1) infection in a subject (e.g., a human) at risk of HIV transmission by administering one or more of the PGDM1400 variant antibodies and/or antigen binding fragments thereof to the subject. For example, in one aspect, the subject may be a fetus of an HIV-infected pregnant female and the method includes administering to the HIV-infected pregnant female one or more of the PGDM1400 variant antibodies or antigen-binding fragments thereof described hereinabove, thereby blocking the HIV infection in the fetus. In other instances, the subject is a newborn having an HIV-infected mother, a subject at risk of HIV transmission following a needlestick injury, or a subject at risk of HIV transmission following a sexual exposure to one or more HIV-infected individuals.

In instances when the subject is a fetus of an HIV-infected pregnant female, the HIV-infected pregnant female can be administered one or more of the PGDM1400 variant antibodies or antigen-binding fragments thereof described hereinabove following manifestation of one or more symptoms associated with pregnancy (e.g., a missed period, tender or swollen breasts, nausea with or without vomiting, increased urination, fatigue, and/or uncharacteristic food aversions or cravings), following a diagnosis of pregnancy, and/or in the third trimester of pregnancy, in order to block an HIV infection in the fetus.

In instances when the subject is a newborn having an HIV-infected mother, the newborn can be administered one or more of the PGDM1400 variant antibodies or antigen-binding fragments thereof described hereinabove peripartum and/or postpartum, for example, prior to, during, and/or following breastfeeding from the HIV-infected mother, in order to block an HIV infection in the newborn.

In instances when the subject is at risk of HIV transmission following a needlestick injury, the subject can be administered one or more of the PGDM1400 variant antibodies or antigen-binding fragments thereof described hereinabove less than 3 days following the needlestick injury, for example, 1, 2, 3, 4, 5, 6, 7, 8, 9, 10, 15, 20, 30, 35, 40, 45, 50, 55, or 60 minutes, 2, 4, 6, 10, 15, or 24 hours, 1.5, 2, or 2.5 days following the needlestick injury, in order to block an HIV infection in the subject. Alternatively, or additionally, the subject can be administered one or more of the PGDM1400 variant antibodies or antigen-binding fragments thereof described hereinabove between 3 to 14 days following the needlestick injury, for example, 3, 4, 5, 6, 7, 8, 9, 10, 11, 12, 13, or 14 days following the needlestick injury, in order to block an HIV infection in the subject.

In instances when the subject is at risk of HIV transmission following a sexual exposure to one or more HIV-infected individuals, the subject can be administered one or more of the PGDM1400 variant antibodies or antigen-binding fragments thereof described hereinabove less than 3 days following the sexual exposure, for example, 1, 2, 3, 4, 5, 6, 7, 8, 9, 10, 15, 20, 30, 35, 40, 45, 50, 55, or 60 minutes, 2, 4, 6, 10, 15, or 24 hours, 1.5, 2, or 2.5 days following the sexual exposure, in order to block an HIV infection in the subject. Alternatively, or additionally, the subject can be administered one or more of the PGDM1400 variant antibodies or antigen-binding fragments thereof described hereinabove between 3 to 14 days following the sexual exposure, for example, 3, 4, 5, 6, 7, 8, 9, 10, 11, 12, 13, or 14 days following the sexual exposure, in order to block an HIV infection in the subject.

In any of the methods of antibody therapy described above, the subject can have an undetectable plasma viral load, such as less than 3,500 RNA copies/ml (e.g., less than 2,000 RNA copies/ml, e.g., less than 400 RNA copies/ml, e.g., less than 50 RNA copies/ml, e.g., less than 1 RNA copy/ml), prior to commencement of antibody therapy. In such instances, the subject may already be on ARV. However, ARV alone, in contrast to the PGDM1400 variant antibodies or antigen-binding fragments thereof described hereinabove, is unable to reduce tissue reservoirs of the virus. Accordingly, the methods of the invention feature administration of one or more of the PGDM1400 variant antibodies or antigen-binding fragments thereof described hereinabove, alone or in combination with one or more (e.g., 2, 3, 4, 5, 6, 7, 8, 9, 10, or more) ARV, and/or one or more (e.g., 2, 3, 4, 5, 6, 7, 8, 9, 10, or more) HIV-specific bnAb (such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), as described in detail below, to treat a subject (e.g., a human) infected with HIV (e.g., HIV-1) or block an HIV infection in a subject at risk of HIV transmission, based, at least in part, on the finding that the PGDM1400 variant antibodies or fragments thereof described hereinabove are capable of neutralizing pseudoviruses of HIV, such as RHPA4259.7, Du172.17, CNE52, 0260.v5.c36, SC05.8C11.2344, Ce1176_A3, SC422661.8, BB1012-11.TC21, 263-8, X1193_c1, AC10.0.29, and 6952.v1.c20. Preferably, the subject either maintains or achieves an undetectable plasma viral load for at least about 2 months (e.g., at least about 3, 4, 5, 6, 7, 8, 9, 10, or 11 months, or 1, 2, 3, 4, 5, 6, 7, 8, 9, 10, 11, 12, 13, 14, 15, 16, 17, 18, 19, or 20 years) following administration of the PGDM1400 variant antibodies or fragments thereof described hereinabove. The reduction in plasma viral load may be in the absence of an ART, e.g., for a period of at least about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more after administration of the PGDM1400 variant antibody or antigen-binding fragment thereof.

In any of the methods described above, further administration of an immunomodulator (e.g., an agent, such as a protein or peptide, which is capable of increasing, inducing, or extending an immune response, e.g., a cell-mediated immune response and/or a humoral immune response, when administered to a subject, such as a human, e.g., a human infected with HIV or at risk of an HIV infection or transmission) is contemplated. For example, one or more immunomodulators (e.g., 2, 3, 4, 5, 6, 7, 8, 9, 10, or more immunomodulators) can be administered in conjunction with, e.g., prior to, concurrently with, subsequent to, or within the context of a treatment regimen that includes administration of a PGDM1400 variant antibody or fragment thereof described hereinabove.

In any of the methods described above, further administration of a reservoir activator (e.g., one or more reservoir activators selected from Table 5) is contemplated. For example, one or more reservoir activators (e.g., 2, 3, 4, 5, 6, 7, 8, 9, 10, or more reservoir activators) can be administered in conjunction with, e.g., prior to, concurrently with, subsequent to, or within the context of a treatment regimen that includes administration of a PGDM1400 variant antibody or fragment thereof described hereinabove.

In any of the methods described above, administration of one or more of the PGDM1400 variant antibodies or antigen-binding fragments thereof described hereinabove, alone or in combination with one or more (e.g., 2, 3, 4, 5, 6, 7, 8, 9, 10, or more) HIV-specific bnAb (such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), one or more (e.g., 2, 3, 4, 5, 6, 7, 8, 9, 10, or more) ARVs, one or more (e.g., 2, 3, 4, 5, 6, 7, 8, 9, 10, or more) reservoir activators, and/or one or more (e.g., 2, 3, 4, 5, 6, 7, 8, 9, 10, or more) immunomodulators may: (i) reduce proviral DNA to below about 1,000 DNA copies/$10^6$ cells (e.g., below about 900 DNA copies/$10^6$ cells, below about 800 DNA copies/$10^6$ cells, below about 700 DNA copies/$10^6$ cells, below about 600 DNA copies/$10^6$ cells, below about 500 DNA copies/$10^6$ cells, below about 400 DNA copies/$10^6$ cells, below about 300 DNA copies/$10^6$ cells, below about 200 DNA copies/$10^6$ cells, below about 100 DNA copies/$10^6$ cells, below about 90 DNA copies/$10^6$ cells, below about 80 DNA copies/$10^6$ cells, below about 70 DNA copies/$10^6$ cells, below about 60 DNA copies/$10^6$ cells, below about 50 DNA copies/$10^6$ cells, below about 40 DNA copies/$10^6$ cells, below about 30 DNA copies/$10^6$ cells, below about 20 DNA copies/$10^6$ cells, below about 10 DNA copies/$10^6$ cells, below about 9 DNA copies/$10^6$ cells, below about 8 DNA copies/$10^6$ cells, below about 7 DNA copies/$10^6$ cells, below about 6 DNA copies/$10^6$ cells, below about 5 DNA copies/$10^6$ cells, below about 4 DNA copies/$10^6$ cells, below about 3 DNA copies/$10^6$ cells, below about 2 DNA copies/$10^6$ cells, below about 1 DNA copy/$10^6$ cells, or to an undetectable level) in a tissue (e.g., lymph node tissue, gastrointestinal tissue, peripheral blood) of the subject relative to an untreated control; (ii) increase HIV-specific cell-mediated immune response and/or humoral immune response in the subject relative to an untreated control; (iii) decrease viral replication in the subject relative to an untreated control; and/or (iv) reduce the plasma viral load to less than about 3,500 RNA copies/ml (e.g., less than about 3,000 RNA copies/ml, less than about 2,500 RNA copies/ml, less than about 2,000 RNA copies/ml, less than about 1,500 RNA copies/ml, less than about 1,000 RNA copies/ml, less than about 550 RNA copies/ml, less than about 500 RNA copies/ml, less than about 450 RNA copies/ml, less than about 400 RNA copies/ml, less than about 350 RNA copies/ml, less than about 300 RNA copies/ml, less than about 250 RNA copies/ml, less than about 200 RNA copies/ml, less than about 150 RNA copies/ml, less than about 100 RNA copies/ml, less than about 50 RNA copies/ml, less than about 40 RNA copies/ml, less than about 30 RNA copies/ml, less than about 20 RNA copies/ml, less than about 10 RNA copies/ml, less than about 9 RNA copies/ml, less than about 8 RNA copies/ml, less than about 7 RNA copies/ml, less than about 6 RNA copies/ml, less than about 5 RNA copies/ml, less than about 4 RNA copies/ml, less than about 3 RNA copies/ml, less than about 2 RNA copies/ml, less than about 1 RNA copy/ml, or to an undetectable level) relative to an untreated control. In some instances, following administration of one or more of the PGDM1400 variant antibodies or antigen-binding fragments thereof described hereinabove, alone or in combination with one or more (e.g., 2, 3, 4, 5, 6, 7, 8, 9, 10, or more) HIV-specific bnAb (such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), one or more (e.g., 2, 3, 4, 5, 6, 7, 8, 9, 10, or more) ARVs, one or more (e.g., 2, 3, 4, 5, 6, 7, 8, 9, 10, or more) reservoir activators, and/or one or more (e.g., 2, 3, 4, 5, 6, 7, 8, 9, 10, or more) immunomodulators, the subject has an undetectable plasma viral load for at least about 2 months (e.g., at least about 3 months, at least about 4 months, at least about 5 months, at least about 6 months, at least about 7 months, at least about 8 months, at least about 9 months, at least about 10 months, at least about 11 months, at least about 1 year, at least about 2 years, at least about 3 years, at least about 4 years, at least about 5 years, at least about 6 years, at least about 7 years, at least about 8 years, at least about 9 years, at least about 10 years, at least about 11 years, at least about 12 years, at least about 13 years, at least about 14 years, at least about 15 years, at least about 16 years, at least about 17 years, at least about 18 years, at least about 19 years, at least about 20 years, or more).

As described below in more detail, in any of the methods described above, the HIV therapy (e.g., HIV-1 therapy) may be concluded following administration of at least one dose (e.g., 2, 3, 4, 5, 6, 7, 8, 9, 10, or more doses) of the PGDM1400 variant antibody or antigen-binding fragment thereof described hereinabove, alone or in combination with one or more (e.g., 2, 3, 4, 5, 6, 7, 8, 9, 10, or more) HIV-specific bnAb (such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), one or more (e.g., 2, 3, 4, 5, 6, 7, 8, 9, 10, or more) ARVs, one or more (e.g., 2, 3, 4, 5, 6, 7, 8, 9, 10, or more) reservoir activators, and/or one or more (e.g., 2, 3, 4, 5, 6, 7, 8, 9, 10, or more) immunomodulators, following a duration of time post-therapy (e.g., at least about two months or longer). The subject (e.g., a human infected with HIV or at risk of HIV transmission) can be monitored post-therapy to confirm that they exhibit and/or maintain virologic control in the absence of any intervening therapies, which, optionally, can be determined based upon measurements made from a biological sample of the subject (e.g., a measurement of proviral DNA level in a tissue and/or plasma viral load). If the subject exhibits and/or maintains virologic control during this post-therapy period, the subject may be taken off one or more, or all, HIV therapies indefinitely or until such time as the subject begins to exhibit loss of virologic control.

IX. Methods of Administration and Dosage

For any of the methods describe above, the one or more (e.g., 2, 3, 4, 5, 6, 7, 8, 9, 10, or more) PGDM1400 variant antibodies or antigen-binding fragments thereof described hereinabove can be formulated, dosed, and administered in a fashion consistent with good medical practice. Antibody therapy may be performed alone or in conjunction with another therapy (e.g., ARV therapy or administration of a reservoir activator), and may be provided at home, the doctor's office, a clinic, a hospital's outpatient department, or a hospital. Antibody therapy optionally begins at a hospital so that the doctor can observe the therapy's effects closely and make any adjustments that are needed, or it may begin on an outpatient basis.

The dosage administered can be selected based on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., mucosal cells, epithelial cells, such as blood vessel epithelial cells, nasal epithelial cells, or pulmonary epithelial cells). Additionally, pharmacogenomic (the effect of genotype on the pharmacokinetic, pharmacodynamic, or efficacy profile of a therapeutic) information about a particular subject may affect the dosage used. Antibody therapy of the invention is preferably administered in an amount that provides a sufficient level of one or more of the PGDM1400 variant antibodies or antigen-binding fragments thereof to yield a therapeutic effect in the subject without undue adverse physiological effects caused by treatment.

An PGDM1400 variant antibody or antigen-binding fragment thereof described hereinabove can be administered to a subject (e.g., a human infected with HIV and/or at risk of HIV transmission) intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularly, mucosally, intrapericardially, intraumbilically, intraocularally, orally, topically, locally, by inhalation, by injection, by infusion, by continuous infusion, by localized perfusion bathing target cells directly, by catheter, by lavage, in cremes, or in lipid compositions, in accord with known methods. For example, the PGDM1400 variant antibody or antigen-binding fragment thereof described hereinabove can be administered by infusion, such as by continuous infusion (e.g., intravenously). Alternatively, it is envisioned that the PGDM1400 variant antibody or antigen-binding fragment thereof described hereinabove may be delivered by gene therapy.

For any of the methods described above, a single dose of a PGDM1400 variant antibody or antigen-binding fragment thereof described hereinabove can be administered to the subject. The single dose may be of a single PGDM1400 variant antibody or antigen-binding fragment thereof described hereinabove or of more than one antibody (i.e., an antibody cocktail including multiple antibodies or antigen-binding fragments thereof described hereinabove). In some instances, HIV therapy (e.g., HIV-1 therapy) may be concluded following the administration of the single dose of the PGDM1400 variant antibody or fragment thereof described hereinabove. In some instances, the single dose may be administered along with one or more (e.g., 2, 3, 4, 5, 6, 7, 8, 9, 10, or more) ARVs, such as one or more of the ARVs listed in Table 3 above, wherein the ARV is administered concurrently with, prior to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour prior to), and/or subsequent to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour subsequent to) the single dose of the PGDM1400 variant antibody or fragment thereof described hereinabove. Accordingly, HIV therapy can, in some instances, be concluded following the administration of the ARV subsequent to the single dose of the PGDM1400 variant antibody or fragment thereof described hereinabove.

Alternatively, or additionally, the single dose may be administered along with a one or more (e.g., 2, 3, 4, 5, 6, 7, 8, 9, 10, or more) HIV-specific bnAb (such as a CD4bs-specific antibody (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), wherein the HIV-specific bnAb is administered concurrently with, prior to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour prior to), and/or subsequent to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour subsequent to) the single dose of the PGDM1400 variant antibody or fragment thereof described hereinabove, alone, or in combination with one or more ARV. Accordingly, HIV therapy can, in some instances, be concluded following the administration of the HIV-specific bnAb (e.g., 3BNC117, VRC07-523, PGT121 or variant thereof, CAP256-VRC26, or the parental PGDM1400) subsequent to the single dose of the PGDM1400 variant antibody or fragment thereof described hereinabove.

Alternatively, or additionally, the single dose may be administered along with a one or more (e.g., 2, 3, 4, 5, 6, 7, 8, 9, 10, or more) immunomodulators (e.g., one or more immunomodulators selected from Table 4), wherein the immunomodulator is administered concurrently with, prior to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour prior to), and/or subsequent to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour subsequent to) the single dose of the PGDM1400 variant antibody or fragment thereof described hereinabove, alone, or in combination with one or more ARV, and/or HIV-specific bnAb (e.g., 3BNC117, VRC07-523, PGT121 or variant thereof, CAP256-VRC26, or the parental PGDM1400). Accordingly, HIV therapy can, in some instances, be concluded following the administration of the immunomodulator subsequent to the single dose of the PGDM1400 variant antibody or fragment thereof described hereinabove.

Alternatively, or additionally, the single dose may be administered along with a one or more (e.g., 2, 3, 4, 5, 6, 7, 8, 9, 10, or more) reservoir activators (e.g., one or more reservoir activators selected from Table 5), wherein the reservoir activator is administered concurrently with, prior to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour prior to), and/or subsequent to (e.g., about 1 year, 9 months, 6 months, 3 months, 1 month, 3 weeks, 2 weeks, 1 week, 5 days, 3 days, 1 day, 18 hours, 12 hours, 6 hours, or 1 hour subsequent to) the single dose of the PGDM1400 variant antibody or fragment thereof described hereinabove, alone, or in combination with one or more ARV, HIV-specific bnAb (e.g., 3BNC117, VRC07-523, PGT121 or variant thereof, CAP256-VRC26, or the parental PGDM1400), and/or immunomodulators. Accordingly, HIV therapy can, in some instances, be concluded following the administration of the reservoir activators subsequent to the single dose of the PGDM1400 variant antibody or fragment thereof described hereinabove.

In other instances, the method includes administering a first regimen including one or more doses (e.g., 2, 3, 4, 5, 6, 7, 8, 9, 10, or more doses) of the PGDM1400 variant antibody or fragment thereof described hereinabove and a second regimen including one or more doses (e.g., 2, 3, 4, 5, 6, 7, 8, 9, 10, or more doses) of the PGDM1400 variant antibody or fragment thereof described hereinabove, wherein the second regimen is administered at least about 2 months (e.g., at least about 3, 4, 5, 6, 7, 8, 9, 10, or 11 months, or 1, 2, 3, 4, 5, 6, 7, 8, 9, 10, 11, 12, 13, 14, 15, 16, 17, 18, 19, or 20 years) after the first regimen. The duration of time between the first and second regimens is preferably a longer duration of time than necessary for viral rebound to occur in a subject (e.g., a human) infected with HIV (e.g., HIV-1) under current standard of care (e.g., ART), which is approximately two months. Thus, the second regimen of the PGDM1400 variant antibody or fragment thereof described hereinabove can be considered a maintenance dose, and in some instances, HIV therapy may be concluded following the administration of the second regimen of the PGDM1400 variant antibody or fragment thereof described hereinabove. In some instances, the method can further include administering one or more (e.g., 1, 2, 3, 4, or 5 or more) ARV, such as one or more of the ARVs listed in Table 3 above, wherein the ARV is administered concurrently with, prior to, and/or subsequent to the first regimen and/or the second regimen of the PGDM1400 variant antibody or fragment thereof described hereinabove. Accordingly, HIV therapy can, in some instances, be concluded following the administration of the ARV subsequent to the second regimen of the PGDM1400 variant antibody or fragment thereof described hereinabove. Alternatively, or additionally, the first and second regimens may be administered along with a HIV-specific bnAb, such as CD4bs-specific antibodies (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400). Accordingly, HIV therapy can, in some instances, be concluded following the administration of the HIV-specific bnAb (e.g., 3BNC117, VRC07-523, PGT121 or variant thereof, CAP256-VRC26, or the parental PGDM1400) subsequent to second regimen of the PGDM1400 variant antibody or fragment thereof described hereinabove. Alternatively, or additionally, the first and second regimens may be administered along with an immunomodulator, such as one or more of the immunomodulators listed in Table 4 above. Accordingly, HIV therapy can, in some instances, be concluded following the administration of the immunomodulator subsequent to second regimen of the PGDM1400 variant antibody or fragment thereof described hereinabove. Alternatively, or additionally, the first and second regimens may be administered along with a reservoir activator, such as one or more of the reservoir activators listed in Table 5 above. Accordingly, HIV therapy can, in some instances, be concluded following the administration of the reservoir activator subsequent to second regimen of the PGDM1400 variant antibody or fragment thereof described hereinabove.

For any of the methods described above, a PGDM1400 variant antibody or fragment thereof described hereinabove can be administered to the subject in a unit dose form or as a dose per mass or weight of the subject from about 0.01 mg/kg to about 100 mg/kg (e.g., about 0.01-0.1 mg/kg, e.g., 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The PGDM1400 variant antibody or fragment thereof described hereinabove can be administered to the subject at a dose of about 0.01-100 mg/kg (e.g., about 0.02-100 mg/kg, 0.03-100 mg/kg, 0.04-mg/kg, 0.05-100 mg/kg, 0.06-100 mg/kg, 0.07-100 mg/kg, 0.08-100 mg/kg, 0.09-100 mg/kg, 0.1-90 mg/kg, 0.1-80 mg/kg, 0.1-70 mg/kg, 0.1-60 mg/kg, 0.1-50 mg/kg, 0.5-50 mg/kg, 0.5-40 mg/kg, 0.5-30 mg/kg, 0.5-20 mg/kg, 0.5-10 mg/kg, 0.5-5 mg/kg, or 0.5-1 mg/kg) per mass or weight of the subject. For any of the methods described above, about 0.01-5000 mg (e.g., about 0.01-4500 mg, 0.01-4000 mg, 0.01-3500 mg, 0.01-3000 mg, 0.01-2500 mg, 0.01-2000 mg, 0.01-1500 mg, 0.01-1000 mg, 0.05-1000 mg, 0.1-1000 mg, 0.1-500 mg, 0.5-500 mg, 0.5-450 mg, 0.5-400 mg, 0.5-350 mg, 0.5-300 mg, 0.5-250 mg, 0.5-200 mg, 0.5-150 mg, 0.5-100 mg, 0.5-50 mg, 0.5-45 mg, 0.5-40 mg, 0.5-35 mg, 0.5-30 mg, 0.5-25 mg, 0.5-20 mg, 0.5-15 mg, 0.5-10 mg, or 1-10 mg) of the PGDM1400 variant antibody or fragment thereof described hereinabove can be administered to the subject.

A PGDM1400 variant antibody or fragment thereof described hereinabove may be administered to the subject two or more times, such as one or more times hourly, daily (e.g., once daily for up to six days), weekly, every two weeks, every three weeks, every four weeks, monthly, every two months, every three months, every six months, or every year. The method may further include administering a second dose of the PGDM1400 variant antibody or fragment thereof described hereinabove to the subject about one week, two weeks, three weeks, four weeks, or five weeks after administration of a first dose of the PGDM1400 variant antibody or fragment thereof described hereinabove. The method may also include administering more than two doses (e.g., three, four, five, six, seven, eight, nine, ten, or more doses) of the PGDM1400 variant antibody or fragment thereof to the subject. Administration of a PGDM1400 variant antibody or fragment thereof described hereinabove can be repeated at such a frequency for a certain period of time, followed by a period without treatment. Such repeated administrations can occur over a course of therapy lasting a specified length of time (e.g., at least about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, or more).

In some of the methods of the invention, HIV (e.g., HIV-1) therapy is concluded following a determination that the proviral DNA level in tissue of the subject (as assessed, e.g., by biopsy) is reduced to an undetectable level. The method can result in a reduction of proviral DNA level in tissue of the subject relative to an amount of proviral DNA level in tissue of the subject before the administration of the PGDM1400 variant antibody or fragment thereof described hereinabove, or relative to an untreated control. For example, the proviral DNA level in tissue (e.g., lymph node tissue, gastrointestinal tissue, and/or peripheral blood) may be reduced to an undetectable level, such as below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells). Thus, a definitive end to HIV therapy can be determined based upon measurements made from a biological sample of the subject and/or time post-administration of the PGDM1400 variant antibody or fragment thereof described hereinabove.

According to any one of the methods of the invention described herein, a PGDM1400 variant antibody or fragment thereof described hereinabove can be administered as a pharmaceutical composition. The pharmaceutical composition has the antibody or antigen-binding fragment thereof alone, or in combination with one or more (e.g., 2, 3, 4, 5, 6, 7, 8, 9, 10, or more) ARV (e.g., one or more ARVs selected from Table 3), one or more (e.g., 2, 3, 4, 5, 6, 7, 8, 9, 10, or more) immunomodulators (e.g., one or more immunomodulators selected from Table 4), one or more (e.g., 2, 3, 4, 5, 6, 7, 8, 9, 10, or more) reservoir activators (e.g., one or more reservoir activators selected from Table 5), and/or one or more (e.g., 2, 3, 4, 5, 6, 7, 8, 9, 10, or more) HIV-specific bnAb (e.g., 3BNC117, VRC07-523, PGT121, CAP256-VRC26, or PGDM1400). The pharmaceutical composition has the antibody or antigen-binding fragment thereof in an amount of about 0.01-5000 mg (e.g., about 0.01-4000 mg, 0.01-3000 mg, 0.01-2000 mg, 0.01-1000 mg, 0.05-1000 mg, 0.05-500 mg, 0.05-400 mg, 0.05-300 mg, 0.05-200 mg, 0.05-100 mg, 0.1-100 mg, 0.1-90 mg, 0.1-80 mg, 0.1-70 mg, 0.1-60 mg, 0.1-50 mg, 0.1-40 mg, 0.1-30 mg, 0.1-20 mg, 0.1-10 mg, 0.1-9 mg, 0.1-8 mg, 0.1-7 mg, 0.1-6 mg, 0.1-5 mg, 0.1-4 mg, 0.1-3 mg, 0.1-2 mg, or 0.1-1 mg). The pharmaceutical composition with the antibody or antigen-binding fragment thereof may be formulated in a volume of about 1000 ml or less (e.g., about 950 ml or less, about 900 ml or less, about 850 ml or less, about 800 ml or less, about 750 ml or less, about 700 ml or less, about 650 ml or less, about 600 ml or less, about 550 ml or less, about 500 ml or less, about 450 ml or less, about 400 ml or less, about 350 ml or less, about 300 ml or less, about 250 ml or less, about 200 ml or less, about 150 ml or less, about 100 ml or less, about 50 ml or less, about 25 ml or less, about 20 ml or less, about 15 ml or less, about 10 ml or less, about 5 ml or less, about 1 ml or less, or about 0.1 ml or less). The pharmaceutical composition with the PGDM1400 variant antibody or antigen-binding fragment thereof may be formulated in a volume of about 900 ml, 850 ml, 800 ml, 750 ml, 700 ml, 650 ml, 600 ml, 550 ml, 500 ml, 450 ml, 400 ml, 350 ml, 300 ml, 250 ml, 200 ml, 150 ml, 100 ml, 50 ml, 25 ml, 20 ml, 15 ml, 10 ml, 9 ml, 8 ml, 7 ml, 6 ml, 5 ml, 4 ml, 3 ml, 2 ml, 1 ml, 0.5 ml, 0.1 ml, 0.05 ml, or 0.01 ml. The pharmaceutical composition with the PGDM1400 variant antibody or antigen-binding fragment thereof may be formulated in a volume of about 0.1-10 ml (e.g., about 0.1-9 ml, 0.1-8 ml, 0.1-7 ml, 0.1-6 ml, 0.1-5 ml, 0.1-4 ml, 0.1-3 ml, 0.1-2 ml, or 0.1-1 ml)

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015. The pharmaceutical composition may be formulated to release the PGDM1400 variant antibody or fragment thereof described hereinabove immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The pharmaceutical compositions may be sterilized by conventional sterilization techniques, or may be sterile filtered. The resulting aqueous solutions may be packaged for use as is or lyophilized. The lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting pharmaceutical compositions in solid form may, for example, be packaged in multiple single-dose units, each containing a fixed amount of a PGDM1400 variant antibody or fragment thereof described hereinabove, and, if desired, one or more immunomodulatory agents, reservoir activators, HIV-specific bnAbs (such as CD4bs-specific antibodies (e.g., 3BNC117 or VRC07-523), an N332 glycan-dependent antibody (e.g., PGT121, or a variant thereof), and/or a V2-specific antibody (e.g., CAP256-VRC26 and/or the parental PGDM1400)), and/or ARVs, such as in a sealed package of tablets or capsules, or in a suitable dry powder inhaler (DPI) capable of administering one or more doses.

The pharmaceutical compositions, including a PGDM1400 variant antibody or fragment thereof described hereinabove, can be prepared using standard methods known in the art by mixing the active ingredient (e.g., a PGDM1400 variant antibody or antigen-binding fragment thereof described hereinabove) having the desired degree of purity with, optionally, pharmaceutically acceptable carriers, excipients, or stabilizers (Remington's Pharmaceutical Sciences (20th edition), ed. A. Gennaro, 2000, Lippincott, Williams & Wilkins, Philadelphia, PA). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

A PGDM1400 variant antibody or fragment thereof described hereinabove can be administered in a pharmaceutical composition that includes one or more pharmaceutically acceptable carriers, excipients, or diluents. Examples of suitable carriers, excipients, or diluents include, e.g., saline, sterile water, polyalkylene glycols, oils of vegetable origin, hydrogenated napthalenes, suitable buffer, 1,3-butanediol, Ringer's solution and/or sodium chloride solution. Exemplary formulations for parenteral administration includes solutions prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Other exemplary carriers, excipients, or diluents are described in the Handbook of Pharmaceutical Excipients, 6th Edition, Rowe et al., Eds., Pharmaceutical Press (2009), hereby incorporated by reference in its entirety.

A pharmaceutical composition can be formulated to be compatible with its intended route of administration. Solutions or suspensions used for parenteral, intradermal, or subcutaneous application includes the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the PGDM1400 variant antibody or fragment thereof in the required amount in an appropriate solvent with one or a combination of ingredients enumerated above, as required, followed by filtered sterilization. Dispersions can be prepared by incorporating a PGDM1400 variant antibody or antigen-binding fragment thereof into a sterile vehicle which contains a basic dispersion medium and the required other ingredients from those enumerated above. In the case of sterile powders for the preparation of sterile injectable solutions, the preferred methods of preparation can be vacuum drying and freeze-drying which yields a powder of the PGDM1400 variant antibody or antigen-binding fragment thereof plus any additional desired ingredient from a previously sterile-filtered solution thereof.

Oral compositions include an inert diluent or an edible carrier. The composition can be enclosed in a gelatin capsule or compressed into a tablet. For the purpose of oral therapeutic administration, a PGDM1400 variant antibody or fragment thereof can be incorporated with excipients and used in the form of tablets, troches, or gelatin capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated can be used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the antibody or antigen-binding fragment thereof may be formulated into ointments, salves, gels, or creams as generally known in the art.

A PGDM1400 variant antibody or fragment thereof can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art.

The pharmaceutical compositions can be included in a container, pack, or dispenser together with instructions for administration.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention include a pharmaceutically acceptable surfactant at a concentration of 0.005 to 0.02%.

X. Kits

Also featured herein are kits that include the aforementioned PGDM1400 antibody variant or antigen-binding fragment thereof, the polynucleotide encoding the PGDM1400 antibody variant or antigen-binding fragment thereof, the vector containing the polynucleotide, the host cell with the polynucleotide or the vector (e.g., a prokaryotic cell or a eukaryotic cell (e.g., a mammalian cell, such as a CHO or a HEK293 cell)), or the aforementioned composition (e.g., composition including the aforementioned PGDM1400 antibody variant or antigen-binding fragment thereof, the polynucleotide encoding the antibody or antigen-binding fragment thereof, the vector containing the polynucleotide, or the host cell with the polynucleotide or the vector (e.g., a prokaryotic cell or a eukaryotic cell (e.g., a mammalian cell, such as a CHO or a HEK293 cell)), and, e.g., a pharmaceutically-acceptable carrier, in a therapeutically effective amount for preventing or treating HIV infection (e.g., HIV-1 infection) in a subject (e.g., a human, such as a human infected with HIV). The kits can include instructions directing a clinician (e.g., a physician or nurse) in methods for administering the PGDM1400 antibody variant or antigen-binding fragment thereof, the polynucleotide, the vector, the host cell or the composition contained therein.

The kits may include multiple packages of single-dose pharmaceutical composition(s) containing an effective amount of a PGDM1400 antibody variant or antigen-binding fragment thereof, polynucleotide encoding the PGDM1400 antibody variant or antigen-binding fragment thereof, vector containing the polynucleotide, cell with the polynucleotide or composition featured herein. Optionally, instruments or devices necessary for administering the pharmaceutical composition(s) may be included in the kits. For instance, a kit of this invention may provide one or more pre-filled syringes containing an effective amount of the composition described herein (e.g., composition including one or more of the PGDM1400 antibody variant(s) or antigen-binding fragment(s) thereof, as described herein). Furthermore, the kits may also include additional components, such as instructions or schedules for administration of the composition to a patient infected with or at risk of being infected with HIV (e.g., HIV-1).

It will be apparent to those skilled in the art that various modifications and variations can be made in the compositions, methods, and kits of the invention without departing from the spirit or scope of the invention. Thus, it is intended that the invention cover the modifications and variations of this invention provided they come within the scope of the appended claims and their equivalents.

EXAMPLES

The present invention is illustrated by the following examples, which are in no way intended to be limiting of the invention.

Example 1. Generation of bNAbs

Materials and Methods

Antibody material was generated from transient expression of two suspension cell lines, Human Embryonic Kidney 293 (HEK293) and Chinese Hamster Ovary (CHO). The pTT5 mammalian expression vectors containing either a light chain (LC) or heavy chain (HC) coding region were co-transfected into HEK293 cells at a viable cell density (VCD) of $1\times10^6$ cells/mL using polyethyleneimine (PEI) (Durocher et al., *Nucleic Acids Res* 30(2):E9, 2002), and then two-fold diluted with pre-warmed medium to ⅕ shake flask volume. Expression duration was 5-7 days at 37° C., 5% $CO_2$, and 85% humidity at a shaking speed of 130 RPM with an orbit of 19 mm. All clarified supernatants were produced by pelleting the cells at 3000 g for 20 minutes followed by 0.22 μm filtration.

Antibodies were purified from the clarified supernatants using MABSELECT SURE™ protein A resin. A sodium phosphate, sodium chloride buffer system with an arginine wash and an acetate pH 3.5 elution was utilized. Protein A elutions were neutralized with tris, and buffer exchanged into 20 mM sodium phosphate, 150 mM NaCl, pH 7.4.

Size Exclusion High Performance Liquid Chromatography (SE-HPLC)

Size exclusion high performance liquid chromatography (SE-HPLC) was used to separate proteins based on differences in their hydrodynamic volumes. By this method, molecules with larger hydrodynamic protein volumes elute earlier than molecules with smaller volumes. Undiluted samples were loaded onto a Waters XBRIDGE® Protein BEH SEC 200A column (3.5 μm, 7.8×300 mm), separated isocratically with a running buffer (100 mM sodium phosphate and 250 mM sodium chloride, pH 6.8), and the eluent monitored by UV absorbance at 280 nm. Purity was determined by calculating the percentage of each separated component as compared to the total integrated area.

Differential Scanning Fluorimetry (DSF)

Differential scanning fluorimetry (DSF) is a high throughput technique that is used to estimate a protein's relative thermodynamic stability. Ranking of DSF results can be used as a tool to select candidates with more favorable stability properties. The DSF technique consists of measuring the fluorescence intensity of a hydrophobic probe at gradually increasing temperatures to determine the transition temperature and exposure of the hydrophobic regions of a protein. The measurements from this technique, reported as transition temperatures, correlate well with data obtained from differential scanning calorimetry (DSC). Thermal transition temperature(s) by DSF were measured according to the method of Feng et al. (*J Pharm Sci* 99: 1707-1720, 2010). Analysis was done in PBS buffer (20 mM sodium phosphate and 150 mM sodium chloride, pH 7.1) at a final protein concentration of 0.15 mg/ml and a final SYPRO® Orange concentration of 3×. Protein and SYPRO® Orange were mixed at 1:1 volumetric ratio in a 96-well PCR plate and analyzed using a Roche LIGHTCYCLER® 480 instrument equipped with Thermal Shift Analysis Software. Thermal curves were generated by heating the samples from 20-95° C. at a ramp rate of 4.4° C./s and 10 acquisitions per ° C. at Ex=465 nm Em=580 nm. Transition temperatures and shoulder scores were determined using the first derivative of the melting curve.

Thermal Hold Analysis

The stability of proteins at various temperatures was determined as follows. Samples are place in a 96-well Bio-Rad PCR plate and heated to various temperatures for 5 minutes using a Bio-Rad Thermal Cycler. After heating, samples were transferred to a 384-well Grenier clear plate. Protein precipitation was determined by reading the absorbance at 350 nm (A350) using a SPECTRAMAX® M5 plate reader.

Low-pH Stability

The stability of proteins at low pH was determined as follows. The pH of protein samples (1 mg/ml in 20 mM PBS) was lowered to approximately pH 3.3 using 2 M acetic acid. After a 30 minute incubation, samples were neutralized to approximately pH 5.0 using 2 M tris base. Samples were measured in duplicates for high molecular weight species using the SE-HPLC method. As a control, protein samples had the same volume of PBS added as the 2 M acetic acid and 2 M tris base, and measured for high molecular weight species.

Relative Solubility

Solubility was assessed according to the method of Torprani et al. (*J Pharm Sci* 105: 2319-2327, 2016). Analysis was done in PBS buffer (20 mM sodium phosphate and 150 mM sodium chloride, pH 7.1) and a final PEG 10,000 concentration of 7.9%. Protein at 1 mg/ml was diluted into the PEG solution at 1:4 ratio, and incubated in a 96-well 0.22 μm filter plate overnight at room temperature. After PEG incubation, samples were passed through the filter by centrifugation, and the remaining soluble protein was measured by a protein A titer assay.

Chemical Unfolding

Thirty-two guanidine hydrochloride (GuHCl) concentrations in PBS ranging from 0 to 6 M GND were prepared using a liquid handling robot. Protein samples (1 mg/ml in 20 mM PBS) were then transferred to each GuHCl concentration to achieve a final protein concentration of 0.05 mg/ml. After a 24 hour incubation, the samples were measured on a SPECTRAMAX® M5 plate reader (excitation: 280 nm, emission: 300-450 nm). The measured fluorescence intensity at 373 nm was corrected for scattering and stray light by subtraction of a small amount of the summed intensity measured between 300-320 nm (used as a surrogate for signal due to scattering), and then ratioed to the total intensity measured between 320-440 nm to correct for total intensity fluctuations. Then, the chemical unfolding curve was generated by plotting each corrected intensity against the GuHCl concentration. The inflection point of the curve was calculated and reported for each protein sample from this curve. Samples were measured in triplicate.

Neutralization Activity Assay

Neutralization titers of monoclonal antibodies (mAb) were determined using a luciferase-based assay in TZM.bl cells, according to the methods of Montefiori et al. (*Methods Mol Biol* 485: 395-405, 2009) and Sarzotti-Kelsoe et al. (*J Immunol Methods* 409: 131-146, 2014). Briefly, mAb samples at a primary concentration of 25 μg/ml with 5-fold serial dilutions were tested against a panel of 10 HIV-1 pseudoviruses that were selected for being PGDM1400 sensitive. Following incubation of antibody titers with HIV-1 pseudoviruses for 1 hour at 37° C., TZM.bl cells were added in growth media containing DEAE-dextran at a final concentration of 11 μg/ml. Assay plates were incubated for 48 hours at 37° C. and 5% $CO_2$, and luciferase reporter gene expression was measured using BRIGHT-GLO™ luciferase reagent (Promega) and a VICTOR3™ luminometer (PerkinElmer). Neutralization titers (50% and 80% inhibitory concentrations, IC50 and IC80, respectively) were calculated as the mAb concentration at which relative light unit (RLU) was reduced by 50% or 80% compared to RLU in virus control wells after subtraction of background RLU in cell control wells. All assays were performed in a laboratory meeting GCLP standards.

Example 2. Development of Optimized PGDM1400 Variant Antibodies

A series of algorithms were applied to identify potentially destabilizing residues in the Fv region of the broadly neutralizing antibody, PGDM1400. These residues by themselves, or in combination, lead to instability at low pH, increased susceptibility to chemical degradation, or increased aggregation during production or long term storage. Based on this analysis, a series of variants were designed for maintaining potency while optimizing desired characteristics using combinatorial residue replacement techniques. The optimization process was broken up into different stages, the first being identification of single residues in the framework region that are potentially responsible for destabilization. Based on the analysis, a series of variants were produced by transient expression, each containing a single residue modification of the identified amino acids, or in a few variants, combinations of amino acids based on their proximity to each other (Round-1 variants, Table 1; FIG. 1; FIG. 2). The variants were characterized for desired biophysical characteristics (Tables 6-8), and retention of neutralization activity (Tables 9 and 10). From the analysis, five residues of the light chain (KV: F2, KV: H9, KV: S18, KV: D73, KV: T85) were identified that showed an increase in desirable biophysical characteristics, and did not impact neutralization. Together, the distinct single residues were used to produce a library of variants encompassing combinatorial residue replacements (Round-2 variants, Table 2; FIG. 1; FIG. 3). The variants were again produced by transient expression and the purified combinatorial variants analyzed for retention of neutralization activity and for desired biophysical characteristics. Together, the combinatorial libraries of variants allowed for identification of molecules with significantly increased low-pH stability (e.g., to pH 3.3), increased thermal stability (up to 95° C.), increased stability to chemical unfolding (e.g., in presence of 0 to 6 M GuHCl, see Tables 6-8 and 11-13), and retention of neutralization activity against several different HIV pseudoviruses (Tables 9, 10, 14 and 15). The variable domain residue positions were numbered according to the AHo structure-based numbering (Honegger and Plückthun, *J Mol Bio* 309: 657-670, 2001).

Example 3. Characterization of Round-1 PGDM1400 Variant Antibodies

Round-1 variants of PGDM1400 (Table 1) were produced by transient expression in HEK293 cells and purified by protein A chromatography. The antibodies were buffer exchanged into phosphate buffered saline and used for analysis. Assays used for analysis of the Round-1 variants included titer, size exclusion chromatography (SEC) to quantify high molecular weight (HMW) species and oligomers following purification (Table 6), DSF to characterize stability of the CH2 and Fab domains during thermal ramping, chemical unfolding by GuHCl for determining storage stability (Table 7), PEG solubility to interrogate protein-protein interaction (Table 8), and retention of neutralization capacity (Tables 9 and 10).

The monomer content of the variants ranged from a low of 88.2% to a high of 92%, where majority of the variation was due to dimer formation in the protein A purified material. DSF analysis showed that the Tm1 varied from 69.1 to 71.4° C., with a small number of the single variants (e.g., MS-66, MS-67, MS-70 and MS-75) possessing a Tm2. Weighted Shoulder Score (WSS) analysis, which provides a finer distinction between variants, with higher values being more desirable, showed that a subset of the single mutation variant with KV:F2I mutation (e.g., MS-66) had a 20 point increase in WSS over the parental molecule, MS-119. Other biophysical assays correlated to stability, including chemical unfolding that reports inflection point and ΔG of unfolding, and solubility in PEG solutions also showed increased values for variants with single point mutations. Incubation of the parental antibody and variants in the low pH solution followed by neutralization showed little change in the HMW values, indicating that the molecule was stable under low pH conditions.

The variants were also assayed for retention of neutralization activity. Tables 9 and 10 show neutralization activity of Round-1 variants against 12 pseudoviruses of HIV, which are representative of the broader set of viruses against which the parental PGDM1400 antibody is active. The PGDM1400 variant antibodies with more than 3-fold increase in the 1050 or 1080 values for a particular pseudovirus were considered inactive and discarded from further consideration. As evidenced by the data, single mutation variants MS-79 and MS-80 showed loss of activity for specific pseudoviruses. Also, the combinatorial variants MS-85 through MS-88 and the N-terminal variants MS-89 through MS-92 showed loss in activity and were removed from further consideration.

Example 4. Characterization of Round-2 PGDM1400 Variant Antibodies

Round-2 variants were designed based on the single light chain variants MS-66 (KV:F2I), MS-67 (KV:H9L), MS-69 (KV:S18P), MS-71 (KV:D73G), MS-73 (KV:T85A). The combinatorial variants built from these amino acid sets for the Round-2 variants are listed in Table 2. Assays used for analysis of the Round-2 variants included SEC to quantify monomer and HMW species following purification, DSF to characterize stability of the CH2 and Fab domains during thermal ramping, chemical unfolding, low pH stability, solubility, and retention of neutralization capacity.

Results of the initial screening consisting of SEC analysis for dimer and oligomer are shown in Table 11, while results for the DSF, low pH stability, chemical unfolding and solubility are shown in Tables 12 and 13. The dimer and oligomer content of all variants were similar to the parental molecule, MS-119 (Table 1), and were, thus, not a differentiating factor for identifying the optimal molecules. However, the DSF analysis demonstrated an increase of 3° C. for Tm2 of a number of variants, which also showed an increase in WSS by an average of 20 points. Conformational stability was evaluated by chemical unfolding, which assesses the intrinsic resistance of the native state against unfolding as measured by the mid-point of the denaturation curve. Variants with the highest Tm2 and WSS showed the greatest increase in inflection point (i.e., up to 0.25 M from the parental molecule) by chemical unfolding (Table 12). Interestingly, the presence of KV:F2I mutation was the common denominator across these variants. Variants containing the KV:F2I mutation showed an average WSS of 30.3 with the highest being 34 and the range being 26-34, compared to an average of 12.8 with a range of 11-15 for those combinatorial variants not containing the mutation. Additionally, the inflection point by chemical unfolding was higher in variants with the KV:F2I mutation (average value 2.44 M) compared to the parental molecule (average value 2.26 M), whereas, variants without the mutation showed an average value of 2.30 M. The fact that it takes slightly more GuHCl for the variant antibodies to reach the same point of chemical unfolding as the parental PGDM1400 antibody may be due to tighter packing of the hydrophobic core of the Fv. Together, these results are indicative of an increase in conformational stability of the combinatorial variants in comparison to the parental molecule.

Colloidal stability was also investigated and shown to increase for a number of the combinatorial variants (Table 13). Specifically, we investigated high temperature aggregation, solubility in PEG solutions and self-interaction nanoparticle spectroscopy (SINS). High temperature aggregation was investigated at 68° C. and 69.2° C., temperatures at which parental PGDM1400, MS-119, readily aggregates. Similar to the conformational stability results, a number of Round-2 combinatorial variants showed no aggregation at temperatures that cause aggregation of the parental PGDM1400 molecule. Again, the KV:F2I mutation was found to be central to these observations. Only those variants that carried the KV:F2I mutation were resistant to aggregation at high temperature, while variants without the mutation showed aggregation profiles similar to the parental molecule, MS-119. PEG solubility, which is indicative of protein/protein interaction was measured at 9.4% w/v PEG, a concentration at which only 50% of the parental molecule, MS-119 is soluble. The results for the solubility assay demonstrated a decrease in solubility for some variants, with a number of them being similar to the parental molecule, MS-119. This result was consistent with the method used to define destabilizing sites where solubility was not specifically targeted. Similarly, result from SINS analysis, which reports protein/protein interactions related to viscosity, was comparable between the variants and the parental molecule, MS-119, and are not shown.

Finally, the variants were assayed for retention of neutralization activity. Tables 14 and 15 show neutralization activity of Round-2 variants against 12 pseudoviruses of HIV that are representative of the broader set of viruses against which PGDM1400 is active. Antibodies with more than a 3-fold increase in the IC50 or IC80 value for a particular pseudovirus were considered inactive and discarded from further consideration. As evidenced from the data, the combinatorial variants showed similar IC50 and IC80 values within the approximate 3-fold limit of the assay.

Overall, analysis of the Round-2 variants (outlined in Tables 11-15) showed significant increase in multiple stability characteristics including thermal stability, chemical stability, and conformational stability, which are important for increased manufacturability and storage stability of the molecules.

TABLE 6

Analysis of biophysical characteristics of Round-1 PGDM1400 variant antibodies: titer and SEC

| Molecule Set | Titer (μg/ml) | SEC (% Main) | SEC (% Dimer) | SEC (% Oligomer) |
|---|---|---|---|---|
| MS-119 | 56.5 | 88.62 | 8.77 | 2.61 |
| MS-66 | 217 | 91.18 | 7.22 | 1.59 |
| MS-67 | 124.2 | 91.52 | 7.18 | 1.3 |
| MS-68 | 75.6 | 89.37 | 8.41 | 2.22 |
| MS-69 | 169.8 | 91.25 | 7.34 | 1.41 |
| MS-70 | 136.3 | 90.32 | 8.09 | 1.59 |
| MS-71 | 182.2 | 91.8 | 7.03 | 1.17 |
| MS-72 | 143.9 | 90.68 | 7.86 | 1.47 |
| MS-73 | 213.1 | 90.89 | 7.71 | 1.4 |
| MS-74 | 119.5 | 91.15 | 7.47 | 1.38 |
| MS-75 | 113 | 90.07 | 8.17 | 1.76 |
| MS-76 | 35 | 91.54 | 7.19 | 1.27 |
| MS-77 | 106.7 | 91.09 | 7.36 | 1.55 |
| MS-78 | 49 | 88.17 | 9.06 | 2.77 |
| MS-79 | 39.7 | 89.56 | 8.54 | 1.9 |
| MS-80 | 33.5 | 90.32 | 7.69 | 2 |
| MS-81 | 39.3 | 88.7 | 8.75 | 2.55 |
| MS-82 | 32.5 | 88.64 | 9 | 2.35 |
| MS-83 | 92.8 | 87.42 | 10.17 | 2.42 |
| MS-84 | 45.3 | 89.21 | 8.24 | 2.54 |
| MS-85 | 187.3 | 90.51 | 7.8 | 1.69 |
| MS-86 | 49.1 | 92.01 | 7 | 0.98 |
| MS-87 | 44.6 | 90.73 | 7.72 | 1.55 |
| MS-88 | 41.9 | 91.85 | 7.16 | 0.98 |
| MS-89 | 77.6 | 92.12 | 6.81 | 1.07 |
| MS-90 | 101.2 | 93.72 | 5.71 | 0.57 |
| MS-91 | 89.5 | 93.57 | 5.64 | 0.79 |
| MS-92 | 186.2 | 90.63 | 7.7 | 1.68 |

TABLE 7

Analysis of additional biophysical characteristics of Round-1 PGDM1400 variant antibodies: DSF and isothermal chemical unfolding

| Molecule Set | DSF T1 ° C (Avg. n = 2) | Std Dev | DSF T2 ° C. (Avg. n = 2) | Std Dev | Weighted Shoulder Score | Std Dev | Inflection Pt (Avg n = 3) | Std Dev | ΔG (Avg n = 2) | Std Dev |
|---|---|---|---|---|---|---|---|---|---|---|
| MS-119 | 71.2 | 0.02 | | | 13.5 | 0.09 | 2.23 | 0.04 | 10.7 | 1.0 |
| MS-66 | 70.4 | 0.21 | 77.5 | 0.07 | 36.12 | 4.13 | 2.38 | 0.02 | 14.5 | 3.2 |
| MS-67 | 71.4 | 0.46 | 74.3 | 0.00 | 20.74 | 0.20 | 2.28 | 0.03 | 14.3 | 2.9 |
| MS-68 | 70.4 | 0.13 | | | 11.91 | 0.02 | 2.02 | 0.03 | 8.2 | 0.6 |
| MS-69 | 71.1 | 0.40 | | | 11.58 | 0.65 | 2.24 | 0.03 | 12.3 | 0.9 |
| MS-70 | 71.4 | 0.22 | 73.2 | 0.00 | 15.17 | 0.60 | 2.28 | 0.03 | 12.7 | 1.3 |
| MS-71 | 71.1 | 0.21 | | | 7.05 | 0.53 | 2.28 | 0.01 | 17.5 | 1.9 |
| MS-72 | 71.0 | 0.13 | | | 12.66 | 0.00 | 2.19 | 0.07 | 10.7 | 2.4 |
| MS-73 | 71.4 | 0.32 | | | 12.36 | 1.16 | 2.25 | 0.03 | 12.5 | 3.7 |
| MS-74 | 71.5 | 0.36 | | | 12.26 | 0.21 | 2.23 | 0.02 | 11.2 | 2.3 |
| MS-75 | 71.1 | 0.06 | 75.1 | 0.14 | 9.08 | 0.30 | 2.32 | 0.02 | 14.7 | 1.0 |

TABLE 7-continued

Analysis of additional biophysical characteristics of Round-1 PGDM1400 variant antibodies: DSF and isothermal chemical unfolding

| Molecule Set | DSF T1 ° C (Avg. n = 2) | Std Dev | DSF T2 ° C. (Avg. n = 2) | Std Dev | Weighted Shoulder Score | Std Dev | Inflection Pt (Avg n = 3) | Std Dev | ΔG (Avg n = 2) | Std Dev |
|---|---|---|---|---|---|---|---|---|---|---|
| MS-76 | 71.1 | 0.22 | | | 17.43 | 3.51 | 2.21 | 0.02 | 12.4 | 3.0 |
| MS-77 | 71.1 | 0.08 | | | 13.39 | 1.27 | 2.18 | 0.04 | 10.9 | 2.5 |
| MS-78 | 71.1 | 0.19 | | | 15.07 | 0.14 | 2.34 | 0.02 | 14.3 | 2.6 |
| MS-79 | 70.5 | 0.19 | | | 6.69 | 0.13 | | | | |
| MS-80 | 69.7 | 0.03 | | | 7.59 | 0.40 | 2.02 | 0.02 | 7.3 | 1.5 |
| MS-81 | 71.0 | 0.02 | | | 9.85 | 0.10 | 2.27 | 0.05 | 14.0 | 5.1 |
| MS-82 | 70.5 | 0.02 | | | 10.96 | 0.57 | | | | |
| MS-83 | 71.0 | 0.14 | | | 3.80 | 0.09 | 2.25 | 0.01 | 11.8 | 1.6 |
| MS-84 | 69.8 | 0.12 | | | 13.74 | 0.39 | | | | |
| MS-85 | 70.4 | 0.09 | 77.3 | 0.00 | 7.87 | 0.06 | | | | |
| MS-86 | 71.0 | 0.17 | 75.2 | 0.00 | 13.34 | 0.54 | 2.32 | 0.04 | 13.7 | 3.6 |
| MS-87 | 69.1 | 0.06 | | | 5.53 | 2.23 | | | | |
| MS-88 | 69.6 | 0.06 | | | 32.36 | 1.24 | 2.12 | 0.03 | 9.4 | 1.5 |
| MS-89 | 70.9 | 0.01 | | | 19.80 | 0.15 | | | | |
| MS-90 | 71.0 | 0.17 | 75.4 | 0.00 | 23.47 | 0.63 | 2.32 | 0.01 | 14.1 | 2.1 |
| MS-91 | 70.9 | 0.09 | 74.8 | 0.00 | 17.81 | 1.52 | | | | |
| MS-92 | 70.5 | 0.04 | 78.4 | 0.14 | 29.87 | 0.57 | | | | |

TABLE 8

Analysis of additional biophysical characteristics of Round-1 PGDM1400 variant antibodies: low pH stability and PEG solubility

| Molecule Set | pH 3.3 HMW % (Avg n = 2) | Std Dev | PEG Solubility (Avg n = 4) | Std Dev |
|---|---|---|---|---|
| MS-119 | 10.22 | 0.43 | 0.13 | 0.03 |
| MS-66 | 5.62 | 0.26 | 0.11 | 0.03 |
| MS-67 | 6.01 | 0.25 | 0.15 | 0.01 |
| MS-68 | 6.74 | 0.08 | 0.14 | 0.02 |
| MS-69 | 5.86 | 0.37 | 0.13 | 0.02 |
| MS-70 | 5.46 | 0.22 | 0.15 | 0.01 |
| MS-71 | 4.61 | 0.23 | 0.13 | 0.01 |
| MS-72 | 6.35 | 0.54 | 0.12 | 0.01 |
| MS-73 | 6.02 | 0.28 | 0.15 | 0.01 |
| MS-74 | 5.84 | 0.21 | 0.14 | 0.01 |
| MS-75 | 6.39 | 0.25 | 0.15 | 0.01 |
| MS-76 | 6.27 | 0.14 | 0.11 | 0.01 |
| MS-77 | 7.69 | 0.57 | 0.12 | 0.02 |
| MS-78 | 7.94 | 0.47 | 0.13 | 0.01 |
| MS-79 | 5.84 | 0.15 | 0.11 | 0.01 |

TABLE 8-continued

Analysis of additional biophysical characteristics of Round-1 PGDM1400 variant antibodies: low pH stability and PEG solubility

| Molecule Set | pH 3.3 HMW % (Avg n = 2) | Std Dev | PEG Solubility (Avg n = 4) | Std Dev |
|---|---|---|---|---|
| MS-80 | 3.56 | 0.13 | 0.10 | 0.01 |
| MS-81 | 6.38 | 0.34 | 0.14 | 0.01 |
| MS-82 | 6.36 | 0.26 | 0.10 | 0.01 |
| MS-83 | 8.31 | 0.44 | 0.12 | 0.02 |
| MS-84 | 8.18 | 0.47 | 0.11 | 0.01 |
| MS-85 | 4.62 | 0.28 | 0.14 | 0.01 |
| MS-86 | 4.63 | 0.82 | 0.10 | 0.01 |
| MS-87 | 18.85 | 0.81 | 0.08 | 0.01 |
| MS-88 | 5.06 | 0.06 | 0.06 | 0.01 |
| MS-89 | 4.35 | 0.27 | 0.09 | 0.01 |
| MS-90 | 4.80 | 0.17 | 0.09 | 0.02 |
| MS-91 | 4.60 | 1.71 | 0.14 | 0.03 |
| MS-92 | 5.62 | 0.26 | 0.12 | 0.01 |

TABLE 9

Analysis of neutralization activity of Round-1 PGDM1400 variant antibodies against representative PGDM1400 sensitive virus panel (SC422661.8, RHPA4259.7, Du172.17, BB1012-11.TC21, CNE52, 0260.v5.c36) in TZM.bl cells. Loss of potency are values > 3-fold of control value.

| Molecule | SC422661.8 | | RHPA4259.7 | | Du172.17 | | BB1012-11.TC21 | | CNE52 | | 0260.v5.c36 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.872 | 4.865 | 0.340 | 1.197 | 2.380 | 9.384 | 0.031 | 0.102 | 0.452 | 2.727 | 0.035 | 0.138 |
| MS-194 | 0.365 | 3.293 | 0.181 | 0.704 | 1.918 | 6.811 | 0.025 | 0.103 | 0.098 | 0.839 | 0.015 | 0.064 |
| MS-66 | 0.902 | 5.820 | 0.238 | 0.745 | 2.076 | 11.315 | 0.017 | 0.074 | 0.408 | 3.743 | 0.024 | 0.092 |
| MS-67 | 0.549 | 2.825 | 0.129 | 0.706 | 1.757 | 9.307 | 0.017 | 0.071 | 0.212 | 1.813 | 0.023 | 0.088 |
| MS-68 | 0.538 | 2.021 | 0.199 | 0.759 | 1.821 | 6.797 | 0.023 | 0.076 | 0.136 | 1.133 | 0.019 | 0.073 |
| MS-69 | 0.609 | 3.372 | 0.139 | 0.811 | 1.404 | 5.604 | 0.018 | 0.071 | 0.129 | 1.902 | 0.021 | 0.078 |
| MS-70 | 0.391 | 2.430 | 0.182 | 0.734 | 1.493 | 6.053 | 0.021 | 0.079 | 0.301 | 2.547 | 0.028 | 0.103 |
| MS-71 | 0.273 | 1.935 | 0.164 | 0.583 | 1.289 | 6.069 | 0.015 | 0.054 | 0.172 | 2.587 | 0.022 | 0.062 |
| MS-72 | 0.373 | 2.826 | 0.247 | 1.157 | 1.748 | 8.758 | 0.023 | 0.089 | 0.302 | 4.534 | 0.023 | 0.114 |
| MS-73 | 0.384 | 2.543 | 0.094 | 0.549 | 0.934 | 4.999 | 0.023 | 0.086 | 0.207 | 1.809 | 0.018 | 0.065 |
| MS-74 | 0.388 | 3.506 | 0.132 | 0.461 | 1.460 | 5.570 | 0.021 | 0.093 | 0.169 | 1.457 | 0.017 | 0.086 |
| MS-75 | 0.489 | 9.411 | 0.276 | 1.313 | 3.559 | 16.146 | 0.029 | 0.134 | 0.687 | 7.547 | 0.034 | 0.137 |
| MS-76 | 0.360 | 6.457 | 0.242 | 0.842 | 1.702 | 9.675 | 0.013 | 0.059 | 0.174 | 1.372 | 0.010 | 0.060 |
| MS-77 | 0.373 | 3.588 | 0.209 | 0.734 | 2.233 | 12.211 | 0.023 | 0.103 | 0.322 | 2.715 | 0.019 | 0.101 |
| MS-78 | 0.635 | 3.631 | 0.241 | 0.841 | 1.714 | 6.997 | 0.024 | 0.105 | 0.233 | 1.394 | 0.020 | 0.095 |
| MS-79 | 0.587 | >25 | 0.221 | 0.792 | 7.279 | >25 | 0.019 | 0.080 | 2.420 | >25 | 0.028 | 0.159 |
| MS-80 | 0.451 | >25 | 0.267 | 1.240 | 15.238 | >25 | 0.020 | 0.086 | 5.245 | >25 | 0.041 | 0.321 |

TABLE 9-continued

Analysis of neutralization activity of Round-1 PGDM1400 variant antibodies against representative PGDM1400 sensitive virus panel (SC422661.8, RHPA4259.7, Du172.17, BB1012-11.TC21, CNE52, 0260.v5.c36) in TZM.bl cells. Loss of potency are values > 3-fold of control value.

| Molecule | SC422661.8 | | RHPA4259.7 | | Du172.17 | | BB1012-11.TC21 | | CNE52 | | 0260.v5.c36 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| MS-81 | 0.418 | 4.246 | 0.202 | 0.897 | 1.647 | 6.371 | 0.024 | 0.102 | 0.212 | 1.802 | 0.020 | 0.075 |
| MS-82 | 0.387 | 3.295 | 0.192 | 0.672 | 1.881 | 6.995 | 0.023 | 0.108 | 0.206 | 1.183 | 0.016 | 0.051 |
| MS-83 | 0.267 | 2.112 | 0.150 | 0.663 | 1.465 | 7.404 | 0.018 | 0.082 | 0.135 | 1.039 | 0.023 | 0.087 |
| MS-84 | 0.192 | 1.374 | 0.175 | 0.773 | 1.635 | 6.554 | 0.019 | 0.085 | 0.092 | 0.830 | 0.016 | 0.062 |
| MS-85 | 0.540 | 7.038 | 0.173 | 0.794 | 2.233 | 9.528 | 0.028 | 0.124 | 0.341 | 4.708 | 0.019 | 0.059 |
| MS-86 | 1.196 | >25 | 0.305 | 1.103 | 4.941 | 18.786 | 0.048 | 0.159 | 1.462 | 13.262 | 0.036 | 0.191 |
| MS-87 | 0.711 | 13.927 | 0.294 | 1.093 | >25 | >25 | 0.023 | 0.102 | 2.686 | >25 | 0.114 | 1.010 |
| MS-88 | 1.410 | >25 | 0.504 | 2.509 | >25 | >25 | 0.020 | 0.088 | 5.857 | >25 | 0.178 | 1.514 |
| MS-89 | 0.786 | >25 | 0.290 | 1.040 | 11.866 | >25 | 0.032 | 0.143 | 2.343 | 23.795 | 0.036 | 0.197 |
| MS-90 | 1.480 | >25 | 0.254 | 1.330 | 4.068 | 15.574 | 0.044 | 0.204 | 1.046 | 8.560 | 0.030 | 0.168 |
| MS-91 | 1.655 | 22.127 | 0.267 | 1.824 | 3.851 | 23.865 | 0.037 | 0.170 | 1.405 | 10.577 | 0.046 | 0.171 |
| MS-92 | 1.529 | >25 | 0.250 | 1.155 | 6.850 | >25 | 0.029 | 0.127 | 3.919 | >25 | 0.044 | 0.350 |

Assay Set up: mAbs tested at primary concentration of 25 ug/ml and titrated 5-fold 7x (duplicate wells)

TABLE 10

Analysis of neutralization activity of Round-1 PGDM1400 variant antibodies against additional representative PGDM1400 sensitive virus panel (263-8, SC05.8C11.2344, X1193_c1, Ce1176_A3, AC10.0.29, 6952.v1.c20) in TZM.bl cells. Loss of potency are values > 3-fold of control value.

| Molecule | 263-8 | | SC05.8C11.2344 | | X1193_c1 | | Ce1176_A3 | | AC10.0.29 | | 6952.v1.c20 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.018 | 0.085 | 0.575 | 2.533 | 0.148 | 0.525 | 0.252 | 2.788 | 0.051 | 0.230 | 0.600 | 10.550 |
| MS-194 | 0.007 | 0.026 | 0.458 | 1.532 | 0.088 | 0.311 | 0.023 | 0.292 | 0.044 | 0.290 | 0.144 | 6.577 |
| MS-66 | 0.017 | 0.060 | 0.811 | 2.536 | 0.086 | 0.322 | 0.165 | 5.427 | 0.035 | 0.213 | 0.284 | >25 |
| MS-67 | 0.011 | 0.037 | 0.631 | 2.144 | 0.075 | 0.303 | 0.105 | 1.898 | 0.031 | 0.186 | 0.280 | 7.888 |
| MS-68 | 0.011 | 0.038 | 0.708 | 1.946 | 0.100 | 0.287 | 0.096 | 1.644 | 0.040 | 0.169 | 0.206 | 12.877 |
| MS-69 | 0.010 | 0.046 | 0.456 | 1.690 | 0.072 | 0.326 | 0.087 | 1.709 | 0.029 | 0.169 | 0.182 | 3.064 |
| MS-70 | 0.016 | 0.047 | 0.508 | 1.360 | 0.111 | 0.413 | 0.060 | 0.968 | 0.053 | 0.206 | 0.285 | 4.839 |
| MS-71 | 0.014 | 0.041 | 0.425 | 1.410 | 0.072 | 0.265 | 0.040 | 0.796 | 0.035 | 0.177 | 0.325 | 7.924 |
| MS-72 | 0.020 | 0.057 | 0.791 | 2.854 | 0.072 | 0.258 | 0.074 | 1.298 | 0.051 | 0.255 | 0.643 | 12.437 |
| MS-73 | 0.010 | 0.032 | 0.461 | 1.624 | 0.085 | 0.327 | 0.035 | 0.581 | 0.041 | 0.206 | 0.222 | 6.993 |
| MS-74 | 0.013 | 0.037 | 0.415 | 1.935 | 0.086 | 0.296 | 0.028 | 0.564 | 0.041 | 0.216 | 0.285 | 15.123 |
| MS-75 | 0.018 | 0.086 | 0.792 | 3.718 | 0.174 | 0.591 | 0.139 | 2.785 | 0.055 | 0.442 | 0.977 | >25 |
| MS-76 | 0.015 | 0.053 | 0.587 | 2.567 | 0.126 | 0.575 | 0.082 | 1.631 | 0.047 | 0.368 | 0.844 | >25 |
| MS-77 | 0.012 | 0.033 | 0.516 | 2.412 | 0.109 | 0.398 | 0.067 | 1.120 | 0.036 | 0.311 | 0.236 | 6.741 |
| MS-78 | 0.014 | 0.053 | 0.658 | 2.257 | 0.126 | 0.452 | 0.047 | 0.837 | 0.044 | 0.225 | 0.342 | >25 |
| MS-79 | 0.018 | 0.067 | 0.593 | 1.970 | 0.109 | 0.365 | 0.473 | 9.051 | 0.056 | 0.404 | 13.249 | >25 |
| MS-80 | 0.033 | 0.173 | 0.898 | 3.147 | 0.137 | 0.607 | 1.115 | >25 | 0.054 | 0.280 | >25 | >25 |
| MS-81 | 0.013 | 0.037 | 0.537 | 2.006 | 0.113 | 0.512 | 0.044 | 0.646 | 0.044 | 0.324 | 0.228 | >25 |
| MS-82 | 0.011 | 0.033 | 0.502 | 1.797 | 0.084 | 0.411 | 0.023 | 0.635 | 0.050 | 0.267 | 0.212 | 22.966 |
| MS-83 | 0.007 | 0.050 | 0.381 | 1.879 | 0.061 | 0.308 | 0.029 | 0.405 | 0.038 | 0.259 | 0.126 | 3.089 |
| MS-84 | 0.006 | 0.030 | 0.481 | 1.737 | 0.058 | 0.285 | 0.018 | 0.567 | 0.052 | 0.257 | 0.237 | 18.201 |
| MS-85 | 0.011 | 0.043 | 0.425 | 1.488 | 0.068 | 0.507 | 0.073 | 1.719 | 0.044 | 0.242 | 0.393 | >25 |
| MS-86 | 0.009 | 0.050 | 1.622 | 5.393 | 0.167 | 0.371 | 0.366 | 4.246 | 0.107 | 0.741 | 2.548 | >25 |
| MS-87 | 0.065 | 0.361 | 1.231 | 5.167 | 0.098 | 0.277 | 0.907 | 24.985 | 0.059 | 0.328 | >25 | >25 |
| MS-88 | 0.111 | 0.990 | 1.544 | 7.312 | 0.171 | 0.775 | 2.756 | >25 | 0.089 | 0.743 | >25 | >25 |
| MS-89 | >25 | >25 | 0.820 | 3.746 | 0.144 | 0.636 | 0.298 | 9.212 | 0.067 | 0.618 | >25 | >25 |
| MS-90 | 0.021 | 0.109 | 1.496 | 3.841 | 0.114 | 0.399 | 0.220 | 4.240 | 0.059 | 0.592 | 2.678 | >25 |
| MS-91 | 0.020 | 0.075 | 0.848 | 2.838 | 0.057 | 0.388 | 0.213 | 2.042 | 0.070 | 0.632 | 2.615 | >25 |
| MS-92 | 0.024 | 0.208 | 1.537 | 4.092 | 0.110 | 0.529 | 0.600 | 9.783 | 0.051 | 0.446 | 7.376 | >25 |

TABLE 11

Analysis of biophysical characteristics of Round-2 PGDM1400 variant antibodies: titer and SEC

| Molecule Set | Titer (μg/ml) | SEC (% Main) | SEC (% Dimer) | SEC (% Oligomer) |
|---|---|---|---|---|
| MS-119 | 362.3 | 96.53 | 2.68 | 0.61 |
| MS-93 | 529.4 | 96.46 | 2.81 | 0.55 |
| MS-94 | 750.3 | 96.88 | 2.43 | 0.5 |

TABLE 11-continued

Analysis of biophysical characteristics of Round-2 PGDM1400 variant antibodies: titer and SEC

| Molecule Set | Titer (μg/ml) | SEC (% Main) | SEC (% Dimer) | SEC (% Oligomer) |
|---|---|---|---|---|
| MS-95 | 831.4 | 85.9 | 12.98 | 0.86 |
| MS-96 | 875.4 | 96.57 | 2.69 | 0.55 |
| MS-97 | 160.9 | 95.71 | 3.29 | 0.69 |

TABLE 11-continued

Analysis of biophysical characteristics of Round-2 PGDM1400 variant antibodies: titer and SEC

| Molecule Set | Titer (μg/ml) | SEC (% Main) | SEC (% Dimer) | SEC (% Oligomer) |
|---|---|---|---|---|
| MS-98 | 484.6 | 97.99 | 1.59 | 0.22 |
| MS-99 | 322.2 | 96.7 | 2.64 | 0.44 |
| MS-100 | 345.8 | 97.92 | 1.63 | 0.25 |
| MS-101 | 411.2 | 97.01 | 2.36 | 0.43 |
| MS-102 | 456.3 | 97.56 | 1.95 | 0.28 |
| MS-103 | 430.7 | 97.12 | 2.23 | 0.46 |
| MS-104 | 672.9 | 96.81 | 2.63 | 0.39 |
| MS-105 | 631.5 | 95.68 | 3.28 | 0.84 |
| MS-106 | 253.1 | 95.01 | 4.04 | 0.67 |
| MS-107 | 312.7 | 94.22 | 4.63 | 0.93 |
| MS-108 | 311.3 | 95.07 | 4.01 | 0.7 |
| MS-109 | 278 | 96.66 | 2.68 | 0.45 |
| MS-110 | 195.7 | 95.26 | 3.72 | 0.75 |
| MS-111 | 444.2 | 97.1 | 2.33 | 0.4 |
| MS-112 | 460.2 | 95.93 | 3.3 | 0.6 |
| MS-113 | 343.6 | 94.62 | 4.41 | 0.75 |
| MS-114 | 650 | 95.31 | 3.78 | 0.74 |
| MS-115 | 541.9 | 95.28 | 3.87 | 0.67 |
| MS-116 | 289.6 | 93.81 | 5.00 | 0.94 |
| MS-117 | 509.9 | 96.02 | 3.24 | 0.58 |
| MS-118 | 701.1 | 96.19 | 3.06 | 0.57 |

TABLE 13

Analysis of additional biophysical characteristics of Round-2 PGDM1400 variant antibodies: thermal hold, solubility, and SINS

| Molecule Set | Thermal Hold: A350 Heated 68° C. in | Thermal Hold: A350 Heated 69.2° C. in | 9.4% PEG Solubility (Avg. n = 4) | Std Dev |
|---|---|---|---|---|
| MS-119 | 0.5211 | 0.5941 | 0.14 | 0.01 |
| MS-93 | 0.0798 | 0.0953 | 0.13 | 0.02 |
| MS-94 | 0.0798 | 0.2821 | 0.13 | 0.01 |
| MS-95 | 0.0807 | 0.1843 | 0.12 | 0.01 |
| MS-96 | 0.0756 | 0.1181 | 0.14 | 0.01 |
| MS-97 | 0.6173 | 0.4481 | 0.13 | 0.01 |
| MS-98 | 0.5878 | 0.5949 | 0.13 | 0.01 |
| MS-99 | 0.5764 | 0.6219 | 0.14 | 0.01 |
| MS-100 | 0.6164 | 0.64 | 0.11 | 0.01 |
| MS-101 | 0.6221 | 0.5229 | 0.13 | 0.01 |
| MS-102 | 0.5824 | 0.6174 | 0.12 | 0.01 |
| MS-103 | 0.0694 | 0.1403 | 0.14 | 0.02 |
| MS-104 | 0.0703 | 0.1336 | 0.13 | 0.01 |
| MS-105 | 0.0904 | 0.5936 | 0.15 | 0.01 |
| MS-106 | 0.0946 | 0.392 | 0.12 | 0.01 |
| MS-107 | 0.0996 | 0.2462 | 0.13 | 0.02 |
| MS-108 | 0.0916 | 0.2408 | 0.12 | 0.01 |
| MS-109 | 0.6081 | 0.5371 | 0.12 | 0.01 |
| MS-110 | 0.623 | 0.504 | 0.13 | 0.01 |
| MS-111 | 0.5932 | 0.5551 | 0.13 | 0.01 |
| MS-112 | 0.6375 | 0.5974 | 0.13 | 0.01 |

TABLE 12

Analysis of additional biophysical characteristics of Round-2 PGDM1400 variant antibodies: DSF, isothermal chemical unfolding and low pH stability

| Molecule Set | DSF T1° C. (Avg. n = 2) | Std Dev | DSF T2° C. (Avg. n = 2) | Std Dev | Weighted shoulder Score | Std Dev | Inflection Pt of Unfolding (Avg n = 3) | Std Dev | pH 3.3 HMW % (Avg n = 2) | Std Dev |
|---|---|---|---|---|---|---|---|---|---|---|
| MS-119 | 70.6 | 0.1 | 74.2 | 0.1 | 13 | 0 | 2.26 | 0.02 | 3.74 | 0.13 |
| MS-93 | 70.5 | 0.0 | 77.9 | 0.1 | 34 | 1 | 2.45 | 0.03 | 3.67 | 0.29 |
| MS-94 | 70.3 | 0.0 | 77.4 | 0.1 | 29 | 1 | 2.39 | 0.02 | 3.97 | 0.83 |
| MS-95 | 70.5 | 0.1 | 77.5 | 0.0 | 26 | 1 | 2.47 | 0.01 | 14.14 | 0.13 |
| MS-96 | 70.5 | 0.1 | 77.7* | | 31 | 1 | 2.45 | 0.00 | 4.06 | 0.47 |
| MS-97 | 70.7 | 0.3 | 74.0 | 0.1 | 14 | 1 | 2.28 | 0.04 | 4.90 | 0.42 |
| MS-98 | 70.5 | 0.4 | 73.9 | 0.1 | 13 | 0 | 2.36 | 0.02 | 2.86 | 0.01 |
| MS-99 | 70.3 | 0.0 | 74.5* | | 15 | 1 | 2.37 | 0.03 | 4.43 | 0.06 |
| MS-100 | 70.5 | 0.2 | 73.5 | 0.1 | 11 | 1 | 2.27 | 0.03 | 3.22 | 0.04 |
| MS-101 | 70.7 | 0.1 | 74.1 | 0.1 | 12 | 0 | 2.27 | 0.02 | 4.93 | 1.49 |
| MS-102 | 70.6 | 0.1 | 73.9 | 0.2 | 12 | 0 | 2.33 | 0.01 | 3.90 | 1.58 |
| MS-103 | 70.4 | 0.0 | 77.6 | 0.1 | 32 | 1 | 2.43 | 0.02 | 3.71 | 0.47 |
| MS-104 | 70.6 | 0.0 | 77.8 | 0.0 | 31 | 0 | 2.50 | 0.01 | 3.28 | 0.42 |
| MS-105 | 70.4 | 0.1 | 77.8 | 0.0 | 33 | 0 | 2.50 | 0.02 | 3.99 | 0.24 |
| MS-106 | 70.4 | 0.0 | 77.3 | 0.0 | 27 | 1 | 2.40 | 0.01 | 4.65 | 0.21 |
| MS-107 | 70.5 | 0.1 | 77.5 | 0.2 | 29 | 0 | 2.37 | 0.03 | 5.16 | 0.16 |
| MS-108 | 70.5 | 0.0 | 77.5 | 0.1 | 29 | 1 | 2.43 | 0.01 | 4.83 | 0.06 |
| MS-109 | 70.7 | 0.0 | 74.1 | 0.6 | 12 | 0 | 2.31 | 0.07 | 3.60 | 0.15 |
| MS-110 | 70.7 | 0.1 | 73.8* | | 15 | 0 | 2.22 | 0.04 | 5.05 | 0.18 |
| MS-111 | 70.9 | 0.4 | 74.0 | 0.1 | 14 | 0 | 2.36 | 0.03 | 2.73 | 0.15 |
| MS-112 | 70.4 | 0.1 | 73.6 | 0.1 | 11 | 1 | 2.21 | 0.04 | 3.88 | 0.21 |
| MS-113 | 70.5 | 0.1 | 77.6 | 0.0 | 31 | 0 | 2.46 | 0.02 | 4.53 | 0.18 |
| MS-114 | 70.4 | 0.1 | 77.7 | 0.1 | 32 | 0 | 2.40 | 0.01 | 3.84 | 0.12 |
| MS-115 | 70.5 | 0.1 | 77.8 | 0.0 | 32 | 0 | 2.52 | 0.02 | 3.93 | 0.14 |
| MS-116 | 70.6 | 0.1 | 77.4 | 0.4 | 28 | 1 | 2.40 | 0.02 | 5.25 | 0.13 |
| MS-117 | 70.8 | 0.0 | 74.0 | 0.1 | 12 | 0 | 2.32 | 0.03 | 3.22 | 0.11 |
| MS-118 | 70.6 | 0.1 | 77.6 | 0.1 | 30 | 1 | 2.46 | 0.03 | 3.33 | 0.13 |

*Only one of two DSF analysis showed a Tm2 value

TABLE 13-continued

Analysis of additional biophysical characteristics of Round-2 PGDM1400 variant antibodies: thermal hold, solubility, and SINS

| Molecule Set | Thermal Hold: A350 Heated 68° C. in | Thermal Hold: A350 Heated 69.2° C. in | 9.4% PEG Solubility (Avg. n = 4) | Std Dev |
|---|---|---|---|---|
| MS-113 | 0.0885 | 0.3335 | 0.12 | 0.01 |
| MS-114 | 0.0882 | 0.1156 | 0.14 | 0.02 |
| MS-115 | 0.0808 | 0.1305 | 0.13 | 0.01 |
| MS-116 | 0.0863 | 0.3428 | 0.12 | 0.01 |
| MS-117 | 0.6592 | 0.5923 | 0.11 | 0.02 |
| MS-118 | 0.0812 | 0.1959 | 0.13 | 0.01 |

TABLE 14

Analysis of neutralization activity of selected Round-2 PGDM1400 variant antibodies against representative PGDM1400 sensitive virus panel (SC422661.8, RHPA4259.7, Du172.17, BB1012-11.TC21, CNE52, 0260.v5.c36) in TZM.bl cells. Loss of potency are values > 3-fold of control value.

| Molecule | SC422661.8 | | RHPA4259.7 | | DU172.17 | | BB1012-11.TC21 | | CNE52 | | 0260.v5.c36 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.398 | 1.954 | 0.406 | 1.097 | 3.234 | 9.188 | 0.057 | 0.157 | 0.609 | 5.122 | 0.040 | 0.143 |
| MS-194 | 0.194 | 0.975 | 0.369 | 1.693 | 2.144 | 5.980 | 0.032 | 0.089 | 0.259 | 2.183 | 0.027 | 0.095 |
| MS-93 | 0.333 | 2.705 | 0.358 | 1.605 | 3.240 | 9.142 | 0.034 | 0.118 | 0.636 | 5.599 | 0.034 | 0.116 |
| MS-94 | 0.315 | 1.229 | 0.358 | 0.985 | 3.027 | 11.204 | 0.055 | 0.146 | 0.455 | 5.180 | 0.027 | 0.095 |
| MS-95 | 0.433 | 2.883 | 0.208 | 0.690 | 1.970 | 7.068 | 0.044 | 0.117 | 0.567 | 5.048 | 0.022 | 0.060 |
| MS-96 | 0.397 | 2.817 | 0.252 | 1.137 | 3.579 | 12.966 | 0.047 | 0.195 | 0.543 | 5.358 | 0.026 | 0.093 |
| MS-97 | 0.311 | 2.089 | 0.183 | 0.824 | 2.213 | 7.535 | 0.040 | 0.130 | 0.214 | 1.622 | 0.028 | 0.096 |
| MS-98 | 0.301 | 2.136 | 0.146 | 0.676 | 1.441 | 6.335 | 0.025 | 0.114 | 0.237 | 1.907 | 0.019 | 0.068 |
| MS-99 | 0.294 | 1.456 | 0.257 | 0.718 | 1.949 | 7.141 | 0.032 | 0.084 | 0.219 | 1.798 | 0.024 | 0.087 |
| MS-100 | 0.184 | 1.309 | 0.142 | 0.694 | 1.562 | 5.255 | 0.029 | 0.095 | 0.147 | 2.015 | 0.019 | 0.053 |
| MS-101 | 0.251 | 1.876 | 0.227 | 0.816 | 2.410 | 6.878 | 0.037 | 0.121 | 0.145 | 1.231 | 0.025 | 0.069 |
| MS-102 | 0.170 | 1.207 | 0.178 | 0.649 | 1.161 | 5.910 | 0.031 | 0.100 | 0.211 | 1.869 | 0.019 | 0.053 |
| MS-103 | 0.408 | 1.986 | 0.290 | 1.328 | 2.681 | 10.194 | 0.046 | 0.155 | 0.432 | 4.179 | 0.030 | 0.104 |
| MS-104 | 0.277 | 1.520 | 0.227 | 1.021 | 2.578 | 9.413 | 0.032 | 0.137 | 0.509 | 6.483 | 0.024 | 0.084 |
| MS-105 | 0.440 | 3.509 | 0.270 | 1.245 | 3.058 | 11.527 | 0.038 | 0.124 | 0.441 | 5.037 | 0.032 | 0.110 |
| MS-106 | 0.201 | 1.075 | 0.143 | 0.720 | 1.487 | 8.035 | 0.031 | 0.132 | 0.420 | 4.307 | 0.018 | 0.066 |
| MS-107 | 0.362 | 2.070 | 0.219 | 0.949 | 2.576 | 13.931 | 0.035 | 0.111 | 0.389 | 5.290 | 0.034 | 0.109 |
| MS-108 | 0.148 | 1.250 | 0.178 | 1.103 | 1.714 | 13.591 | 0.027 | 0.110 | 0.265 | 3.505 | 0.028 | 0.088 |
| MS-109 | 0.233 | 1.749 | 0.182 | 0.794 | 1.144 | 8.759 | 0.021 | 0.087 | 0.206 | 1.951 | 0.027 | 0.089 |
| MS-110 | 0.243 | 1.191 | 0.180 | 0.817 | 0.847 | 7.298 | 0.033 | 0.104 | 0.210 | 1.308 | 0.026 | 0.088 |
| MS-111 | 0.285 | 1.028 | 0.178 | 0.802 | 1.761 | 6.270 | 0.029 | 0.093 | 0.220 | 1.306 | 0.024 | 0.066 |
| MS-112 | 0.275 | 1.435 | 0.195 | 0.661 | 1.772 | 4.908 | 0.032 | 0.129 | 0.133 | 1.155 | 0.022 | 0.059 |
| MS-113 | 0.354 | 2.116 | 0.206 | 0.696 | 2.223 | 8.271 | 0.026 | 0.109 | 0.502 | 5.045 | 0.026 | 0.092 |
| MS-114 | 0.236 | 2.210 | 0.237 | 1.244 | 1.658 | 7.738 | 0.033 | 0.136 | 0.444 | 3.607 | 0.030 | 0.105 |
| MS-115 | 0.202 | 1.030 | 0.237 | 0.647 | 1.833 | 5.035 | 0.024 | 0.106 | 0.489 | 5.459 | 0.025 | 0.067 |
| MS-116 | 0.185 | 1.063 | 0.187 | 0.663 | 1.973 | 6.710 | 0.030 | 0.139 | 0.321 | 3.090 | 0.024 | 0.067 |
| MS-117 | 0.168 | 1.332 | 0.201 | 0.715 | 1.908 | 6.489 | 0.030 | 0.099 | 0.206 | 1.726 | 0.021 | 0.057 |
| MS-118 | 0.244 | 2.053 | 0.164 | 0.785 | 2.117 | 8.294 | 0.036 | 0.117 | 0.420 | 3.400 | 0.019 | 0.069 |

Assay Set up: mAbs tested at primary concentration of 25 ug/ml and titrated 5-fold 7x (duplicate wells).

TABLE 15

Analysis of neutralization activity of selected Round-2 PGDM1400 variant antibodies against additional representative PGDM1400 sensitive virus panel (263-8, SC05.8C11.2344, X1193_c1, Ce1176_A3, AC10.0.29, 6952.v1.c20) in TZM.bl cells. Loss of potency are values > 3-fold of control value.

| Molecule | 263-8 | | SC05.8C11.2344 | | X1193_c1 | | Ce1176_A3 | | AC10.0.29 | | 6952.v1.c20 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.019 | 0.066 | 0.781 | 2.641 | 0.121 | 0.779 | 0.517 | 13.569 | 0.073 | 0.368 | 0.257 | 3.988 |
| MS-194 | 0.012 | 0.045 | 0.710 | 2.254 | 0.072 | 0.456 | 0.189 | 3.835 | 0.057 | 0.219 | 1.560 | 3.014 |
| MS-93 | 0.018 | 0.065 | 0.749 | 2.483 | 0.088 | 0.543 | 0.239 | 5.326 | 0.058 | 0.301 | 0.259 | 4.307 |
| MS-94 | 0.014 | 0.047 | 0.739 | 2.505 | 0.123 | 0.548 | 0.371 | 11.686 | 0.079 | 0.299 | 0.238 | 3.670 |
| MS-95 | 0.013 | 0.047 | 0.702 | 1.789 | 0.111 | 0.467 | 0.203 | 5.384 | 0.076 | 0.270 | 0.229 | 6.261 |
| MS-96 | 0.018 | 0.064 | 1.072 | 3.397 | 0.113 | 0.677 | 0.248 | 5.848 | 0.064 | 0.253 | 0.558 | 8.561 |
| MS-97 | 0.015 | 0.052 | 1.022 | 2.630 | 0.101 | 0.588 | 0.125 | 1.594 | 0.057 | 0.282 | 0.147 | 0.917 |
| MS-98 | 0.009 | 0.033 | 0.590 | 1.897 | 0.088 | 0.369 | 0.102 | 2.361 | 0.067 | 0.245 | 0.109 | 1.596 |
| MS-99 | 0.011 | 0.041 | 0.759 | 2.492 | 0.130 | 0.570 | 0.074 | 1.252 | 0.072 | 0.328 | 0.217 | 1.993 |
| MS-100 | 0.006 | 0.026 | 0.531 | 1.769 | 0.058 | 0.358 | 0.048 | 0.905 | 0.042 | 0.211 | 0.182 | 1.676 |
| MS-101 | 0.011 | 0.041 | 0.819 | 2.686 | 0.098 | 0.602 | 0.043 | 1.942 | 0.045 | 0.221 | 0.254 | 3.509 |

TABLE 15-continued

Analysis of neutralization activity of selected Round-2 PGDM1400 variant antibodies against additional representative PGDM1400 sensitive virus panel (263-8, SC05.8C11.2344, X1193_c1, Ce1176_A3, AC10.0.29, 6952.v1.c20) in TZM.bl cells. Loss of potency are values > 3-fold of control value.

| Molecule | 263-8 | | SC05.8C11.2344 | | X1193_c1 | | Ce1176_A3 | | AC10.0.29 | | 6952.v1.c20 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| MS-102 | 0.007 | 0.027 | 0.527 | 1.418 | 0.071 | 0.412 | 0.039 | 2.747 | 0.047 | 0.168 | 0.162 | 2.527 |
| MS-103 | 0.018 | 0.070 | 0.707 | 2.436 | 0.112 | 0.502 | 0.172 | 3.134 | 0.070 | 0.334 | 0.485 | 5.952 |
| MS-104 | 0.014 | 0.052 | 0.512 | 1.726 | 0.063 | 0.388 | 0.218 | 6.109 | 0.041 | 0.208 | 0.457 | 8.608 |
| MS-105 | 0.017 | 0.062 | 0.794 | 2.725 | 0.067 | 0.417 | 0.172 | 3.393 | 0.051 | 0.394 | 0.706 | 9.489 |
| MS-106 | 0.011 | 0.039 | 0.411 | 1.439 | 0.093 | 0.394 | 0.099 | 3.432 | 0.062 | 0.299 | 0.216 | 3.799 |
| MS-107 | 0.016 | 0.055 | 0.658 | 2.281 | 0.130 | 0.570 | 0.147 | 3.986 | 0.079 | 0.397 | 0.457 | 8.867 |
| MS-108 | 0.012 | 0.042 | 0.428 | 1.450 | 0.083 | 0.545 | 0.117 | 3.843 | 0.045 | 0.216 | 0.323 | 3.366 |
| MS-109 | 0.010 | 0.033 | 0.546 | 1.852 | 0.073 | 0.467 | 0.078 | 5.834 | 0.040 | 0.199 | 0.188 | 1.744 |
| MS-110 | 0.010 | 0.038 | 0.914 | 3.100 | 0.106 | 0.677 | 0.097 | 2.496 | 0.076 | 0.285 | 0.195 | 2.120 |
| MS-111 | 0.016 | 0.045 | 0.496 | 1.694 | 0.109 | 0.352 | 0.082 | 3.121 | 0.061 | 0.258 | 0.213 | 2.097 |
| MS-112 | 0.013 | 0.037 | 0.501 | 1.675 | 0.069 | 0.293 | 0.068 | 2.033 | 0.056 | 0.262 | 0.160 | 1.467 |
| MS-113 | 0.018 | 0.052 | 0.573 | 1.942 | 0.098 | 0.421 | 0.182 | 6.054 | 0.052 | 0.245 | 0.351 | 5.030 |
| MS-114 | 0.018 | 0.066 | 0.810 | 3.860 | 0.124 | 0.404 | 0.139 | 7.391 | 0.066 | 0.313 | 0.146 | 1.369 |
| MS-115 | 0.013 | 0.037 | 0.436 | 1.514 | 0.080 | 0.274 | 0.180 | 6.301 | 0.049 | 0.249 | 0.303 | 4.700 |
| MS-116 | 0.011 | 0.042 | 0.456 | 1.617 | 0.064 | 0.222 | 0.145 | 3.116 | 0.052 | 0.258 | 0.341 | 7.508 |
| MS-117 | 0.010 | 0.029 | 0.432 | 1.482 | 0.064 | 0.226 | 0.113 | 2.173 | 0.051 | 0.252 | 0.208 | 3.840 |
| MS-118 | 0.011 | 0.039 | 0.449 | 1.538 | 0.085 | 0.287 | 0.260 | 8.123 | 0.056 | 0.273 | 0.392 | 12.192 |

Assay Set up: mAbs tested at primary concentration of 25 μg/ml and titrated 5-fold 7x (duplicate wells)

Example 5. Pharmacokinetic Characterization of PGDM1400 Variant Antibodies

Mice were injected with PGDM1400 variant antibodies and pharmacokinetic properties of the variants was tested in blood samples collected up to 28 days (e.g., up to about 1 hour, 2 hour, 3 hour, 4 hour, 5 hour, 6 hour, 7 hour, 8 hour, 9 hour, 10 hour, 11 hour, 12 hour, 13 hour, 14 hour 15 hour, 16 hour, 17 hour, 18 hour, 19 hour, 20 hour, 21 hour, 22 hour, 23 hour, 1 day, 2 day, 3 day, 4 day, 5 day, 6 day, 7 day, 8 day, 9 day, 10 day, 11 day, 12 day, 13 day, 14 day, 15 day, 16 day, 17 day, 18 day, 19 day, 20 day, 21 day, 22 day, 23 day, 24 day, 25 day, 26 day, 27 day, or 28 day) post-infusion. Infusion and sample collection were done as per the schedule outlined in Table 16.

TABLE 16

Dosing and blood sampling schedule

| Group | 3BNC117 Test mAb (Pettit 650) | TA Dose, mg/kg | Route, Frequency | # of mice | Mouse Strain | Blood Sampling Time |
|---|---|---|---|---|---|---|
| 1 | MS-65: PGDM1400 | 10 | IV, 1X | 4 | Tg276 | 1 h, 8 h, 2 d, 5 d, 7d, 10 d, 14 d, 21 d, 28 d |
| 2 | MS-119: PGDM1400-LS | 10 | IV, 1X | 4 | Tg276 | 1 h, 8 h, 2 d, 5 d, 7 d, 10 d, 14 d, 21 d, 28 d |
| 3 | MS-93: Optimized PGDM1400-LS | 10 | IV, 1X | 4 | Tg27S6 | 1 h, 8 h, 2 d, 5 d, 7 d, 10 d, 14 d, 21 d, 28 d |
| 4 | MS-103: Optimized PGDM1400-LS | 10 | IV, 1X | 4 | Tg276 | 1 h, 8 h, 2 d, 5 d, 7 d, 10 d, 14 d, 21 d, 28 d |
| 5 | MS-115: Optimized PGDM1400-LS | 10 | IV, 1X | 4 | Tg276 | 1 h, 8 h, 2 d, 5 d, 7 d, 10 d, 14 d, 21 d, 28 d |

Pharmacokinetics of PGDM1400 variant antibodies was studied by antibody binding assays that were adapted from validated BAMA (binding assay multiplex assay) for detection of antibodies specific for HIV-1 antigens. The assays were done in 96-well plates using beads coupled to neutravidin and bound to biotinylated mouse anti-human IgG Fc antibody. Infused monoclonal antibody (mAb) was detected with an antibody to the human Ig Kappa chain. Blood samples (up to 28 day post-infusion) were tested at 1:200, 1:500, 1:1000, and 1:2000 dilutions. All samples, standards and controls were tested in duplicate and several samples were tested in 2 separate assays to confirm observed concentration. Samples were received in plates arranged by mAb variant received and timepoint post infusion, and diluted at 1:10. Standard curves for each mAb were titrated in assay diluent and applied in a 5PL (five parameter logistic) curve algorithm to determine the concentration of the corresponding infused mAb variant. Standard curve EC50's were tracked in Levey Jennings charts against historical means obtained from development assays. Controls included blank wells, blank (no antigen) beads, and antigen-specific controls.

Figure 4A:
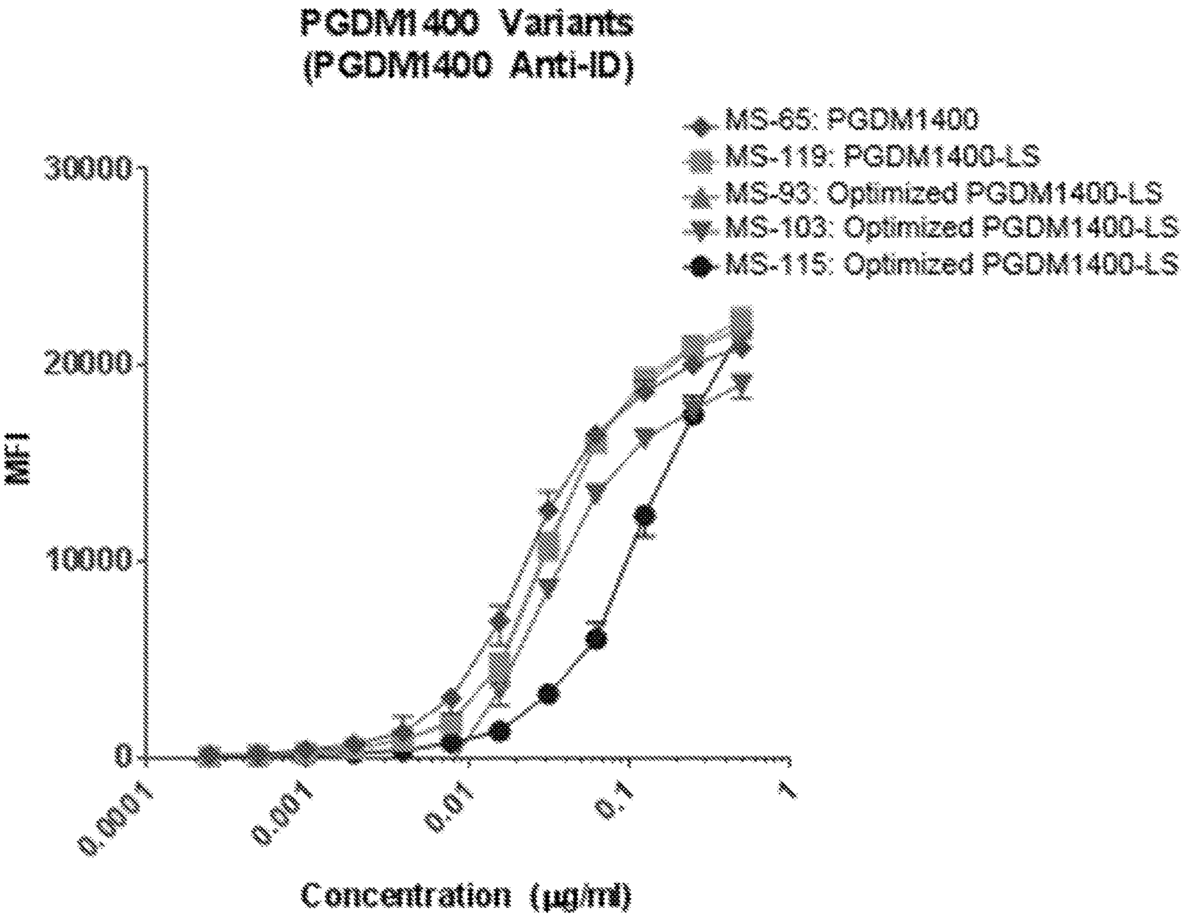
FIGS. 4A and 4B are graphs showing binding affinity of a parental PGDM1400 anti-ID antibody (FIG. 4A) and an anti-human IgG Fc antibody (FIG. 4B) for the indicated PGDM1400 antibody variants in post-infusion blood sample from mice that have been injected with the antibody variant.
Figure 4B:
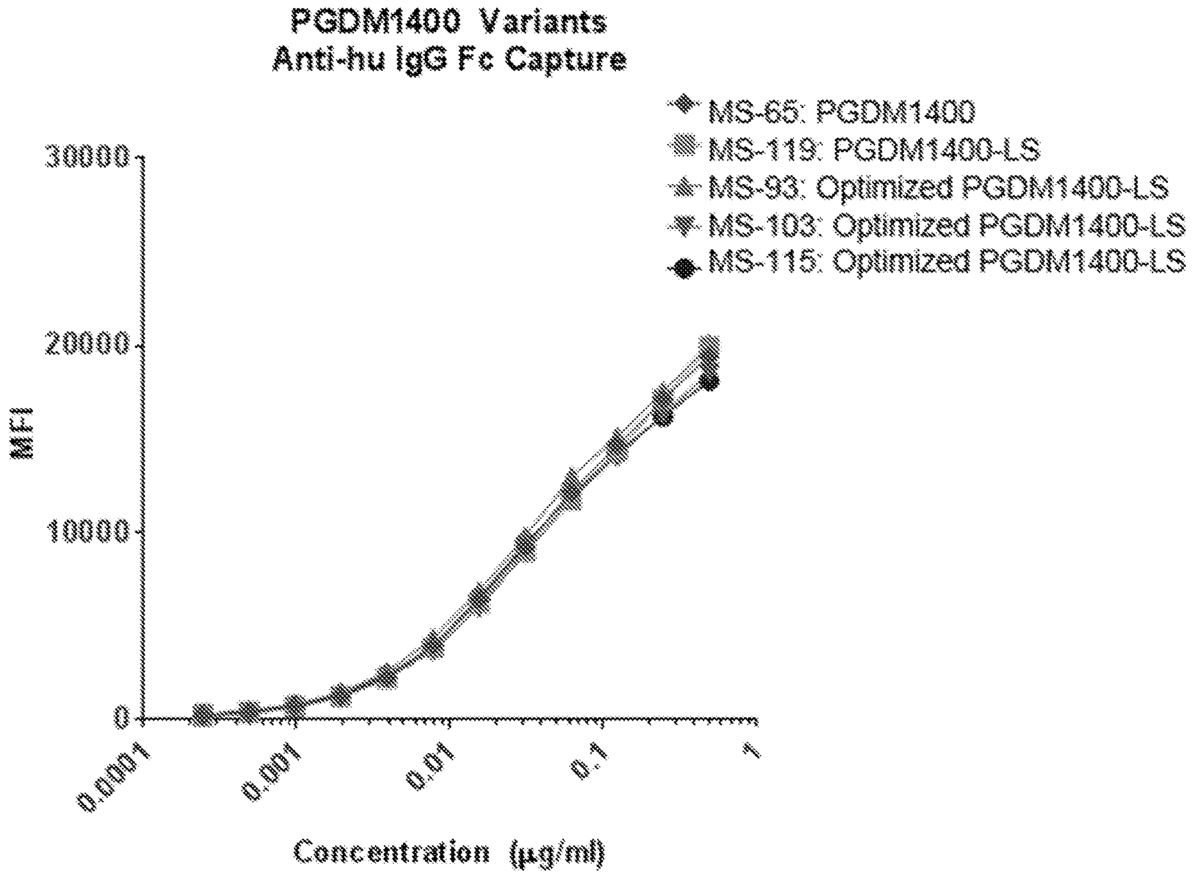
Figure 5:
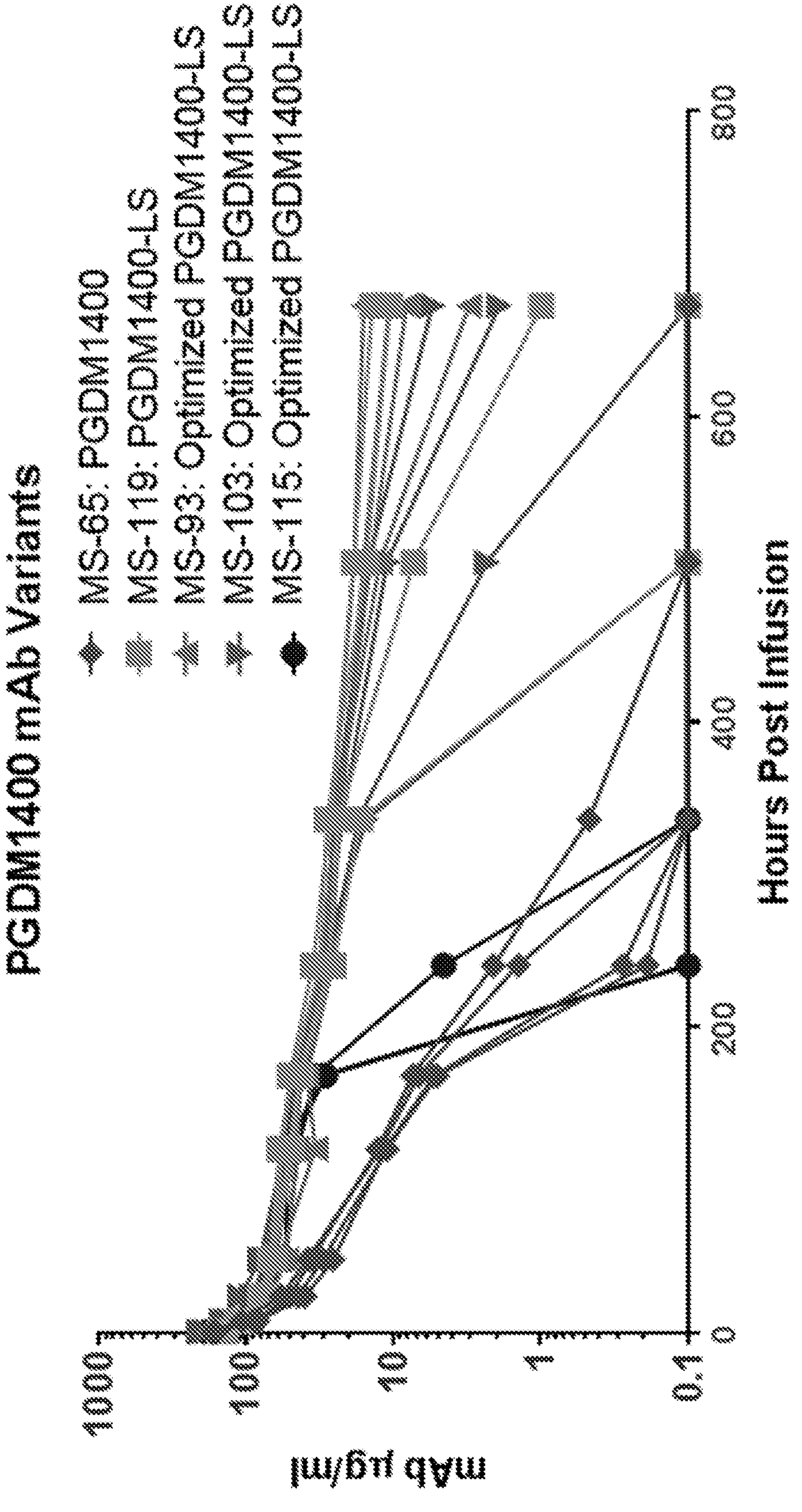
FIG. 5 is a graph showing decay kinetics of PGDM1400 antibody variants at different time points in blood sample from mice that have been injected with the antibody variants.

Results from the binding assays demonstrated that the parental PGDM1400 anti-ID antibody did not have equal affinity for the PGDM1400 variant antibodies (FIG. 4A), while all the variants appeared to bind with very similar affinity to the anti-human IgG Fc capture antibody when titrated as standard curves (FIG. 4B). Similar levels of all the tested PGDM1400 variant antibodies (134-147 μg/ml) were detected 1 hour post-infusion. However, of the different PGDM1400 variant antibodies tested, MS-93 appeared to have the slowest decay kinetics; all 4 mice injected with MS-93 had detectable levels of mAb at day 28 post-infusion, as opposed to MS-115 (only 1 mouse with detectable mAb by day 10 post-infusion), MS-119 (3 mice with detectable mAb at day 28 post-infusion), and MS-103 (3 mice with detectable mAb by day 21 post-infusion) (Table 17; FIG. 5).

TABLE 17

| Concentration of antibody in post-infusion blood sample | | | | | |
|---|---|---|---|---|---|
| | Average Concentration of Responders (μg/ml) | | | | |
| Hours Post Infusion | MS-65: PGDM1400 | MS-119: PGDM1400-LS | MS-93: Optimized PGDM1400-LS | MS-103: Optimized PGDM1400-LS | MS-115: Optimized PGDM1400-LS |
| 1 | 164.39 | 148.10 | 161.72 | 199.86 | 144.68 |
| 8 | 90.72 | 109.28 | 108.16 | 133.67 | 98.09 |
| 24 | 48.45 | 76.75 | 74.86 | 94.88 | 73.40 |
| 48 | 32.49 | 66.06 | 60.70 | 73.70 | 58.50 |
| 120 | 11.83 | 54.07 | 43.82 | 53.96 | 49.54 |
| 168 | 6.13 | 46.41 | 42.03 | 45.52 | 30.91 |
| 240 | 1.00 | 30.00 | 28.15 | 29.75 | 4.57 |
| 336 | 0.47 | 23.89 | 24.47 | 20.09 | |
| 504 | | 13.75 | 15.31 | 9.40 | |
| 672 | | 8.50 | 9.44 | 3.69 | |

Example 6. Treatment of a Subject with a PGDM1400 Variant Antibody or Antigen-Binding Fragment Thereof One or more PGDM1400 variant antibodies or antigen-binding fragments thereof described herein, or a composition containing the same can be administered to a subject, such as a human (e.g., a HIV-infected human or a human at risk of HIV transmission) in order to treat or prevent HIV infection (e.g., HIV-1 infection). Administration of the one or more PGDM1400 variant antibodies or antigen-binding fragments thereof or a composition containing the same, for instance, can reduce proviral DNA (e.g., to below about 1,000 DNA copies/$10^6$ cells or to an undetectable level) in a tissue (e.g., lymph node tissue, gastrointestinal tissue, and/or peripheral blood), decrease plasma viral load (e.g., to less than 3,500 RNA copies/ml or to an undetectable level), increase HIV-specific cell-mediated immune response and/or humoral immune response, and/or decrease viral replication in the subject. For instance, an HIV-infected human can be treated by administering one or more PGDM1400 variant antibodies or antigen-binding fragments thereof described herein or a composition containing the same by an appropriate route (e.g., intravenously) at a particular dosage (e.g., about 0.01-5000 mg or about 0.01-100 mg/kg of the antibody or antigen-binding fragment thereof) one or more times daily, weekly, every two weeks, every three weeks, or monthly. A single dose or more than one dose of the one or more PGDM1400 variant antibodies or antigen-binding fragments thereof described herein or a composition containing the same can be administered to the subject over a course of days, weeks, months, or years.

The progression of HIV infection that is treated with the PGDM1400 variant antibody or antigen-binding fragment thereof described herein or a composition containing the same can be monitored by any one or more of several established methods. A physician can monitor the subject by direct observation in order to evaluate how the symptoms exhibited by the subject have changed in response to treatment (e.g., by evaluation of proviral DNA, plasma viral load and/or viral replication in the subject). Based on such observations, a physician may prescribe higher/lower dosages or more/less frequent dosing of the PGDM1400 variant antibody or antigen-binding fragment or a composition containing the same in subsequent rounds of treatment.

Example 7. Treatment of a Subject with a PGDM1400 Variant Antibody or Antigen-Binding Fragment Thereof in Combination with an Immunotherapy Agent The PGDM1400 variant antibody or antigen-binding fragment described herein or a composition containing the same (e.g., MS-93, MS-94, MS-95, MS-96, MS-103, MS-104, MS-105, MS-106, MS-107, MS-108, MS-113, MS-114, MS-115, MS-116, and MS-118) can be administered to a subject, such as a human (e.g., a HIV-infected human or a human at risk of HIV transmission) in combination with (for instance, admixed with, co-administered with, or administered separately from) one or more: (i) immunomodulators (e.g., AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, a gp120-depleted, inactivated $HZ_{321}$ virus (e.g., REMUNE™), CD4 (e.g., recombinant soluble CD4), rCD4-IgG hybrids, SK&F106528 Soluble T4, Thymopentin, Tumor Necrosis Factor, or Infliximab); (ii) reservoir activators, such as a PKC agonist (e.g., a phorbol ester, a macrocyclic lactone such as bryostatin-1, or a diterpene such as an ingenol compound), a cytokine or chemokine (e.g., interleukin (IL)-7, IL-15, or interferon-alpha (IFN-α)), a Toll-like receptor (TLR) agonist (e.g., a TLR 1/2 agonist (e.g., Pam3CSK4), a TLR3 agonist (e.g., Poly-ICLC), a TLR5 agonist (e.g., flagellin), a TLR7 agonist (e.g., GS-9620), or a TLR9 agonist (e.g., MGN1703 and CpG7909)), an immune checkpoint inhibitor (e.g., anti-PD-1 monoclonal antibody, an anti-PD-1 ligand (PD-L1) monoclonal antibody, or an anti-CTLA-4 monoclonal antibody), a histone deacetylase (HDAC) inhibitor (e.g., romidepsin, vorinostat, belinostat, LAQ824, panobinostat, entinostat, C1994, or mocetinostat), or a small molecule reservoir activator (e.g., disulfiram, a benzotriazole derivative (e.g., 3-Hydroxy-1,2,3-benzotriazin-4 ((3H)-one (HO-DHBt); a SMAC mimetic), or a BRG-Brahma Associated Factor (BAF) inhibitor (e.g., caffeic acid phenethyl ester or pyrimethamine)); (iii) antiretroviral agent (ARV) (e.g., lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc, raltegravir, ibalizumab, IL-2, IL-12, or alpha-epibromide); and/or one, two, three, or more different HIV-specific broadly neutralizing antibodies (bnAb), such as a CD4 binding site (CD4bs)-specific antibody (e.g., 3BNC117 or VRC07-523), an N332 glycan-dependent antibody (e.g., PGT121), or a V2-specific antibody (e.g., CAP256-VRC26 or PGDM1400). The one or more immunomodulator(s), reservoir activator(s), ARV(s), and/or HIV-specific bnAb(s) can be administered prior to (e.g., 1 year, 9 months, 6 months, 3 months, 1 month, 3 weeks, 2 weeks, 1 week, 5 days, 3 days, 1 day, 18 hours, 12 hours, 6 hours, or 1 hour prior to), concurrently with and/or after (e.g., 1 year, 9 months, 6 months, 3 months, 1 month, 3 weeks, 2 weeks, 1 week, 5 days, 3 days, 1 day, 18 hours, 12 hours, 6 hours, or 1 hour after) the administration of the PGDM1400 variant antibody or antigen-binding fragment described herein or a composition containing the same. Administration routes, dosage and frequency of administration of the PGDM1400 variant antibody or antigen-binding fragment or a composition containing the same has been exemplified in the aforementioned Example 6.

The progression of HIV infection that is treated with the PGDM1400 variant antibody or antigen-binding fragment thereof in combination with the one or more immunomodulator(s), reservoir activator(s), ARV(s), and/or HIV-specific bnAb(s) can be monitored by any one or more of several established methods. A physician can monitor the subject by direct observation in order to evaluate how the symptoms exhibited by the subject have changed in response to treatment (e.g., by evaluation of proviral DNA, plasma viral load and/or viral replication in the subject). Based on such observations, a physician may prescribe higher/lower dosages or more/less frequent dosing of the PGDM1400 variant antibody or antigen-binding fragment or a composition containing the same in combination with the one or more immunomodulator(s), reservoir activator(s), ARV(s), and/or HIV-specific bnAb(s) in subsequent rounds of treatment.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

The invention claimed is:

1. An antibody or antigen-binding fragment thereof comprising:

(a) a heavy chain variable domain comprising a sequence with at least 98% sequence identity to SEQ ID NO: 136; and (b) a light chain variable domain comprising a sequence with at least 97% sequence identity to SEQ ID NO: 135 and an F2I mutation, wherein the antibody is a V2-specific antibody and the antibody or antigen-binding fragment thereof comprises a heavy chain (HC) complementarity determining region (CDR) HC-CDR1 comprising the amino acid sequence of SEQ ID NO: 12, a HC-CDR2 comprising the amino acid sequence of SEQ ID NO: 14, a HC-CDR3 comprising the amino acid sequence of SEQ ID NO: 16, a light chain (LC)-CDR1 comprising the amino acid sequence of SEQ ID NO: 4, a LC-CDR2 comprising the amino acid sequence of SEQ ID NO: 6, and a LC-CDR3 comprising the amino acid sequence of SEQ ID NO: 8.

2. The antibody or antigen-binding fragment thereof of claim 1, wherein the antibody comprises:

(a) a heavy chain variable domain comprising the sequence of SEQ ID NO: 136 and a light chain variable domain comprising the sequence of SEQ ID NO: 144;

(b) a heavy chain variable domain comprising the sequence of SEQ ID NO: 136 and a light chain variable domain comprising the sequence of SEQ ID NO: 164;

(c) a heavy chain variable domain comprising the sequence of SEQ ID NO: 175 and a light chain variable domain comprising the sequence of SEQ ID NO: 174;

(d) a heavy chain variable domain comprising the sequence of SEQ ID NO: 136 and a light chain variable domain comprising the sequence of SEQ ID NO: 176;

(e) a heavy chain variable domain comprising the sequence of SEQ ID NO: 136 and a light chain variable domain comprising the sequence of SEQ ID NO: 177;

(f) a heavy chain variable domain comprising the sequence of SEQ ID NO: 136 and a light chain variable domain comprising the sequence of SEQ ID NO: 178;

(g) a heavy chain variable domain comprising the sequence of SEQ ID NO: 136 and a light chain variable domain comprising the sequence of SEQ ID NO: 179;

(h) a heavy chain variable domain comprising the sequence of SEQ ID NO: 136 and a light chain variable domain comprising the sequence of SEQ ID NO: 187;

(i) a heavy chain variable domain comprising the sequence of SEQ ID NO: 136 and a light chain variable domain comprising the sequence of SEQ ID NO: 188;

(j) a heavy chain variable domain comprising the sequence of SEQ ID NO: 136 and a light chain variable domain comprising the sequence of SEQ ID NO: 189;

(k) a heavy chain variable domain comprising the sequence of SEQ ID NO: 136 and a light chain variable domain comprising the sequence of SEQ ID NO: 190;

(l) a heavy chain variable domain comprising the sequence of SEQ ID NO: 136 and a light chain variable domain comprising the sequence of SEQ ID NO: 191;

(m) a heavy chain variable domain comprising the sequence of SEQ ID NO: 136 and a light chain variable domain comprising the sequence of SEQ ID NO: 196;

(n) a heavy chain variable domain comprising the sequence of SEQ ID NO: 136 and a light chain variable domain comprising the sequence of SEQ ID NO: 197;

(o) a heavy chain variable domain comprising the sequence of SEQ ID NO: 136 and a light chain variable domain comprising the sequence of SEQ ID NO: 198;

(p) a heavy chain variable domain comprising the sequence of SEQ ID NO: 136 and a light chain variable domain comprising the sequence of SEQ ID NO: 199; or (q) a heavy chain variable domain comprising the sequence of SEQ ID NO: 136 and a light chain variable domain comprising the sequence of SEQ ID NO: 201.

3. The antibody or antigen-binding fragment thereof of claim 2, wherein the antibody or antigen-binding fragment thereof is (d).

4. The antibody or antigen-binding fragment thereof of claim 1, wherein the antibody or antigen-binding fragment thereof exhibits one or more of the following properties:

(a) increased solubility in a PEG 10,000 concentration of 6-10%;

(b) increased stability at a pH less than pH 5.0;

(c) increased thermal stability at a temperature in the range of 20-95° C.; and/or (d) increased chemical stability, wherein the antibody or antigen-binding fragment thereof is resistant to chemical denaturation by at least 2M guanidine hydrochloride (GuHCl) or greater, as compared to an antibody or antigen-binding fragment thereof lacking the F2I mutation in the heavy chain variable domain and/or the light chain variable domain.

5. The antibody or antigen-binding fragment thereof of claim 1, wherein the antibody or antigen-binding fragment thereof exhibits one or more of the following properties:

(a) increased storage stability, wherein the antibody or antigen-binding fragment thereof:

(i) does not aggregate during storage over a period of time, wherein optionally the period of time is about 2 days;

(ii) exhibits more than about 60% high monomer content and/or less than about 10% low oligomer content; and (b) increased manufacturability, wherein the antibody or antigen-binding fragment thereof does not aggregate during manufacture.

6. The antibody or antigen-binding fragment thereof of claim 1, wherein the antibody or antigen-binding fragment thereof is selected from the group consisting of a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a single-domain antibody, an antibody-like protein scaffold, a domain antibody, a Fv fragment, a Fab fragment, a $F(ab')_2$ molecule, and a tandem scFv (taFv).

7. A polynucleotide encoding the antibody or antigen-binding fragment thereof of claim 1.

8. A vector comprising the polynucleotide of claim 7.

9. The vector of claim 8, wherein the vector is an expression vector or a viral vector.

10. The vector of claim 9, wherein:

(a) the expression vector is a prokaryotic or eukaryotic expression vector; or (b) the viral vector is selected from the group consisting of an adenovirus (Ad), a retrovirus, a poxvirus, an adeno-associated virus, a baculovirus, a herpes simplex virus, and a vaccinia virus.

11. The viral vector of claim 10, wherein:

(a) the adenovirus is a serotype 2, 5, 11, 12, 24, 26, 34, 35, 40, 48, 49, 50, 52, or Pan9 adenovirus, or a human, chimpanzee, or rhesus adenovirus;

(b) the retrovirus is a γ-retrovirus or a lentivirus; or (c) the vaccinia virus is a modified vaccinia Ankara (MVA).

12. An isolated host cell comprising the polynucleotide of claim 7 or a vector comprising the polynucleotide.

13. A composition comprising the antibody or antigen-binding fragment thereof of claim 1, a polynucleotide encoding the antibody or antigen-binding fragment thereof, a vector comprising the polynucleotide, or a host cell comprising the polynucleotide or the vector.

14. The composition of claim 13, wherein the composition further comprises:

(a) a pharmaceutically acceptable carrier, excipient, or diluent;

(b) an immunomodulator;

(c) at least one reservoir activator;

(d) an antiretroviral agent (ARV); or (e) one, two, three, or more different HIV-specific broadly neutralizing antibodies (bnAb).

15. The composition of claim 14, wherein:

(a) the immunomodulator is one or more of AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, CD4, Thymopentin, Tumor Necrosis Factor, Infliximab, and a gp120-depleted, inactivated $HZ_{321}$ virus;

(b) the reservoir activator is a PKC agonist, a cytokine or chemokine, a Toll-like receptor (TLR) agonist, an immune checkpoint inhibitor, a histone deacetylase (HDAC) inhibitor, or a small molecule reservoir activator;

(c) the ARV comprises one or more of lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc, raltegravir, ibalizumab, IL-2, IL-12, or alpha-epibromide; or (d) the bnAb is a CD4 binding site (CD4bs)-specific antibody or a V2 glycan-dependent antibody.

16. The composition of claim 15, wherein:

(a) the PKC agonist comprises one or more of a phorbol ester; a macrocyclic lactone and/or a diterpene;

(b) the cytokine or chemokine comprises one or more of interleukin (IL)-7, IL-15, or interferon-alpha (IFN-α);

(c) the TLR agonist comprises one or more of a TLR 1/2 agonist; a TLR3 agonist; a TLR5 agonist; a TLR7 agonist; and/or a TLR9 agonist;

(d) the immune checkpoint inhibitor comprises one or more of an anti-PD-1 monoclonal antibody; an anti-PD-1 ligand (PD-L1) monoclonal antibody; and/or an anti-CTLA-4 monoclonal antibody;

(e) the HDAC inhibitor comprises one or more of romidepsin; vorinostat; belinostat; LAQ824;

panobinostat; entinostat; CI994; and/or mocetinostat;

(f) the small molecule reservoir activator comprises one or more of disulfiram; a benzotriazole derivative; a SMAC mimetic; or a BRG-Brahma Associated Factor (BAF) inhibitor;

(g) the CD4bs-specific antibody is 3BNC117 or VRC07-523; or (h) the V2 glycan dependent antibody is CAP256-VRC26.

17. The composition of claim 13, wherein the composition:

(a) is formulated for subcutaneous, intramuscular, intradermal, transdermal, intranasal, or oral administration, or administration as an infusion, wherein optionally the infusion is a continuous infusion or a bolus infusion;

(b) is formulated in a volume of about 1000 ml or less; or (c) is formulated to comprise about 0.01-5000 mg of the antibody or antigen-binding fragment thereof.

18. The antibody or antigen-binding fragment thereof of claim 2, wherein the antibody or antigen-binding fragment comprises the heavy chain variable domain comprising the sequence of SEQ ID NO: 136 and the light chain variable domain comprising the sequence of SEQ ID NO: 176.

19. The antibody or antigen-binding fragment thereof of claim 18, wherein the antibody or antigen-binding fragment thereof exhibits a half-life in a fluid of at least 1 hour in vitro or in vivo, wherein optionally the fluid is blood.

20. The antibody or antigen-binding fragment thereof of claim 2, wherein the antibody or antigen-binding fragment comprises the heavy chain variable domain comprising the sequence of SEQ ID NO: 136 and the light chain variable domain comprising the sequence of SEQ ID NO: 198.

* * * * *

SEQUENCE LISTING

```
<160> NUMBER OF SEQ ID NOS: 201

<210> SEQ ID NO 1
<211> LENGTH: 714
<212> TYPE: DNA
<213> ORGANISM: Homo sapiens

<400> SEQUENCE: 1

atgatgtcct ttgtctctct gctcctggtt ggcatcctat tccatgccac ccaggccgac     60

ttcgtgctga cccagtcccc tcactccctg tctgtgaccc ctggcgagtc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgacaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714

<210> SEQ ID NO 2
<211> LENGTH: 238
<212> TYPE: PRT
```

<213> ORGANISM: Homo sapiens

<400> SEQUENCE: 2

```
Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 3
<211> LENGTH: 48
<212> TYPE: DNA
<213> ORGANISM: Homo sapiens

<400> SEQUENCE: 3

```
aagtcctccc acagcctgat ccacggcgac cggaacaact acctggct                  48
```

<210> SEQ ID NO 4
<211> LENGTH: 16
<212> TYPE: PRT
<213> ORGANISM: Homo sapiens

<400> SEQUENCE: 4

```
Lys Ser Ser His Ser Leu Ile His Gly Asp Arg Asn Asn Tyr Leu Ala
1               5                   10                  15
```

<210> SEQ ID NO 5
<211> LENGTH: 21
<212> TYPE: DNA
<213> ORGANISM: Homo sapiens

<400> SEQUENCE: 5

```
ctggcctcct ccagagcctc t                                               21
```

<210> SEQ ID NO 6
<211> LENGTH: 7
<212> TYPE: PRT
<213> ORGANISM: Homo sapiens

<400> SEQUENCE: 6

Leu Ala Ser Ser Arg Ala Ser
1               5

<210> SEQ ID NO 7
<211> LENGTH: 27
<212> TYPE: DNA
<213> ORGANISM: Homo sapiens

<400> SEQUENCE: 7
atgcagggca gagagtcccc ctggacc 27

<210> SEQ ID NO 8
<211> LENGTH: 9
<212> TYPE: PRT
<213> ORGANISM: Homo sapiens

<400> SEQUENCE: 8

Met Gln Gly Arg Glu Ser Pro Trp Thr
1               5

<210> SEQ ID NO 9
<211> LENGTH: 1473
<212> TYPE: DNA
<213> ORGANISM: Homo sapiens

<400> SEQUENCE: 9
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggcaacac cctgaaaacc tacgacctgc actgggtgcg atccgtgcct 180
ggacagggac tgcagtggat gggctggatc tcccacgagg gcgacaagaa agtgatcgtg 240
gaacggttca aggccaaagt gaccatcgac tgggaccggt ctaccaacac cgcttacctg 300
cagctgtccg gcctgacctc tggcgatacc gccgtgtact actgcgccaa gggctccaag 360
caccggctga gagactacgc cctgtacgac gatgacggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540
ggaacagccg ctctgggctg cctcgtgaag gactacttcc ccgagcctgt gaccgtgtcc 600
tggaactctg gcgctctgac atccggcgtg cacaccttcc ctgctgtgct gcagtcctcc 660
ggcctgtact ccctgtcctc cgtcgtgacc gtgccttcca gctctctggg cacccagacc 720
tacatctgca acgtgaacca caagccctcc aacaccaagg tggacaagaa ggtggaaccc 780
aagtcctgcg acaagaccca cacctgtccc ccttgtcctg cccctgagct gctgggaggc 840
cctagcgtgt tcctgttccc tccaaagccc aaggacaccc tgatgatctc ccggaccccc 900
gaagtgacct gcgtggtggt ggatgtgtct cacgaggacc ctgaagtgaa gttcaattgg 960
tacgtggacg gcgtggaagt gcacaacgcc aagaccaagc ctagagagga acagtacaac 1020
tccacctacc gggtggtgtc cgtgctgacc gtgctgcacc aggattggct gaacggcaaa 1080
gagtacaagt gcaaggtgtc caacaaggct ctgcctgccc ccatcgaaaa gaccatctcc 1140
aaggccaagg gccagccccg ggaaccccag gtgtacacac tgcccccctag ccgggaagag 1200 atgaccaaga accaggtgtc cctgacctgt ctcgtgaaag gcttctaccc ctccgatatc 1260
gccgtggaat gggagtccaa cggccagcct gagaacaact acaagaccac ccctcccgtg 1320
ctggactccg acggctcatt cttcctgtac agcaagctga cagtggacaa gtcccggtgg 1380
cagcagggca acgtgttctc ctgctccgtg atgcacgagg ccctgcacaa ccactacacc 1440
cagaagtccc tgagcctgag ccccggcaaa tga 1473

<210> SEQ ID NO 10
<211> LENGTH: 490
<212> TYPE: PRT
<213> ORGANISM: Homo sapiens

<400> SEQUENCE: 10

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

```
Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490


<210> SEQ ID NO 11
<211> LENGTH: 18
<212> TYPE: DNA
<213> ORGANISM: Homo sapiens

<400> SEQUENCE: 11

aaaacctacg acctgcac                                                    18


<210> SEQ ID NO 12
<211> LENGTH: 6
<212> TYPE: PRT
<213> ORGANISM: Homo sapiens

<400> SEQUENCE: 12

Lys Thr Tyr Asp Leu His
1               5


<210> SEQ ID NO 13
<211> LENGTH: 51
<212> TYPE: DNA
<213> ORGANISM: Homo sapiens

<400> SEQUENCE: 13

tggatctccc acgagggcga caagaaagtg atcgtggaac ggttcaaggc c               51


<210> SEQ ID NO 14
<211> LENGTH: 17
<212> TYPE: PRT
<213> ORGANISM: Homo sapiens

<400> SEQUENCE: 14

Trp Ile Ser His Glu Gly Asp Lys Lys Val Ile Val Glu Arg Phe Lys
1               5                   10                  15

Ala
```

<210> SEQ ID NO 15
<211> LENGTH: 96
<212> TYPE: DNA
<213> ORGANISM: Homo sapiens

<400> SEQUENCE: 15
ggctccaagc accggctgag agactacgcc ctgtacgacg atgacggcgc cctgaactgg 60
gccgtggatg tggactacct gtccaacctg gaattc 96

<210> SEQ ID NO 16
<211> LENGTH: 32
<212> TYPE: PRT
<213> ORGANISM: Homo sapiens

<400> SEQUENCE: 16

Gly Ser Lys His Arg Leu Arg Asp Tyr Ala Leu Tyr Asp Asp Asp Gly
1 5 10 15

Ala Leu Asn Trp Ala Val Asp Val Asp Tyr Leu Ser Asn Leu Glu Phe
20 25 30

<210> SEQ ID NO 17
<211> LENGTH: 714
<212> TYPE: DNA
<213> ORGANISM: Artificial Sequence
<220> FEATURE:
<223> OTHER INFORMATION: Synthetic Construct

<400> SEQUENCE: 17
atgatgtcct ttgtctctct gctcctggtt ggcatcctat tccatgccac ccaggccgac 60
atcgtgctga cccagtcccc tcactccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 18
<211> LENGTH: 238
<212> TYPE: PRT
<213> ORGANISM: Artificial Sequence
<220> FEATURE:
<223> OTHER INFORMATION: Synthetic Construct

<400> SEQUENCE: 18

Met Met Ser Phe Val Ser Leu Leu Leu Val Gly Ile Leu Phe His Ala
1 5 10 15

Thr Gln Ala Asp Ile Val Leu Thr Gln Ser Pro His Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro

```
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 19
<211> LENGTH: 714
<212> TYPE: DNA
<213> ORGANISM: Artificial Sequence
<220> FEATURE:
<223> OTHER INFORMATION: Synthetic Construct

<400> SEQUENCE: 19

atgatgtcct ttgtctctct gctcctggtt ggcatcctat tccatgccac ccaggccgac      60

ttcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 20
<211> LENGTH: 238
<212> TYPE: PRT
<213> ORGANISM: Artificial Sequence
<220> FEATURE:
<223> OTHER INFORMATION: Synthetic Construct

<400> SEQUENCE: 20
```

```
Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 21
<211> LENGTH: 714
<212> TYPE: DNA
<213> ORGANISM: Artificial Sequence
<220> FEATURE:
<223> OTHER INFORMATION: Synthetic Construct

<400> SEQUENCE: 21

```
atgatgtcct ttgtctctct gctcctggtt ggcatcctat tccatgccac ccaggccgac      60

ttcgtgctga cccagtcccc tcactccctg cccgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714
```

<210> SEQ ID NO 22
<211> LENGTH: 238
<212> TYPE: PRT
<213> ORGANISM: Artificial Sequence
<220> FEATURE:
<223> OTHER INFORMATION: Synthetic Construct

<400> SEQUENCE: 22

Met Met Ser Phe Val Ser Leu Leu Leu Val Gly Ile Leu Phe His Ala
1 5 10 15

Thr Gln Ala Asp Phe Val Leu Thr Gln Ser Pro His Ser Leu Pro Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Asp Lys Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 23
<211> LENGTH: 714
<212> TYPE: DNA
<213> ORGANISM: Artificial Sequence
<220> FEATURE:
<223> OTHER INFORMATION: Synthetic Construct

<400> SEQUENCE: 23
atgatgtcct ttgtctctct gctcctggtt ggcatcctat tccatgccac ccaggccgac 60
ttcgtgctga cccagtcccc tcactccctg tctgtgaccc ctggcgagcc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420

```
atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

```
<210> SEQ ID NO 24
<211> LENGTH: 238
<212> TYPE: PRT
<213> ORGANISM: Artificial Sequence
<220> FEATURE:
<223> OTHER INFORMATION: Synthetic Construct

<400> SEQUENCE: 24

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 25
<211> LENGTH: 714
<212> TYPE: DNA
<213> ORGANISM: Artificial Sequence
<220> FEATURE:
<223> OTHER INFORMATION: Synthetic Construct

<400> SEQUENCE: 25

atgatgtcct ttgtctctct gctcctggtt ggcatcctat tccatgccac ccaggccgac     60

ttcgtgctga cccagtcccc tcactccctg tctgtgaccc ctggcgagtc cgcctccatc    120
```

```
tcctgcaagt cctcccacag cctgatccac ggcgaccgga acaactacct ggcttggtac    180

gtgcagaagc ctggccagtc accccagctg ctgatctacc tggcctcctc cagagcctct    240

ggcgtgcccg atagattctc cggctccggc agcgacaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

```
<210> SEQ ID NO 26
<211> LENGTH: 238
<212> TYPE: PRT
<213> ORGANISM: Artificial Sequence
<220> FEATURE:
<223> OTHER INFORMATION: Synthetic Construct

<400> SEQUENCE: 26

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Gln Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 27
<211> LENGTH: 714
<212> TYPE: DNA
```

<213> ORGANISM: Artificial Sequence
<220> FEATURE:
<223> OTHER INFORMATION: Synthetic Construct

<400> SEQUENCE: 27
atgatgtcct ttgtctctct gctcctggtt ggcatcctat tccatgccac ccaggccgac 60
ttcgtgctga cccagtcccc tcactccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 28
<211> LENGTH: 238
<212> TYPE: PRT
<213> ORGANISM: Artificial Sequence
<220> FEATURE:
<223> OTHER INFORMATION: Synthetic Construct

<400> SEQUENCE: 28

Met Met Ser Phe Val Ser Leu Leu Leu Val Gly Ile Leu Phe His Ala
1 5 10 15

Thr Gln Ala Asp Phe Val Leu Thr Gln Ser Pro His Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

```
Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 29
<211> LENGTH: 714
<212> TYPE: DNA
<213> ORGANISM: Artificial Sequence
<220> FEATURE:
<223> OTHER INFORMATION: Synthetic Construct

<400> SEQUENCE: 29

```
atgatgtcct ttgtctctct gctcctggtt ggcatcctat tccatgccac ccaggccgac      60

ttcgtgctga cccagtcccc tcactccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacactg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714
```

<210> SEQ ID NO 30
<211> LENGTH: 238
<212> TYPE: PRT
<213> ORGANISM: Artificial Sequence
<220> FEATURE:
<223> OTHER INFORMATION: Synthetic Construct

<400> SEQUENCE: 30

```
Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Thr Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 31
<211> LENGTH: 714
<212> TYPE: DNA
<213> ORGANISM: Artificial Sequence
<220> FEATURE:
<223> OTHER INFORMATION: Synthetic Construct

<400> SEQUENCE: 31

atgatgtcct ttgtctctct gctcctggtt ggcatcctat tccatgccac ccaggccgac      60

ttcgtgctga cccagtcccc tcactccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 32
<211> LENGTH: 238
<212> TYPE: PRT
<213> ORGANISM: Artificial Sequence
<220> FEATURE:
<223> OTHER INFORMATION: Synthetic Construct

<400> SEQUENCE: 32

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
```

```
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 33
<211> LENGTH: 714
<212> TYPE: DNA
<213> ORGANISM: Artificial Sequence
<220> FEATURE:
<223> OTHER INFORMATION: Synthetic Construct

<400> SEQUENCE: 33

atgatgtcct ttgtctctct gctcctggtt ggcatcctat tccatgccac ccaggccgac      60

ttcgtgctga cccagtcccc tcactccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcgtctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 34
<211> LENGTH: 238
<212> TYPE: PRT
<213> ORGANISM: Artificial Sequence
<220> FEATURE:
<223> OTHER INFORMATION: Synthetic Construct

<400> SEQUENCE: 34

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45
```

```
Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Val Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 35
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 35

```
atgatgtcct ttgtctctct gctcctggtt ggcatcctat tccatgccac ccaggcccag     60

gtgcagctgg tgcagtccgg acccgaagtg cgaaagcctg gcacctccgt gaaggtgtcc    120

tgcaaggcct ctggcaacac cctgaaaacc tacgacctgc actgggtgcg atccgtgcct    180

ggacagggac tgcagtggat gggctggatc tcccacgagg gcgacaagaa agtgatcgtg    240

gaacggttca aggccaaagt gaccatcgac tgggaccggt ctaccaacac cgcttacctg    300

cagctgtccg gcctgacctc tggcgatacc gccgtgtact actgcgccaa gggctccaag    360

caccggctga gagactacgc cctgtacgac gatgacggcg ccctgaactg ggccgtggat    420

gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020
```

```
tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

```
<210> SEQ ID NO 36
<211> LENGTH: 490
<212> TYPE: PRT
<213> ORGANISM: Artificial Sequence
<220> FEATURE:
<223> OTHER INFORMATION: Synthetic Construct

<400> SEQUENCE: 36

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Ser Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
```

-continued

```
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490


<210> SEQ ID NO 37
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 37

atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggctacac cctgaaaacc tacgacctgc actgggtgcg atccgtgcct     180

ggacagggac tgcagtggat gggctggatc tcccacgagg gcgacaagaa agtgatcgtg     240

gaacggttca aggccaaagt gaccatcgac tgggaccggt ctaccaacac cgcttacctg     300

cagctgtccg gcctgacctc tggcgatacc gccgtgtact actgcgccaa gggctccaag     360

caccggctga gagactacgc cctgtacgac gatgacggcg ccctgaactg ggccgtggat     420

gtggactacc tgtccaacct ggaattctgg ggccagggca ccgccgtgac agtgtctagc     480

gcttctacca agggcccctc cgtgttccct ctggcccctt ccagcaagtc tacctccggc     540

ggaacagccg ctctgggctg cctcgtgaag gactacttcc ccgagcctgt gaccgtgtcc     600

tggaactctg gcgctctgac atccggcgtg cacaccttcc ctgctgtgct gcagtcctcc     660

ggcctgtact ccctgtcctc cgtcgtgacc gtgccttcca gctctctggg cacccagacc     720

tacatctgca acgtgaacca caagccctcc aacaccaagg tggacaagaa ggtggaaccc     780

aagtcctgcg acaagaccca cacctgtccc ccttgtcctg cccctgagct gctgggaggc     840
```

```
cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

<210> SEQ ID NO 38
<211> LENGTH: 490
<212> TYPE: PRT
<213> ORGANISM: Artificial Sequence
<220> FEATURE:
<223> OTHER INFORMATION: Synthetic Construct

<400> SEQUENCE: 38

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Tyr Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255
```

```
Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 39
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 39

```
atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggcaacac ctttaaaacc tacgacctgc actgggtgcg atccgtgcct     180

ggacagggac tgcagtggat gggctggatc tcccacgagg gcgacaagaa agtgatcgtg     240

gaacggttca aggccaaagt gaccatcgac tgggaccggt ctaccaacac cgcttacctg     300

cagctgtccg gcctgacctc tggcgatacc gccgtgtact actgcgccaa gggctccaag     360

caccggctga gagactacgc cctgtacgac gatgacggcg ccctgaactg ggccgtggat     420

gtggactacc tgtccaacct ggaattctgg ggccagggca ccgccgtgac agtgtctagc     480

gcttctacca agggcccctc cgtgttccct ctggcccctt ccagcaagtc tacctccggc     540

ggaacagccg ctctgggctg cctcgtgaag gactacttcc ccgagcctgt gaccgtgtcc     600

tggaactctg gcgctctgac atccggcgtg cacaccttcc ctgctgtgct gcagtcctcc     660

ggcctgtact ccctgtcctc cgtcgtgacc gtgccttcca gctctctggg cacccagacc     720
```

```
tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

```
<210> SEQ ID NO 40
<211> LENGTH: 490
<212> TYPE: PRT
<213> ORGANISM: Artificial Sequence
<220> FEATURE:
<223> OTHER INFORMATION: Synthetic Construct

<400> SEQUENCE: 40

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Phe
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220
```

-continued

Leu Ser Ser Val Val Thr Val Pro Ser Ser Ser Leu Gly Thr Gln Thr
225 230 235 240

Tyr Ile Cys Asn Val Asn His Lys Pro Ser Asn Thr Lys Val Asp Lys
245 250 255

Lys Val Glu Pro Lys Ser Cys Asp Lys Thr His Thr Cys Pro Pro Cys
260 265 270

Pro Ala Pro Glu Leu Leu Gly Gly Pro Ser Val Phe Leu Phe Pro Pro
275 280 285

Lys Pro Lys Asp Thr Leu Met Ile Ser Arg Thr Pro Glu Val Thr Cys
290 295 300

Val Val Val Asp Val Ser His Glu Asp Pro Glu Val Lys Phe Asn Trp
305 310 315 320

Tyr Val Asp Gly Val Glu Val His Asn Ala Lys Thr Lys Pro Arg Glu
325 330 335

Glu Gln Tyr Asn Ser Thr Tyr Arg Val Val Ser Val Leu Thr Val Leu
340 345 350

His Gln Asp Trp Leu Asn Gly Lys Glu Tyr Lys Cys Lys Val Ser Asn
355 360 365

Lys Ala Leu Pro Ala Pro Ile Glu Lys Thr Ile Ser Lys Ala Lys Gly
370 375 380

Gln Pro Arg Glu Pro Gln Val Tyr Thr Leu Pro Pro Ser Arg Glu Glu
385 390 395 400

Met Thr Lys Asn Gln Val Ser Leu Thr Cys Leu Val Lys Gly Phe Tyr
405 410 415

Pro Ser Asp Ile Ala Val Glu Trp Glu Ser Asn Gly Gln Pro Glu Asn
420 425 430

Asn Tyr Lys Thr Thr Pro Pro Val Leu Asp Ser Asp Gly Ser Phe Phe
435 440 445

Leu Tyr Ser Lys Leu Thr Val Asp Lys Ser Arg Trp Gln Gln Gly Asn
450 455 460

Val Phe Ser Cys Ser Val Leu His Glu Ala Leu His Ser His Tyr Thr
465 470 475 480

Gln Lys Ser Leu Ser Leu Ser Pro Gly Lys
485 490

<210> SEQ ID NO 41
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 41
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggcaacac cctgaaaacc tacgacctgc actgggtgcg atccgtgcct 180
ggacagggac tggaatggat gggctggatc tcccacgagg gcgacaagaa agtgatcgtg 240
gaacggttca aggccaaagt gaccatcgac tgggaccggt ctaccaacac cgcttacctg 300
cagctgtccg gcctgacctc tggcgatacc gccgtgtact actgcgccaa gggctccaag 360
caccggctga gagactacgc cctgtacgac gatgacggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540

```
ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

<210> SEQ ID NO 42
<211> LENGTH: 490
<212> TYPE: PRT
<213> ORGANISM: Artificial Sequence
<220> FEATURE:
<223> OTHER INFORMATION: Synthetic Construct

<400> SEQUENCE: 42

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Glu Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
```

```
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490


<210> SEQ ID NO 43
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 43

atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggcaacac cctgaaaacc tacgacctgc actgggtgcg atccgtgcct     180

ggacagggac tgcagtggat gggctggatc tcccacgagg gcgacaagaa agtgatcgtg     240

gaacggttca aggccaaagt gaccatcaca tgggaccggt ctaccaacac cgcttacctg     300

cagctgtccg gcctgacctc tggcgatacc gccgtgtact actgcgccaa gggctccaag     360

caccggctga gagactacgc cctgtacgac gatgacggcg ccctgaactg ggccgtggat     420
```

```
gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

```
<210> SEQ ID NO 44
<211> LENGTH: 490
<212> TYPE: PRT
<213> ORGANISM: Artificial Sequence
<220> FEATURE:
<223> OTHER INFORMATION: Synthetic Construct

<400> SEQUENCE: 44

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Thr Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175
```

```
Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 45
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 45

```
atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggcaacac cctgaaaacc tacgacctgc actgggtgcg atccgtgcct     180

ggacagggac tgcagtggat gggctggatc tcccacgagg gcgacaagaa agtgatcgtg     240
```

```
gaacggttca aggccaaagt gaccatcgac cgggaccggt ctaccaacac cgcttacctg    300
cagctgtccg gcctgacctc tggcgatacc gccgtgtact actgcgccaa gggctccaag    360
caccggctga gagactacgc cctgtacgac gatgacggcg ccctgaactg ggccgtggat    420
gtggactacc tgtccaacct ggaattctgg ggccagggca ccgccgtgac agtgtctagc    480
gcttctacca agggcccctc cgtgttccct ctggcccctt ccagcaagtc tacctccggc    540
ggaacagccg ctctgggctg cctcgtgaag gactacttcc ccgagcctgt gaccgtgtcc    600
tggaactctg gcgctctgac atccggcgtg cacaccttcc ctgctgtgct gcagtcctcc    660
ggcctgtact ccctgtcctc cgtcgtgacc gtgccttcca gctctctggg cacccagacc    720
tacatctgca acgtgaacca caagccctcc aacaccaagg tggacaagaa ggtggaaccc    780
aagtcctgcg acaagaccca cacctgtccc ccttgtcctg cccctgagct gctgggaggc    840
cctagcgtgt tcctgttccc tccaaagccc aaggacaccc tgatgatctc ccggaccccc    900
gaagtgacct gcgtggtggt ggatgtgtct cacgaggacc ctgaagtgaa gttcaattgg    960
tacgtggacg gcgtggaagt gcacaacgcc aagaccaagc ctagagagga acagtacaac   1020
tccacctacc gggtggtgtc cgtgctgacc gtgctgcacc aggattggct gaacggcaaa   1080
gagtacaagt gcaaggtgtc caacaaggct ctgcctgccc ccatcgaaaa gaccatctcc   1140
aaggccaagg gccagccccg ggaaccccag gtgtacacac tgccccctag ccgggaagag   1200
atgaccaaga accaggtgtc cctgacctgt ctcgtgaaag gcttctaccc ctccgatatc   1260
gccgtggaat gggagtccaa cggccagcct gagaacaact acaagaccac ccctcccgtg   1320
ctggactccg acggctcatt cttcctgtac agcaagctga cagtggacaa gtcccggtgg   1380
cagcagggca acgtgttctc ctgctccgtg ttgcacgagg ccctgcactc acactacacc   1440
cagaagtccc tgagcctgag ccccggcaaa tga                                1473
```

<210> SEQ ID NO 46
<211> LENGTH: 490
<212> TYPE: PRT
<213> ORGANISM: Artificial Sequence
<220> FEATURE:
<223> OTHER INFORMATION: Synthetic Construct

<400> SEQUENCE: 46

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Arg Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140
```

Ser Asn Leu Glu Phe Trp Gly Gln Gly Thr Ala Val Thr Val Ser Ser
145 150 155 160

Ala Ser Thr Lys Gly Pro Ser Val Phe Pro Leu Ala Pro Ser Ser Lys
165 170 175

Ser Thr Ser Gly Gly Thr Ala Ala Leu Gly Cys Leu Val Lys Asp Tyr
180 185 190

Phe Pro Glu Pro Val Thr Val Ser Trp Asn Ser Gly Ala Leu Thr Ser
195 200 205

Gly Val His Thr Phe Pro Ala Val Leu Gln Ser Ser Gly Leu Tyr Ser
210 215 220

Leu Ser Ser Val Val Thr Val Pro Ser Ser Ser Leu Gly Thr Gln Thr
225 230 235 240

Tyr Ile Cys Asn Val Asn His Lys Pro Ser Asn Thr Lys Val Asp Lys
245 250 255

Lys Val Glu Pro Lys Ser Cys Asp Lys Thr His Thr Cys Pro Pro Cys
260 265 270

Pro Ala Pro Glu Leu Leu Gly Gly Pro Ser Val Phe Leu Phe Pro Pro
275 280 285

Lys Pro Lys Asp Thr Leu Met Ile Ser Arg Thr Pro Glu Val Thr Cys
290 295 300

Val Val Val Asp Val Ser His Glu Asp Pro Glu Val Lys Phe Asn Trp
305 310 315 320

Tyr Val Asp Gly Val Glu Val His Asn Ala Lys Thr Lys Pro Arg Glu
325 330 335

Glu Gln Tyr Asn Ser Thr Tyr Arg Val Val Ser Val Leu Thr Val Leu
340 345 350

His Gln Asp Trp Leu Asn Gly Lys Glu Tyr Lys Cys Lys Val Ser Asn
355 360 365

Lys Ala Leu Pro Ala Pro Ile Glu Lys Thr Ile Ser Lys Ala Lys Gly
370 375 380

Gln Pro Arg Glu Pro Gln Val Tyr Thr Leu Pro Pro Ser Arg Glu Glu
385 390 395 400

Met Thr Lys Asn Gln Val Ser Leu Thr Cys Leu Val Lys Gly Phe Tyr
405 410 415

Pro Ser Asp Ile Ala Val Glu Trp Glu Ser Asn Gly Gln Pro Glu Asn
420 425 430

Asn Tyr Lys Thr Thr Pro Pro Val Leu Asp Ser Asp Gly Ser Phe Phe
435 440 445

Leu Tyr Ser Lys Leu Thr Val Asp Lys Ser Arg Trp Gln Gln Gly Asn
450 455 460

Val Phe Ser Cys Ser Val Leu His Glu Ala Leu His Ser His Tyr Thr
465 470 475 480

Gln Lys Ser Leu Ser Leu Ser Pro Gly Lys
485 490

<210> SEQ ID NO 47
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 47
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggcaacac cctgaaaacc tacgacctgc actgggtgcg atccgtgcct 180
ggacagggac tgcagtggat gggctggatc tcccacgagg gcgacaagaa agtgatcgtg 240
gaacggttca aggccaaagt gaccatcgac tgggaccggt ctaccaacac cgcttacctg 300
gagctgtccg gcctgacctc tggcgatacc gccgtgtact actgcgccaa gggctccaag 360
caccggctga gagactacgc cctgtacgac gatgacggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540
ggaacagccg ctctgggctg cctcgtgaag gactacttcc ccgagcctgt gaccgtgtcc 600
tggaactctg gcgctctgac atccggcgtg cacaccttcc ctgctgtgct gcagtcctcc 660
ggcctgtact ccctgtcctc cgtcgtgacc gtgccttcca gctctctggg cacccagacc 720
tacatctgca acgtgaacca caagccctcc aacaccaagg tggacaagaa ggtggaaccc 780
aagtcctgcg acaagaccca cacctgtccc ccttgtcctg cccctgagct gctgggaggc 840
cctagcgtgt tcctgttccc tccaaagccc aaggacaccc tgatgatctc ccggaccccc 900
gaagtgacct gcgtggtggt ggatgtgtct cacgaggacc ctgaagtgaa gttcaattgg 960
tacgtggacg gcgtggaagt gcacaacgcc aagaccaagc ctagagagga acagtacaac 1020
tccacctacc gggtggtgtc cgtgctgacc gtgctgcacc aggattggct gaacggcaaa 1080
gagtacaagt gcaaggtgtc caacaaggct ctgcctgccc ccatcgaaaa gaccatctcc 1140
aaggccaagg gccagccccg ggaaccccag gtgtacacac tgccccctag ccgggaagag 1200
atgaccaaga accaggtgtc cctgacctgt ctcgtgaaag gcttctaccc ctccgatatc 1260
gccgtggaat gggagtccaa cggccagcct gagaacaact acaagaccac ccctcccgtg 1320
ctggactccg acggctcatt cttcctgtac agcaagctga cagtggacaa gtcccggtgg 1380
cagcagggca acgtgttctc ctgctccgtg ttgcacgagg ccctgcactc acactacacc 1440
cagaagtccc tgagcctgag ccccggcaaa tga 1473

<210> SEQ ID NO 48
<211> LENGTH: 490
<212> TYPE: PRT
<213> ORGANISM: Artificial Sequence
<220> FEATURE:
<223> OTHER INFORMATION: Synthetic Construct

<400> SEQUENCE: 48

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Glu Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu

```
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 49
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 49

```
atgatgtcct ttgtctctct gctcctggtt ggcatcctat tccatgccac ccaggcccag     60
gtgcagctgg tgcagtccgg acccgaagtg cgaaagcctg gcacctccgt gaaggtgtcc    120
tgcaaggccc ctggcaacac cctgaaaacc tacgacctgc actgggtgcg atccgtgcct    180
ggacagggac tgcagtggat gggctggatc tcccacgagg gcgacaagaa agtgatcgtg    240
gaacggttca aggccaaagt gaccatcgac tgggaccggt ctaccaacac cgcttacctg    300
cagctgtccg gcctgagatc tggcgatacc gccgtgtact actgcgccaa gggctccaag    360
caccggctga gagactacgc cctgtacgac gatgacggcg ccctgaactg ggccgtggat    420
gtggactacc tgtccaacct ggaattctgg ggccagggca ccgccgtgac agtgtctagc    480
gcttctacca agggcccctc cgtgttccct ctggcccctt ccagcaagtc tacctccggc    540
ggaacagccg ctctgggctg cctcgtgaag gactacttcc ccgagcctgt gaccgtgtcc    600
tggaactctg gcgctctgac atccggcgtg cacaccttcc ctgctgtgct gcagtcctcc    660
ggcctgtact ccctgtcctc cgtcgtgacc gtgccttcca gctctctggg cacccagacc    720
tacatctgca acgtgaacca caagccctcc aacaccaagg tggacaagaa ggtggaaccc    780
aagtcctgcg acaagaccca cacctgtccc ccttgtcctg cccctgagct gctgggaggc    840
cctagcgtgt tcctgttccc tccaaagccc aaggacaccc tgatgatctc ccggaccccc    900
gaagtgacct gcgtggtggt ggatgtgtct cacgaggacc ctgaagtgaa gttcaattgg    960
tacgtggacg gcgtggaagt gcacaacgcc aagaccaagc ctagagagga acagtacaac   1020
tccacctacc gggtggtgtc cgtgctgacc gtgctgcacc aggattggct gaacggcaaa   1080
gagtacaagt gcaaggtgtc caacaaggct ctgcctgccc ccatcgaaaa gaccatctcc   1140
aaggccaagg gccagccccg ggaaccccag gtgtacacac tgccccctag ccgggaagag   1200
atgaccaaga accaggtgtc cctgacctgt ctcgtgaaag gcttctaccc ctccgatatc   1260
gccgtggaat gggagtccaa cggccagcct gagaacaact acaagaccac ccctcccgtg   1320
ctggactccg acggctcatt cttcctgtac agcaagctga cagtggacaa gtcccggtgg   1380
cagcagggca acgtgttctc ctgctccgtg ttgcacgagg ccctgcactc acactacacc   1440
cagaagtccc tgagcctgag ccccggcaaa tga                                1473
```

<210> SEQ ID NO 50
<211> LENGTH: 490
<212> TYPE: PRT
<213> ORGANISM: Artificial Sequence
<220> FEATURE:
<223> OTHER INFORMATION: Synthetic Construct

<400> SEQUENCE: 50

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95
```

```
Thr Ala Tyr Leu Gln Leu Ser Gly Leu Arg Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 51
<211> LENGTH: 1473

<212> TYPE: DNA
<213> ORGANISM: Artificial Sequence
<220> FEATURE:
<223> OTHER INFORMATION: Synthetic Construct

<400> SEQUENCE: 51
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggcaacac cctgaaaacc tacgacctgc actgggtgcg atccgtgcct 180
ggacagggac tgcagtggat gggctggatc tcccacgagg gcgacaagaa agtgatcgtg 240
gaacggttca aggccaaagt gaccatcgac tgggaccggt ctaccaacac cgcttacctg 300
cagctgtccg gcctgacctc tggcgatacc gccgtgtact actgcgccaa gggctccaag 360
caccggctga gagactacgc cctgtacgac gatgagggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540
ggaacagccg ctctgggctg cctcgtgaag gactacttcc ccgagcctgt gaccgtgtcc 600
tggaactctg gcgctctgac atccggcgtg cacaccttcc ctgctgtgct gcagtcctcc 660
ggcctgtact ccctgtcctc cgtcgtgacc gtgccttcca gctctctggg cacccagacc 720
tacatctgca acgtgaacca caagccctcc aacaccaagg tggacaagaa ggtggaaccc 780
aagtcctgcg acaagaccca cacctgtccc ccttgtcctg cccctgagct gctgggaggc 840
cctagcgtgt tcctgttccc tccaaagccc aaggacaccc tgatgatctc ccggaccccc 900
gaagtgacct gcgtggtggt ggatgtgtct cacgaggacc ctgaagtgaa gttcaattgg 960
tacgtggacg gcgtggaagt gcacaacgcc aagaccaagc ctagagagga acagtacaac 1020
tccacctacc gggtggtgtc cgtgctgacc gtgctgcacc aggattggct gaacggcaaa 1080
gagtacaagt gcaaggtgtc caacaaggct ctgcctgccc ccatcgaaaa gaccatctcc 1140
aaggccaagg gccagccccg ggaaccccag gtgtacacac tgccccctag ccgggaagag 1200
atgaccaaga accaggtgtc cctgacctgt ctcgtgaaag gcttctaccc ctccgatatc 1260
gccgtggaat gggagtccaa cggccagcct gagaacaact acaagaccac ccctcccgtg 1320
ctggactccg acggctcatt cttcctgtac agcaagctga cagtggacaa gtcccggtgg 1380
cagcagggca acgtgttctc ctgctccgtg ttgcacgagg ccctgcactc acactacacc 1440
cagaagtccc tgagcctgag ccccggcaaa tga 1473

<210> SEQ ID NO 52
<211> LENGTH: 490
<212> TYPE: PRT
<213> ORGANISM: Artificial Sequence
<220> FEATURE:
<223> OTHER INFORMATION: Synthetic Construct

<400> SEQUENCE: 52

Met Met Ser Phe Val Ser Leu Leu Leu Val Gly Ile Leu Phe His Ala
1 5 10 15

Thr Gln Ala Gln Val Gln Leu Val Gln Ser Gly Pro Glu Val Arg Lys
20 25 30

Pro Gly Thr Ser Val Lys Val Ser Cys Lys Ala Pro Gly Asn Thr Leu
35 40 45

Lys Thr Tyr Asp Leu His Trp Val Arg Ser Val Pro Gly Gln Gly Leu
50 55 60

```
Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Glu Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
```

485 490

<210> SEQ ID NO 53
<211> LENGTH: 96
<212> TYPE: DNA
<213> ORGANISM: Artificial Sequence
<220> FEATURE:
<223> OTHER INFORMATION: Synthetic Construct

<400> SEQUENCE: 53
ggctccaagc accggctgag agactacgcc ctgtacgacg atgagggcgc cctgaactgg 60
gccgtggatg tggactacct gtccaacctg gaattc 96

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Ser Lys His Arg Leu Arg Asp Tyr Ala Leu Tyr Asp Asp Glu Gly
1 5 10 15

Ala Leu Asn Trp Ala Val Asp Val Asp Tyr Leu Ser Asn Leu Glu Phe
20 25 30

<210> SEQ ID NO 55
<211> LENGTH: 714
<212> TYPE: DNA
<213> ORGANISM: Artificial Sequence
<220> FEATURE:
<223> OTHER INFORMATION: Synthetic Construct

<400> SEQUENCE: 55
atgatgtcct ttgtctctct gctcctggtt ggcatcctat tccatgccac ccaggccgac 60
ttcgtgctga cccagtcccc tctgtccctg cccgtgaccc ctggcgagcc cgcctccatc 120
tcctgcaagt cctcccacag cctgatccac ggcgaccgga acaactacct ggcttggtac 180
gtgcagaagc ctggccagtc accccagctg ctgatctacc tggcctcctc cagagcctct 240
ggcgtgcccg atagattctc cggctccggc agcgacaagg acttcaccct gaagatctcc 300
cgggtggaag ccgaggacgt gggcgtctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 56
<211> LENGTH: 238
<212> TYPE: PRT
<213> ORGANISM: Artificial Sequence
<220> FEATURE:
<223> OTHER INFORMATION: Synthetic Construct

<400> SEQUENCE: 56

Met Met Ser Phe Val Ser Leu Leu Leu Val Gly Ile Leu Phe His Ala
1 5 10 15

```
Thr Gln Ala Asp Phe Val Leu Thr Gln Ser Pro Leu Ser Leu Pro Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Gln Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Val Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 57
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 57

```
atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggcaacac cctgaaaacc tacgacctgc actgggtgcg atccgtgcct     180

ggacagggac tgcagtggat gggctggatc tcccacgagg gcgacaagaa agtgatcgtg     240

gaacggttca aggccaaagt gaccatcgac tgggaccggt ctaccaacac cgcttacctg     300

cagctgtccg gcctgagatc tggcgatacc gccgtgtact actgcgccaa gggctccaag     360

caccggctga gagactacgc cctgtacgac gatgacggcg ccctgaactg ggccgtggat     420

gtggactacc tgtccaacct ggaattctgg ggccagggca ccgccgtgac agtgtctagc     480

gcttctacca agggcccctc cgtgttccct ctggcccctt ccagcaagtc tacctccggc     540

ggaacagccg ctctgggctg cctcgtgaag gactacttcc ccgagcctgt gaccgtgtcc     600

tggaactctg gcgctctgac atccggcgtg cacaccttcc ctgctgtgct gcagtcctcc     660

ggcctgtact ccctgtcctc cgtcgtgacc gtgccttcca gctctctggg cacccagacc     720

tacatctgca acgtgaacca caagccctcc aacaccaagg tggacaagaa ggtggaaccc     780

aagtcctgcg acaagaccca cacctgtccc ccttgtcctg cccctgagct gctgggaggc     840
```

```
cctagcgtgt tcctgttccc tccaaagccc aaggacaccc tgatgatctc ccggaccccc     900

gaagtgacct gcgtggtggt ggatgtgtct cacgaggacc ctgaagtgaa gttcaattgg     960

tacgtggacg gcgtggaagt gcacaacgcc aagaccaagc ctagagagga acagtacaac    1020

tccacctacc gggtggtgtc cgtgctgacc gtgctgcacc aggattggct gaacggcaaa    1080

gagtacaagt gcaaggtgtc caacaaggct ctgcctgccc ccatcgaaaa gaccatctcc    1140

aaggccaagg gccagccccg ggaaccccag gtgtacacac tgccccctag ccgggaagag    1200

atgaccaaga accaggtgtc cctgacctgt ctcgtgaaag gcttctaccc ctccgatatc    1260

gccgtggaat gggagtccaa cggccagcct gagaacaact acaagaccac ccctcccgtg    1320

ctggactccg acggctcatt cttcctgtac agcaagctga cagtggacaa gtcccggtgg    1380

cagcagggca acgtgttctc ctgctccgtg ttgcacgagg ccctgcactc acactacacc    1440

cagaagtccc tgagcctgag ccccggcaaa tga                                 1473
```

<210> SEQ ID NO 58
<211> LENGTH: 490
<212> TYPE: PRT
<213> ORGANISM: Artificial Sequence
<220> FEATURE:
<223> OTHER INFORMATION: Synthetic Construct

<400> SEQUENCE: 58

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Arg Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
```

```
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 59
<211> LENGTH: 714
<212> TYPE: DNA
<213> ORGANISM: Artificial Sequence
<220> FEATURE:
<223> OTHER INFORMATION: Synthetic Construct

<400> SEQUENCE: 59

```
atgatgtcct ttgtctctct gctcctggtt ggcatcctat tccatgccac ccaggccgac      60

atcgtgctga cccagtcccc tcactccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggactg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660
```

acccatcagg gcctgagctc gcccgtcaca aagagcttca acaggggaga gtgt 714

<210> SEQ ID NO 60
<211> LENGTH: 238
<212> TYPE: PRT
<213> ORGANISM: Artificial Sequence
<220> FEATURE:
<223> OTHER INFORMATION: Synthetic Construct

<400> SEQUENCE: 60

Met Met Ser Phe Val Ser Leu Leu Leu Val Gly Ile Leu Phe His Ala
1 5 10 15

Thr Gln Ala Asp Ile Val Leu Thr Gln Ser Pro His Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Thr Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 61
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 61
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggcct ctggctacac ctttaaaacc tacgacctgc actgggtgcg atccgtgcct 180
ggacagggac tgcagtggat gggctggatc tcccacgagg gcgacaagaa agtgatcgtg 240
gaacggttca aggccaaagt gaccatcgac tgggaccggt ctaccaacac cgcttacctg 300
cagctgtccg gcctgacctc tggcgatacc gccgtgtact actgcgccaa gggctccaag 360

```
caccggctga gagactacgc cctgtacgac gatgacggcg ccctgaactg ggccgtggat    420

gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

```
<210> SEQ ID NO 62
<211> LENGTH: 490
<212> TYPE: PRT
<213> ORGANISM: Artificial Sequence
<220> FEATURE:
<223> OTHER INFORMATION: Synthetic Construct

<400> SEQUENCE: 62

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Ser Gly Tyr Thr Phe
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
```

```
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 63
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 63

```
atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggccc ctggcaacac cctgaaaacc tacgacctgc actgggtgcg atccgtgcct     180

ggacagggac tgcagtggat gggctggatc tcccacgagg gcgacaagaa agtgatcgtg     240
```

```
gaacggttca aggccaaagt gaccatcaca cgggaccggt ctaccaacac cgcttacctg    300

cagctgtccg gcctgacctc tggcgatacc gccgtgtact actgcgccaa gggctccaag    360

caccggctga gagactacgc cctgtacgac gatgacggcg ccctgaactg ggccgtggat    420

gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

<210> SEQ ID NO 64
<211> LENGTH: 490
<212> TYPE: PRT
<213> ORGANISM: Artificial Sequence
<220> FEATURE:
<223> OTHER INFORMATION: Synthetic Construct

<400> SEQUENCE: 64

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Thr Arg Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140
```

```
Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 65
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 65
atgatgtcct ttgtctctct gctcctggtt ggcatcctat tccatgccac ccaggcccag     60

```
gtgcagctgg tgcagtccgg acccgaagtg cgaaagcctg gcacctccgt gaaggtgtcc    120

tgcaaggcct ctggctacac ctttaaaacc tacgacctgc actgggtgcg atccgtgcct    180

ggacagggac tgcagtggat gggctggatc tcccacgagg gcgacaagaa agtgatcgtg    240

gaacggttca aggccaaagt gaccatcaca cgggaccggt ctaccaacac cgcttacctg    300

cagctgtccg gcctgacctc tggcgatacc gccgtgtact actgcgccaa gggctccaag    360

caccggctga gagactacgc cctgtacgac gatgacggcg ccctgaactg ggccgtggat    420

gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                 1473
```

<210> SEQ ID NO 66
<211> LENGTH: 490
<212> TYPE: PRT
<213> ORGANISM: Artificial Sequence
<220> FEATURE:
<223> OTHER INFORMATION: Synthetic Construct

<400> SEQUENCE: 66

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Ser Gly Tyr Thr Phe
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Thr Arg Asp Arg Ser Thr Asn
                85                  90                  95

Thr Ala Tyr Leu Gln Leu Ser Gly Leu Thr Ser Gly Asp Thr Ala Val
            100                 105                 110
```

```
Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 67
<211> LENGTH: 714
<212> TYPE: DNA
<213> ORGANISM: Artificial Sequence
<220> FEATURE:
<223> OTHER INFORMATION: Synthetic Construct

<400> SEQUENCE: 67

```
atgatgtcct ttgtctctct gctcctggtt ggcatcctat tccatgccac ccaggccgac     60

ttcgtgctga cccagtcccc tctgtccctg tctgtgaccc ctggcgagtc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgacaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 68
<211> LENGTH: 238
<212> TYPE: PRT
<213> ORGANISM: Artificial Sequence
<220> FEATURE:
<223> OTHER INFORMATION: Synthetic Construct

<400> SEQUENCE: 68

```
Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

Leu Ser Ser Pro Val Thr Lys Ser Phe Asn Arg Gly Glu Cys
225 230 235

<210> SEQ ID NO 69
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 69
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggctacac cctgaaaacc tacgacctgc actgggtgcg atccgtgcct 180
ggacagggac tgcagtggat gggctggatc tcccacgagg gcgacaagaa agtgatcgtg 240
gaacggttca aggccaaagt gaccatcaca tgggaccggt ctaccaacac cgcttacctg 300
cagctgtccg gcctgacctc tggcgatacc gccgtgtact actgcgccaa gggctccaag 360
caccggctga gagactacgc cctgtacgac gatgacggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540
ggaacagccg ctctgggctg cctcgtgaag gactacttcc ccgagcctgt gaccgtgtcc 600
tggaactctg gcgctctgac atccggcgtg cacaccttcc ctgctgtgct gcagtcctcc 660
ggcctgtact ccctgtcctc cgtcgtgacc gtgccttcca gctctctggg cacccagacc 720
tacatctgca acgtgaacca caagccctcc aacaccaagg tggacaagaa ggtggaaccc 780
aagtcctgcg acaagaccca cacctgtccc ccttgtcctg cccctgagct gctgggaggc 840
cctagcgtgt tcctgttccc tccaaagccc aaggacaccc tgatgatctc ccggaccccc 900
gaagtgacct gcgtggtggt ggatgtgtct cacgaggacc ctgaagtgaa gttcaattgg 960
tacgtggacg gcgtggaagt gcacaacgcc aagaccaagc ctagagagga acagtacaac 1020
tccacctacc gggtggtgtc cgtgctgacc gtgctgcacc aggattggct gaacggcaaa 1080
gagtacaagt gcaaggtgtc caacaaggct ctgcctgccc ccatcgaaaa gaccatctcc 1140
aaggccaagg gccagccccg ggaaccccag gtgtacacac tgccccctag ccgggaagag 1200
atgaccaaga accaggtgtc cctgacctgt ctcgtgaaag gcttctaccc ctccgatatc 1260
gccgtggaat gggagtccaa cggccagcct gagaacaact acaagaccac ccctcccgtg 1320
ctggactccg acggctcatt cttcctgtac agcaagctga cagtggacaa gtcccggtgg 1380
cagcagggca acgtgttctc ctgctccgtg ttgcacgagg ccctgcactc acactacacc 1440
cagaagtccc tgagcctgag ccccggcaaa tga 1473

<210> SEQ ID NO 70
<211> LENGTH: 490
<212> TYPE: PRT
<213> ORGANISM: Artificial Sequence
<220> FEATURE:
<223> OTHER INFORMATION: Synthetic Construct

<400> SEQUENCE: 70

Met Met Ser Phe Val Ser Leu Leu Leu Val Gly Ile Leu Phe His Ala
1 5 10 15

Thr Gln Ala Gln Val Gln Leu Val Gln Ser Gly Pro Glu Val Arg Lys
20 25 30

-continued

```
Pro Gly Thr Ser Val Lys Val Ser Cys Lys Ala Pro Gly Tyr Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Thr Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
```

```
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490


<210> SEQ ID NO 71
<211> LENGTH: 714
<212> TYPE: DNA
<213> ORGANISM: Artificial Sequence
<220> FEATURE:
<223> OTHER INFORMATION: Synthetic Construct

<400> SEQUENCE: 71

atgatgtcct ttgtctctct gctcctggtt ggcatcctat tccatgccac ccaggccgac      60

ttcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 72
<211> LENGTH: 238
<212> TYPE: PRT
<213> ORGANISM: Artificial Sequence
<220> FEATURE:
<223> OTHER INFORMATION: Synthetic Construct

<400> SEQUENCE: 72

Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140
```

```
Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 73
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 73

atgatgtcct ttgtctctct gctcctggtt ggcatcctat tccatgccac ccaggcccag      60

gtgcagctgg tgcagtccgg acccgaagtg cgaaagcctg gcacctccgt gaaggtgtcc     120

tgcaaggcct ctggctacac ctttaaaacc tacgacctgc actgggtgcg atccgtgcct     180

ggacagggac tgcagtggat gggctggatc tcccacgagg gcgacaagaa agtgatcgtg     240

gaacggttca aggccaaagt gaccatcgac tgggaccggt ctaccaacac cgcttacctg     300

cagctgtccg gcctgacctc tggcgatacc gccgtgtact actgcgccaa gggctccaag     360

caccggctga gagactacgc cctgtacgac gatgacggcg ccctgaactg ggccgtggat     420

gtggactacc tgtccaacct ggaattctgg ggccagggca ccgccgtgac agtgtctagc     480

gcttctacca agggcccctc cgtgttccct ctggcccctt ccagcaagtc tacctccggc     540

ggaacagccg ctctgggctg cctcgtgaag gactacttcc ccgagcctgt gaccgtgtcc     600

tggaactctg gcgctctgac atccggcgtg cacaccttcc ctgctgtgct gcagtcctcc     660

ggcctgtact ccctgtcctc cgtcgtgacc gtgccttcca gctctctggg cacccagacc     720

tacatctgca acgtgaacca caagccctcc aacaccaagg tggacaagaa ggtggaaccc     780

aagtcctgcg acaagaccca cacctgtccc ccttgtcctg cccctgagct gctgggaggc     840

cctagcgtgt tcctgttccc tccaaagccc aaggacaccc tgatgatctc ccggaccccc     900

gaagtgacct gcgtggtggt ggatgtgtct cacgaggacc ctgaagtgaa gttcaattgg     960

tacgtggacg gcgtggaagt gcacaacgcc aagaccaagc ctagagagga acagtacaac    1020

tccacctacc gggtggtgtc cgtgctgacc gtgctgcacc aggattggct gaacggcaaa    1080

gagtacaagt gcaaggtgtc caacaaggct ctgcctgccc ccatcgaaaa gaccatctcc    1140

aaggccaagg gccagccccg ggaaccccag gtgtacacac tgccccctag ccgggaagag    1200

atgaccaaga accaggtgtc cctgacctgt ctcgtgaaag gcttctaccc ctccgatatc    1260

gccgtggaat gggagtccaa cggccagcct gagaacaact acaagaccac ccctcccgtg    1320

ctggactccg acggctcatt cttcctgtac agcaagctga cagtggacaa gtcccggtgg    1380

cagcagggca acgtgttctc ctgctccgtg ttgcacgagg ccctgcactc acactacacc    1440

cagaagtccc tgagcctgag ccccggcaaa tga                                 1473
```

<210> SEQ ID NO 74
<211> LENGTH: 490
<212> TYPE: PRT
<213> ORGANISM: Artificial Sequence
<220> FEATURE:
<223> OTHER INFORMATION: Synthetic Construct

<400> SEQUENCE: 74

Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Ser Gly Tyr Thr Phe
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly 370 375 380

Gln Pro Arg Glu Pro Gln Val Tyr Thr Leu Pro Pro Ser Arg Glu Glu
385 390 395 400

Met Thr Lys Asn Gln Val Ser Leu Thr Cys Leu Val Lys Gly Phe Tyr
405 410 415

Pro Ser Asp Ile Ala Val Glu Trp Glu Ser Asn Gly Gln Pro Glu Asn
420 425 430

Asn Tyr Lys Thr Thr Pro Pro Val Leu Asp Ser Asp Gly Ser Phe Phe
435 440 445

Leu Tyr Ser Lys Leu Thr Val Asp Lys Ser Arg Trp Gln Gln Gly Asn
450 455 460

Val Phe Ser Cys Ser Val Leu His Glu Ala Leu His Ser His Tyr Thr
465 470 475 480

Gln Lys Ser Leu Ser Leu Ser Pro Gly Lys
485 490

<210> SEQ ID NO 75
<211> LENGTH: 714
<212> TYPE: DNA
<213> ORGANISM: Artificial Sequence
<220> FEATURE:
<223> OTHER INFORMATION: Synthetic Construct

<400> SEQUENCE: 75
atgatgtcct ttgtctctct gctcctggtt ggcatcctat tccatgccac ccaggccgac 60
ttcgtgctga cccagtcccc tctgtccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacactg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 76
<211> LENGTH: 238
<212> TYPE: PRT
<213> ORGANISM: Artificial Sequence
<220> FEATURE:
<223> OTHER INFORMATION: Synthetic Construct

<400> SEQUENCE: 76

Met Met Ser Phe Val Ser Leu Leu Leu Val Gly Ile Leu Phe His Ala
1 5 10 15

Thr Gln Ala Asp Phe Val Leu Thr Gln Ser Pro Leu Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

```
Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Thr Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 77
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 77

atgatgtcct ttgtctctct gctcctggtt ggcatcctat tccatgccac ccaggcccag     60

gtgcagctgg tgcagtccgg acccgaagtg cgaaagcctg gcacctccgt gaaggtgtcc    120

tgcaaggcct ctggctacac cctgaaaacc tacgacctgc actgggtgcg atccgtgcct    180

ggacagggac tgcagtggat gggctggatc tcccacgagg gcgacaagaa agtgatcgtg    240

gaacggttca aggccaaagt gaccatcgac tgggaccggt ctaccaacac cgcttacctg    300

cagctgtccg gcctgacctc tggcgatacc gccgtgtact actgcgccaa gggctccaag    360

caccggctga gagactacgc cctgtacgac gatgacggcg ccctgaactg ggccgtggat    420

gtggactacc tgtccaacct ggaattctgg ggccagggca ccgccgtgac agtgtctagc    480

gcttctacca agggcccctc cgtgttccct ctggcccctt ccagcaagtc tacctccggc    540

ggaacagccg ctctgggctg cctcgtgaag gactacttcc ccgagcctgt gaccgtgtcc    600

tggaactctg gcgctctgac atccggcgtg cacaccttcc ctgctgtgct gcagtcctcc    660

ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080
```

```
gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

<210> SEQ ID NO 78
<211> LENGTH: 490
<212> TYPE: PRT
<213> ORGANISM: Artificial Sequence
<220> FEATURE:
<223> OTHER INFORMATION: Synthetic Construct

<400> SEQUENCE: 78

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Ser Gly Tyr Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
```

```
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490
```

<210> SEQ ID NO 79
<211> LENGTH: 714
<212> TYPE: DNA
<213> ORGANISM: Artificial Sequence
<220> FEATURE:
<223> OTHER INFORMATION: Synthetic Construct

<400> SEQUENCE: 79

```
atgatgtcct ttgtctctct gctcctggtt ggcatcctat tccatgccac ccaggccgac     60

atcgtgctga cccagtcccc tcactccctg tctgtgaccc ctggcgagtc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgacaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 80
<211> LENGTH: 238
<212> TYPE: PRT
<213> ORGANISM: Artificial Sequence
<220> FEATURE:
<223> OTHER INFORMATION: Synthetic Construct

<400> SEQUENCE: 80

Met Met Ser Phe Val Ser Leu Leu Leu Val Gly Ile Leu Phe His Ala
1               5                   10                  15

Thr Gln Ala Asp Ile Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 81
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 81
atgatgtcct ttgtctctct gctcctggtt ggcatcctat tccatgccac ccaggcccag 60
gtgcagctgg tgcagtccgg acccgaagtg cgaaagcctg gcacctccgt gaaggtgtcc 120
tgcaaggccc ctggcaacac cctgaaaacc tacgacctgc actgggtgcg atccgtgcct 180
ggacagggac tggaatggat gggctggatc tcccacgagg gcgacaagaa agtgatcgtg 240
gaacggttca aggccaaagt gaccatcgac cgggaccggt ctaccaacac cgcttacctg 300
cagctgtccg gcctgagatc tggcgatacc gccgtgtact actgcgccaa gggctccaag 360
caccggctga gagactacgc cctgtacgac gatgacggcg ccctgaactg ggccgtggat 420
gtggactacc tgtccaacct ggaattctgg ggccagggca ccgccgtgac agtgtctagc 480
gcttctacca agggcccctc cgtgttccct ctggcccctt ccagcaagtc tacctccggc 540
ggaacagccg ctctgggctg cctcgtgaag gactacttcc ccgagcctgt gaccgtgtcc 600
tggaactctg gcgctctgac atccggcgtg cacaccttcc ctgctgtgct gcagtcctcc 660

```
ggcctgtact ccctgtcctc cgtcgtgacc gtgccttcca gctctctggg cacccagacc    720

tacatctgca acgtgaacca caagccctcc aacaccaagg tggacaagaa ggtggaaccc    780

aagtcctgcg acaagaccca cacctgtccc ccttgtcctg cccctgagct gctgggaggc    840

cctagcgtgt tcctgttccc tccaaagccc aaggacaccc tgatgatctc ccggaccccc    900

gaagtgacct gcgtggtggt ggatgtgtct cacgaggacc ctgaagtgaa gttcaattgg    960

tacgtggacg gcgtggaagt gcacaacgcc aagaccaagc ctagagagga acagtacaac   1020

tccacctacc gggtggtgtc cgtgctgacc gtgctgcacc aggattggct gaacggcaaa   1080

gagtacaagt gcaaggtgtc caacaaggct ctgcctgccc ccatcgaaaa gaccatctcc   1140

aaggccaagg gccagccccg ggaaccccag gtgtacacac tgccccctag ccgggaagag   1200

atgaccaaga accaggtgtc cctgacctgt ctcgtgaaag gcttctaccc ctccgatatc   1260

gccgtggaat gggagtccaa cggccagcct gagaacaact acaagaccac ccctcccgtg   1320

ctggactccg acggctcatt cttcctgtac agcaagctga cagtggacaa gtcccggtgg   1380

cagcagggca acgtgttctc ctgctccgtg ttgcacgagg ccctgcactc acactacacc   1440

cagaagtccc tgagcctgag ccccggcaaa tga                                1473
```

<210> SEQ ID NO 82
<211> LENGTH: 490
<212> TYPE: PRT
<213> ORGANISM: Artificial Sequence
<220> FEATURE:
<223> OTHER INFORMATION: Synthetic Construct

<400> SEQUENCE: 82

```
Met Met Ser Phe Val Ser Leu Leu Leu Val Gly Ile Leu Phe His Ala
1               5                   10                  15

Thr Gln Ala Gln Val Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Glu Trp Met Gly Trp Ile Ser His Glu Gly Asp Lys Lys Val Ile Val
65                  70                  75                  80

Glu Arg Phe Lys Ala Lys Val Thr Ile Asp Arg Asp Arg Ser Thr Asn
                85                  90                  95

Thr Ala Tyr Leu Gln Leu Ser Gly Leu Arg Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
```

```
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Leu His Glu Ala Leu His Ser His Tyr Thr
465                 470                 475                 480

Gln Lys Ser Leu Ser Leu Ser Pro Gly Lys
                485                 490


<210> SEQ ID NO 83
<211> LENGTH: 714
<212> TYPE: DNA
<213> ORGANISM: Artificial Sequence
<220> FEATURE:
<223> OTHER INFORMATION: Synthetic Construct

<400> SEQUENCE: 83

atgatgtcct ttgtctctct gctcctggtt ggcatcctat tccatgccac ccaggccgac      60

atcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480
```

aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 84
<211> LENGTH: 238
<212> TYPE: PRT
<213> ORGANISM: Artificial Sequence
<220> FEATURE:
<223> OTHER INFORMATION: Synthetic Construct

<400> SEQUENCE: 84

Met Met Ser Phe Val Ser Leu Leu Leu Val Gly Ile Leu Phe His Ala
1 5 10 15

Thr Gln Ala Asp Ile Val Leu Thr Gln Ser Pro Leu Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Asp Lys Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 85
<211> LENGTH: 714
<212> TYPE: DNA
<213> ORGANISM: Artificial Sequence
<220> FEATURE:
<223> OTHER INFORMATION: Synthetic Construct

<400> SEQUENCE: 85
atgatgtcct ttgtctctct gctcctggtt ggcatcctat tccatgccac ccaggccgac 60
atcgtgctga cccagtcccc tcactccctg tctgtgaccc ctggcgagcc cgcctccatc 120
tcctgcaagt cctcccacag cctgatccac ggcgaccgga acaactacct ggcttggtac 180

```
gtgcagaagc ctggccggtc accccagctg ctgatctacc tggcctcctc cagagcctct    240

ggcgtgcccg atagattctc cggctccggc agcgacaagg acttcaccct gaagatctcc    300

cgggtggaaa ccgaggacgt gggcacctac tactgtatgc agggcagaga gtcccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

```
<210> SEQ ID NO 86
<211> LENGTH: 238
<212> TYPE: PRT
<213> ORGANISM: Artificial Sequence
<220> FEATURE:
<223> OTHER INFORMATION: Synthetic Construct

<400> SEQUENCE: 86

Met Met Ser Phe Val Ser Leu Leu Leu Val Gly Ile Leu Phe His Ala
1               5                   10                  15

Thr Gln Ala Asp Ile Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 87
<211> LENGTH: 714
<212> TYPE: DNA
<213> ORGANISM: Artificial Sequence
<220> FEATURE:
```

<223> OTHER INFORMATION: Synthetic Construct

<400> SEQUENCE: 87
atgatgtcct ttgtctctct gctcctggtt ggcatcctat tccatgccac ccaggccgac 60
atcgtgctga cccagtcccc tcactccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 88
<211> LENGTH: 238
<212> TYPE: PRT
<213> ORGANISM: Artificial Sequence
<220> FEATURE:
<223> OTHER INFORMATION: Synthetic Construct

<400> SEQUENCE: 88

Met Met Ser Phe Val Ser Leu Leu Leu Val Gly Ile Leu Phe His Ala
1 5 10 15

Thr Gln Ala Asp Ile Val Leu Thr Gln Ser Pro His Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 89
<211> LENGTH: 714
<212> TYPE: DNA
<213> ORGANISM: Artificial Sequence
<220> FEATURE:
<223> OTHER INFORMATION: Synthetic Construct

<400> SEQUENCE: 89
atgatgtcct ttgtctctct gctcctggtt ggcatcctat tccatgccac ccaggccgac 60
atcgtgctga cccagtcccc tcactccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacaagg acttcaccct gaagatctcc 300
cgggtggaag ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 90
<211> LENGTH: 238
<212> TYPE: PRT
<213> ORGANISM: Artificial Sequence
<220> FEATURE:
<223> OTHER INFORMATION: Synthetic Construct

<400> SEQUENCE: 90

Met Met Ser Phe Val Ser Leu Leu Leu Val Gly Ile Leu Phe His Ala
1 5 10 15

Thr Gln Ala Asp Ile Val Leu Thr Gln Ser Pro His Ser Leu Ser Val
20 25 30

Thr Pro Gly Glu Ser Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Asp Lys Asp Phe Thr
85 90 95

Leu Lys Ile Ser Arg Val Glu Ala Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn 165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 91
<211> LENGTH: 714
<212> TYPE: DNA
<213> ORGANISM: Artificial Sequence
<220> FEATURE:
<223> OTHER INFORMATION: Synthetic Construct

<400> SEQUENCE: 91
atgatgtcct ttgtctctct gctcctggtt ggcatcctat tccatgccac ccaggccgac 60
ttcgtgctga cccagtcccc tctgtccctg tctgtgaccc ctggcgagcc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 92
<211> LENGTH: 238
<212> TYPE: PRT
<213> ORGANISM: Artificial Sequence
<220> FEATURE:
<223> OTHER INFORMATION: Synthetic Construct

<400> SEQUENCE: 92

Met Met Ser Phe Val Ser Leu Leu Leu Val Gly Ile Leu Phe His Ala
1 5 10 15

Thr Gln Ala Asp Phe Val Leu Thr Gln Ser Pro Leu Ser Leu Ser Val
20 25 30

Thr Pro Gly Glu Pro Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Asp Lys Asp Phe Thr
85 90 95

Leu Lys Ile Ser Arg Val Glu Thr Glu Asp Val Gly Thr Tyr Tyr Cys
100 105 110

```
Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 93
<211> LENGTH: 714
<212> TYPE: DNA
<213> ORGANISM: Artificial Sequence
<220> FEATURE:
<223> OTHER INFORMATION: Synthetic Construct

<400> SEQUENCE: 93

atgatgtcct ttgtctctct gctcctggtt ggcatcctat tccatgccac ccaggccgac      60

ttcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 94
<211> LENGTH: 238
<212> TYPE: PRT
<213> ORGANISM: Artificial Sequence
<220> FEATURE:
<223> OTHER INFORMATION: Synthetic Construct

<400> SEQUENCE: 94

Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60
```

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Thr Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 95
<211> LENGTH: 714
<212> TYPE: DNA
<213> ORGANISM: Artificial Sequence
<220> FEATURE:
<223> OTHER INFORMATION: Synthetic Construct

<400> SEQUENCE: 95
atgatgtcct ttgtctctct gctcctggtt ggcatcctat tccatgccac ccaggccgac 60
ttcgtgctga cccagtcccc tctgtccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgacaagg acttcaccct gaagatctcc 300
cgggtggaag ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 96
<211> LENGTH: 238
<212> TYPE: PRT
<213> ORGANISM: Artificial Sequence
<220> FEATURE:
<223> OTHER INFORMATION: Synthetic Construct

<400> SEQUENCE: 96

Met Met Ser Phe Val Ser Leu Leu Leu Val Gly Ile Leu Phe His Ala

```
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 97
<211> LENGTH: 714
<212> TYPE: DNA
<213> ORGANISM: Artificial Sequence
<220> FEATURE:
<223> OTHER INFORMATION: Synthetic Construct

<400> SEQUENCE: 97

```
atgatgtcct ttgtctctct gctcctggtt ggcatcctat tccatgccac ccaggccgac     60

ttcgtgctga cccagtcccc tcactccctg tctgtgaccc ctggcgagcc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgggaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 98
<211> LENGTH: 238
<212> TYPE: PRT
<213> ORGANISM: Artificial Sequence
<220> FEATURE:
<223> OTHER INFORMATION: Synthetic Construct

<400> SEQUENCE: 98

```
Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 99
<211> LENGTH: 714
<212> TYPE: DNA
<213> ORGANISM: Artificial Sequence
<220> FEATURE:
<223> OTHER INFORMATION: Synthetic Construct

<400> SEQUENCE: 99

```
atgatgtcct ttgtctctct gctcctggtt ggcatcctat tccatgccac ccaggccgac      60

ttcgtgctga cccagtcccc tcactccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480
```

```
aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714


<210> SEQ ID NO 100
<211> LENGTH: 238
<212> TYPE: PRT
<213> ORGANISM: Artificial Sequence
<220> FEATURE:
<223> OTHER INFORMATION: Synthetic Construct

<400> SEQUENCE: 100

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 101
<211> LENGTH: 714
<212> TYPE: DNA
<213> ORGANISM: Artificial Sequence
<220> FEATURE:
<223> OTHER INFORMATION: Synthetic Construct

<400> SEQUENCE: 101

atgatgtcct ttgtctctct gctcctggtt ggcatcctat tccatgccac ccaggccgac     60

ttcgtgctga cccagtcccc tcactccctg tctgtgaccc ctggcgagtc cgcctccatc    120

tcctgcaagt cctcccacag cctgatccac ggcgaccgga acaactacct ggcttggtac    180
```

```
gtgcagaagc ctggccggtc accccagctg ctgatctacc tggcctcctc cagagcctct    240

ggcgtgcccg atagattctc cggctccggc agcgggaagg acttcaccct gaagatctcc    300

cgggtggaag ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714

<210> SEQ ID NO 102
<211> LENGTH: 238
<212> TYPE: PRT
<213> ORGANISM: Artificial Sequence
<220> FEATURE:
<223> OTHER INFORMATION: Synthetic Construct

<400> SEQUENCE: 102

Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 103
<211> LENGTH: 714
<212> TYPE: DNA
<213> ORGANISM: Artificial Sequence
```

<220> FEATURE:
<223> OTHER INFORMATION: Synthetic Construct

<400> SEQUENCE: 103

```
atgatgtcct ttgtctctct gctcctggtt ggcatcctat tccatgccac ccaggccgac      60

atcgtgctga cccagtcccc tctgtccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714
```

<210> SEQ ID NO 104
<211> LENGTH: 238
<212> TYPE: PRT
<213> ORGANISM: Artificial Sequence
<220> FEATURE:
<223> OTHER INFORMATION: Synthetic Construct

<400> SEQUENCE: 104

```
Met Met Ser Phe Val Ser Leu Leu Leu Val Gly Ile Leu Phe His Ala
1               5                   10                  15

Thr Gln Ala Asp Ile Val Leu Thr Gln Ser Pro Leu Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
```

```
    210                 215                 220

Leu Ser Ser Pro Val Thr Lys Ser Phe Asn Arg Gly Glu Cys
225                 230                 235


<210> SEQ ID NO 105
<211> LENGTH: 714
<212> TYPE: DNA
<213> ORGANISM: Artificial Sequence
<220> FEATURE:
<223> OTHER INFORMATION: Synthetic Construct

<400> SEQUENCE: 105

atgatgtcct ttgtctctct gctcctggtt ggcatcctat tccatgccac ccaggccgac      60

atcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 106
<211> LENGTH: 238
<212> TYPE: PRT
<213> ORGANISM: Artificial Sequence
<220> FEATURE:
<223> OTHER INFORMATION: Synthetic Construct

<400> SEQUENCE: 106

Met Met Ser Phe Val Ser Leu Leu Leu Val Gly Ile Leu Phe His Ala
1               5                   10                  15

Thr Gln Ala Asp Ile Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 107
<211> LENGTH: 714
<212> TYPE: DNA
<213> ORGANISM: Artificial Sequence
<220> FEATURE:
<223> OTHER INFORMATION: Synthetic Construct

<400> SEQUENCE: 107

atgatgtcct ttgtctctct gctcctggtt ggcatcctat tccatgccac ccaggccgac      60

atcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 108
<211> LENGTH: 238
<212> TYPE: PRT
<213> ORGANISM: Artificial Sequence
<220> FEATURE:
<223> OTHER INFORMATION: Synthetic Construct

<400> SEQUENCE: 108

Met Met Ser Phe Val Ser Leu Leu Leu Val Gly Ile Leu Phe His Ala
1               5                   10                  15

Thr Gln Ala Asp Ile Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110
```

```
Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 109
<211> LENGTH: 714
<212> TYPE: DNA
<213> ORGANISM: Artificial Sequence
<220> FEATURE:
<223> OTHER INFORMATION: Synthetic Construct

<400> SEQUENCE: 109

```
atgatgtcct ttgtctctct gctcctggtt ggcatcctat tccatgccac ccaggccgac     60

atcgtgctga cccagtcccc tcactccctg tctgtgaccc ctggcgagcc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgggaagg acttcaccct gaagatctcc    300

cgggtggaaa ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 110
<211> LENGTH: 238
<212> TYPE: PRT
<213> ORGANISM: Artificial Sequence
<220> FEATURE:
<223> OTHER INFORMATION: Synthetic Construct

<400> SEQUENCE: 110

```
Met Met Ser Phe Val Ser Leu Leu Leu Val Gly Ile Leu Phe His Ala
1               5                   10                  15

Thr Gln Ala Asp Ile Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
```

```
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 111
<211> LENGTH: 714
<212> TYPE: DNA
<213> ORGANISM: Artificial Sequence
<220> FEATURE:
<223> OTHER INFORMATION: Synthetic Construct

<400> SEQUENCE: 111

atgatgtcct ttgtctctct gctcctggtt ggcatcctat tccatgccac ccaggccgac      60

atcgtgctga cccagtcccc tcactccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 112
<211> LENGTH: 238
<212> TYPE: PRT
<213> ORGANISM: Artificial Sequence
<220> FEATURE:
<223> OTHER INFORMATION: Synthetic Construct

<400> SEQUENCE: 112
```

```
Met Met Ser Phe Val Ser Leu Leu Leu Val Gly Ile Leu Phe His Ala
1               5                   10                  15

Thr Gln Ala Asp Ile Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 113
<211> LENGTH: 714
<212> TYPE: DNA
<213> ORGANISM: Artificial Sequence
<220> FEATURE:
<223> OTHER INFORMATION: Synthetic Construct

<400> SEQUENCE: 113

```
atgatgtcct ttgtctctct gctcctggtt ggcatcctat tccatgccac ccaggccgac      60

atcgtgctga cccagtcccc tcactccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714
```

<210> SEQ ID NO 114
<211> LENGTH: 238
<212> TYPE: PRT
<213> ORGANISM: Artificial Sequence
<220> FEATURE:
<223> OTHER INFORMATION: Synthetic Construct

<400> SEQUENCE: 114

```
Met Met Ser Phe Val Ser Leu Leu Leu Val Gly Ile Leu Phe His Ala
1               5                   10                  15

Thr Gln Ala Asp Ile Val Leu Thr Gln Ser Pro His Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 115
<211> LENGTH: 714
<212> TYPE: DNA
<213> ORGANISM: Artificial Sequence
<220> FEATURE:
<223> OTHER INFORMATION: Synthetic Construct

<400> SEQUENCE: 115

```
atgatgtcct ttgtctctct gctcctggtt ggcatcctat tccatgccac ccaggccgac      60

ttcgtgctga cccagtcccc tctgtccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaaa ccgaggacgt gggcacctac tactgtatgc agggcagaga gtccccctgg     360

acctttggcc agggcaccaa ggtggacatc aagcgtacgg tggctgcacc atctgtcttc     420
```

```
atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714


<210> SEQ ID NO 116
<211> LENGTH: 238
<212> TYPE: PRT
<213> ORGANISM: Artificial Sequence
<220> FEATURE:
<223> OTHER INFORMATION: Synthetic Construct

<400> SEQUENCE: 116

Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Thr Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 117
<211> LENGTH: 714
<212> TYPE: DNA
<213> ORGANISM: Artificial Sequence
<220> FEATURE:
<223> OTHER INFORMATION: Synthetic Construct

<400> SEQUENCE: 117

atgatgtcct ttgtctctct gctcctggtt ggcatcctat tccatgccac ccaggccgac     60

ttcgtgctga cccagtcccc tctgtccctg tctgtgaccc ctggcgagcc cgcctccatc    120
```

```
tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgacaagg acttcaccct gaagatctcc    300

cgggtggaag ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 118
<211> LENGTH: 238
<212> TYPE: PRT
<213> ORGANISM: Artificial Sequence
<220> FEATURE:
<223> OTHER INFORMATION: Synthetic Construct

<400> SEQUENCE: 118

```
Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 119
<211> LENGTH: 714
<212> TYPE: DNA

<213> ORGANISM: Artificial Sequence
<220> FEATURE:
<223> OTHER INFORMATION: Synthetic Construct

<400> SEQUENCE: 119
atgatgtcct ttgtctctct gctcctggtt ggcatcctat tccatgccac ccaggccgac 60
ttcgtgctga cccagtcccc tctgtccctg tctgtgaccc ctggcgagtc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaag ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 120
<211> LENGTH: 238
<212> TYPE: PRT
<213> ORGANISM: Artificial Sequence
<220> FEATURE:
<223> OTHER INFORMATION: Synthetic Construct

<400> SEQUENCE: 120

Met Met Ser Phe Val Ser Leu Leu Leu Val Gly Ile Leu Phe His Ala
1               5                   10                  15

Thr Gln Ala Asp Phe Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

```
Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 121
<211> LENGTH: 714
<212> TYPE: DNA
<213> ORGANISM: Artificial Sequence
<220> FEATURE:
<223> OTHER INFORMATION: Synthetic Construct

<400> SEQUENCE: 121

```
atgatgtcct ttgtctctct gctcctggtt ggcatcctat tccatgccac ccaggccgac      60

ttcgtgctga cccagtcccc tcactccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt          714
```

<210> SEQ ID NO 122
<211> LENGTH: 238
<212> TYPE: PRT
<213> ORGANISM: Artificial Sequence
<220> FEATURE:
<223> OTHER INFORMATION: Synthetic Construct

<400> SEQUENCE: 122

```
Met Met Ser Phe Val Ser Leu Leu Leu Val Gly Ile Leu Phe His Ala
1               5                   10                  15

Thr Gln Ala Asp Phe Val Leu Thr Gln Ser Pro His Ser Leu Ser Val
            20                  25                  30

Thr Pro Gly Glu Pro Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 123
<211> LENGTH: 714
<212> TYPE: DNA
<213> ORGANISM: Artificial Sequence
<220> FEATURE:
<223> OTHER INFORMATION: Synthetic Construct

<400> SEQUENCE: 123
atgatgtcct ttgtctctct gctcctggtt ggcatcctat tccatgccac ccaggccgac 60
atcgtgctga cccagtcccc tctgtccctg tctgtgaccc ctggcgagcc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaaa ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 124
<211> LENGTH: 238
<212> TYPE: PRT
<213> ORGANISM: Artificial Sequence
<220> FEATURE:
<223> OTHER INFORMATION: Synthetic Construct

<400> SEQUENCE: 124

Met Met Ser Phe Val Ser Leu Leu Leu Val Gly Ile Leu Phe His Ala
1 5 10 15

Thr Gln Ala Asp Ile Val Leu Thr Gln Ser Pro Leu Ser Leu Ser Val
20 25 30

Thr Pro Gly Glu Pro Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Thr Glu Asp Val Gly Thr Tyr Tyr Cys

```
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 125
<211> LENGTH: 714
<212> TYPE: DNA
<213> ORGANISM: Artificial Sequence
<220> FEATURE:
<223> OTHER INFORMATION: Synthetic Construct

<400> SEQUENCE: 125

atgatgtcct ttgtctctct gctcctggtt ggcatcctat tccatgccac ccaggccgac      60

atcgtgctga cccagtcccc tctgtccctg tctgtgaccc ctggcgagcc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgacaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 126
<211> LENGTH: 238
<212> TYPE: PRT
<213> ORGANISM: Artificial Sequence
<220> FEATURE:
<223> OTHER INFORMATION: Synthetic Construct

<400> SEQUENCE: 126

Met Met Ser Phe Val Ser Leu Leu Leu Val Gly Ile Leu Phe His Ala
1               5                   10                  15

Thr Gln Ala Asp Ile Val Leu Thr Gln Ser Pro Leu Ser Leu Ser Val
            20                  25                  30

Thr Pro Gly Glu Pro Ala Ser Ile Ser Cys Lys Ser Ser His Ser Leu
        35                  40                  45
```

-continued

```
Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Asp Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 127
<211> LENGTH: 714
<212> TYPE: DNA
<213> ORGANISM: Artificial Sequence
<220> FEATURE:
<223> OTHER INFORMATION: Synthetic Construct

<400> SEQUENCE: 127

```
atgatgtcct ttgtctctct gctcctggtt ggcatcctat tccatgccac ccaggccgac      60

atcgtgctga cccagtcccc tctgtccctg tctgtgaccc ctggcgagtc cgcctccatc     120

tcctgcaagt cctcccacag cctgatccac ggcgaccgga acaactacct ggcttggtac     180

gtgcagaagc ctggccggtc accccagctg ctgatctacc tggcctcctc cagagcctct     240

ggcgtgcccg atagattctc cggctccggc agcgggaagg acttcaccct gaagatctcc     300

cgggtggaag ccgaggacgt gggcacctac tactgtatgc agggcagaga gtccccctgg     360

acctttggcc agggcaccaa ggtggacatc aagcgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714
```

<210> SEQ ID NO 128
<211> LENGTH: 238
<212> TYPE: PRT
<213> ORGANISM: Artificial Sequence
<220> FEATURE:
<223> OTHER INFORMATION: Synthetic Construct

<400> SEQUENCE: 128

```
Met Met Ser Phe Val Ser Leu Leu Leu Val Gly Ile Leu Phe His Ala
1               5                   10                  15

Thr Gln Ala Asp Ile Val Leu Thr Gln Ser Pro Leu Ser Leu Ser Val
            20                  25                  30

Thr Pro Gly Glu Ser Ala Ser Ile Ser Cys Lys Ser Ser His Ser Leu
        35                  40                  45

Ile His Gly Asp Arg Asn Asn Tyr Leu Ala Trp Tyr Val Gln Lys Pro
    50                  55                  60

Gly Arg Ser Pro Gln Leu Leu Ile Tyr Leu Ala Ser Ser Arg Ala Ser
65                  70                  75                  80

Gly Val Pro Asp Arg Phe Ser Gly Ser Gly Ser Gly Lys Asp Phe Thr
                85                  90                  95

Leu Lys Ile Ser Arg Val Glu Ala Glu Asp Val Gly Thr Tyr Tyr Cys
            100                 105                 110

Met Gln Gly Arg Glu Ser Pro Trp Thr Phe Gly Gln Gly Thr Lys Val
        115                 120                 125

Asp Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 129
<211> LENGTH: 714
<212> TYPE: DNA
<213> ORGANISM: Artificial Sequence
<220> FEATURE:
<223> OTHER INFORMATION: Synthetic Construct

<400> SEQUENCE: 129

```
atgatgtcct ttgtctctct gctcctggtt ggcatcctat tccatgccac ccaggccgac     60

atcgtgctga cccagtcccc tcactccctg tctgtgaccc ctggcgagcc cgcctccatc    120

tcctgcaagt cctcccacag cctgatccac ggcgaccgga acaactacct ggcttggtac    180

gtgcagaagc ctggccggtc accccagctg ctgatctacc tggcctcctc cagagcctct    240

ggcgtgcccg atagattctc cggctccggc agcgggaagg acttcaccct gaagatctcc    300

cgggtggaag ccgaggacgt gggcacctac tactgtatgc agggcagaga gtccccctgg    360

acctttggcc agggcaccaa ggtggacatc aagcgtacgg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 130
<211> LENGTH: 238
<212> TYPE: PRT
<213> ORGANISM: Artificial Sequence
<220> FEATURE:
<223> OTHER INFORMATION: Synthetic Construct

<400> SEQUENCE: 130

Met Met Ser Phe Val Ser Leu Leu Leu Val Gly Ile Leu Phe His Ala
1 5 10 15

Thr Gln Ala Asp Ile Val Leu Thr Gln Ser Pro His Ser Leu Ser Val
20 25 30

Thr Pro Gly Glu Pro Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Ala Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 131
<211> LENGTH: 714
<212> TYPE: DNA
<213> ORGANISM: Artificial Sequence
<220> FEATURE:
<223> OTHER INFORMATION: Synthetic Construct

<400> SEQUENCE: 131
atgatgtcct ttgtctctct gctcctggtt ggcatcctat tccatgccac ccaggccgac 60
ttcgtgctga cccagtcccc tctgtccctg tctgtgaccc ctggcgagcc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaag ccgaggacgt gggcacctac tactgtatgc agggcagaga gtcccccctgg 360 acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 132
<211> LENGTH: 238
<212> TYPE: PRT
<213> ORGANISM: Artificial Sequence
<220> FEATURE:
<223> OTHER INFORMATION: Synthetic Construct

<400> SEQUENCE: 132

Met Met Ser Phe Val Ser Leu Leu Leu Val Gly Ile Leu Phe His Ala
1 5 10 15

Thr Gln Ala Asp Phe Val Leu Thr Gln Ser Pro Leu Ser Leu Ser Val
20 25 30

Thr Pro Gly Glu Pro Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Ala Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 133
<211> LENGTH: 714
<212> TYPE: DNA
<213> ORGANISM: Artificial Sequence
<220> FEATURE:
<223> OTHER INFORMATION: Synthetic Construct

<400> SEQUENCE: 133
atgatgtcct ttgtctctct gctcctggtt ggcatcctat tccatgccac ccaggccgac 60
atcgtgctga cccagtcccc tctgtccctg tctgtgaccc ctggcgagcc cgcctccatc 120
tcctgcaagt cctcccacag cctgatccac ggcgaccgga acaactacct ggcttggtac 180
gtgcagaagc ctggccggtc accccagctg ctgatctacc tggcctcctc cagagcctct 240
ggcgtgcccg atagattctc cggctccggc agcgggaagg acttcaccct gaagatctcc 300
cgggtggaag ccgaggacgt gggcacctac tactgtatgc agggcagaga gtccccctgg 360
acctttggcc agggcaccaa ggtggacatc aagcgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgt 714

<210> SEQ ID NO 134
<211> LENGTH: 238
<212> TYPE: PRT
<213> ORGANISM: Artificial Sequence
<220> FEATURE:
<223> OTHER INFORMATION: Synthetic Construct

<400> SEQUENCE: 134

Met Met Ser Phe Val Ser Leu Leu Leu Val Gly Ile Leu Phe His Ala
1 5 10 15

Thr Gln Ala Asp Ile Val Leu Thr Gln Ser Pro Leu Ser Leu Ser Val
20 25 30

Thr Pro Gly Glu Pro Ala Ser Ile Ser Cys Lys Ser Ser His Ser Leu
35 40 45

Ile His Gly Asp Arg Asn Asn Tyr Leu Ala Trp Tyr Val Gln Lys Pro
50 55 60

Gly Arg Ser Pro Gln Leu Leu Ile Tyr Leu Ala Ser Ser Arg Ala Ser
65 70 75 80

Gly Val Pro Asp Arg Phe Ser Gly Ser Gly Ser Gly Lys Asp Phe Thr
85 90 95

Leu Lys Ile Ser Arg Val Glu Ala Glu Asp Val Gly Thr Tyr Tyr Cys
100 105 110

Met Gln Gly Arg Glu Ser Pro Trp Thr Phe Gly Gln Gly Thr Lys Val
115 120 125

Asp Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys
225 230 235

<210> SEQ ID NO 135
<211> LENGTH: 219

<212> TYPE: PRT
<213> ORGANISM: Artificial Sequence
<220> FEATURE:
<223> OTHER INFORMATION: Synthetic Construct

<400> SEQUENCE: 135

Asp Phe Val Leu Thr Gln Ser Pro His Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 136
<211> LENGTH: 471
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Asp Trp Asp Arg Ser Thr Asn Thr Ala Tyr
65 70 75 80

Leu Gln Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

```
Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 137
<211> LENGTH: 103
<212> TYPE: PRT
<213> ORGANISM: Artificial Sequence
<220> FEATURE:
<223> OTHER INFORMATION: Synthetic Construct

<400> SEQUENCE: 137

```
Gln Pro Arg Glu Pro Gln Val Tyr Thr Leu Pro Pro Ser Arg Glu Glu
1               5                   10                  15

Met Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser
            100
```

<210> SEQ ID NO 138
<211> LENGTH: 103
<212> TYPE: PRT
<213> ORGANISM: Artificial Sequence
<220> FEATURE:
<223> OTHER INFORMATION: Synthetic Construct

<400> SEQUENCE: 138

```
Gln Pro Arg Glu Pro Gln Val Tyr Thr Leu Pro Pro Ser Arg Glu Glu
1               5                   10                  15

Met Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Gln Gln Gly Asn
65                  70                  75                  80

Val Phe Ser Cys Ser Val Leu His Glu Ala Leu His Ser His Tyr Thr
                85                  90                  95

Gln Lys Ser Leu Ser Leu Ser
            100
```

<210> SEQ ID NO 139
<211> LENGTH: 105
<212> TYPE: PRT
<213> ORGANISM: Artificial Sequence
<220> FEATURE:
<223> OTHER INFORMATION: Synthetic Construct

<400> SEQUENCE: 139

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
```

```
                85                  90                  95

Glu Lys Thr Ile Ser Lys Ala Lys Gly
            100                 105


<210> SEQ ID NO 140
<211> LENGTH: 208
<212> TYPE: PRT
<213> ORGANISM: Artificial Sequence
<220> FEATURE:
<223> OTHER INFORMATION: Synthetic Construct

<400> SEQUENCE: 140

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205


<210> SEQ ID NO 141
<211> LENGTH: 208
<212> TYPE: PRT
<213> ORGANISM: Artificial Sequence
<220> FEATURE:
<223> OTHER INFORMATION: Synthetic Construct

<400> SEQUENCE: 141

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Leu
            180                 185                 190

His Glu Ala Leu His Ser His Tyr Thr Gln Lys Ser Leu Ser Leu Ser
        195                 200                 205


<210> SEQ ID NO 142
<211> LENGTH: 98
<212> TYPE: PRT
<213> ORGANISM: Artificial Sequence
<220> FEATURE:
<223> OTHER INFORMATION: Synthetic Construct

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 143
<211> LENGTH: 21
<212> TYPE: PRT
<213> ORGANISM: Artificial Sequence
<220> FEATURE:
<223> OTHER INFORMATION: Synthetic Construct

<400> SEQUENCE: 143

Glu Pro Lys Ser Cys Asp Lys Thr His Thr Cys Pro Pro Cys Pro Ala
1               5                   10                  15

Pro Glu Leu Leu Gly
            20


<210> SEQ ID NO 144
<211> LENGTH: 219
<212> TYPE: PRT
<213> ORGANISM: Artificial Sequence
<220> FEATURE:
<223> OTHER INFORMATION: Synthetic Construct

<400> SEQUENCE: 144
```

```
Asp Ile Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 145
<211> LENGTH: 219
<212> TYPE: PRT
<213> ORGANISM: Artificial Sequence
<220> FEATURE:
<223> OTHER INFORMATION: Synthetic Construct

<400> SEQUENCE: 145

Asp Phe Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 146
<211> LENGTH: 219
<212> TYPE: PRT
<213> ORGANISM: Artificial Sequence
<220> FEATURE:
<223> OTHER INFORMATION: Synthetic Construct

<400> SEQUENCE: 146

Asp Phe Val Leu Thr Gln Ser Pro His Ser Leu Pro Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 147
<211> LENGTH: 219
<212> TYPE: PRT
<213> ORGANISM: Artificial Sequence
<220> FEATURE:
<223> OTHER INFORMATION: Synthetic Construct

<400> SEQUENCE: 147

Asp Phe Val Leu Thr Gln Ser Pro His Ser Leu Ser Val Thr Pro Gly

```
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 148
<211> LENGTH: 219
<212> TYPE: PRT
<213> ORGANISM: Artificial Sequence
<220> FEATURE:
<223> OTHER INFORMATION: Synthetic Construct

<400> SEQUENCE: 148

Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Gln Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 149
<211> LENGTH: 219
<212> TYPE: PRT
<213> ORGANISM: Artificial Sequence
<220> FEATURE:
<223> OTHER INFORMATION: Synthetic Construct

<400> SEQUENCE: 149

Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 150
<211> LENGTH: 219
<212> TYPE: PRT
<213> ORGANISM: Artificial Sequence
<220> FEATURE:
<223> OTHER INFORMATION: Synthetic Construct

<400> SEQUENCE: 150

Asp Phe Val Leu Thr Gln Ser Pro His Ser Leu Ser Val Thr Pro Gly
1               5                   10                  15
```

```
Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 151
<211> LENGTH: 219
<212> TYPE: PRT
<213> ORGANISM: Artificial Sequence
<220> FEATURE:
<223> OTHER INFORMATION: Synthetic Construct

<400> SEQUENCE: 151

```
Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 152
<211> LENGTH: 219
<212> TYPE: PRT
<213> ORGANISM: Artificial Sequence
<220> FEATURE:
<223> OTHER INFORMATION: Synthetic Construct

<400> SEQUENCE: 152

Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Val Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 153
<211> LENGTH: 471
<212> TYPE: PRT
<213> ORGANISM: Artificial Sequence
<220> FEATURE:
<223> OTHER INFORMATION: Synthetic Construct

<400> SEQUENCE: 153

Gln Val Gln Leu Val Gln Ser Gly Pro Glu Val Arg Lys Pro Gly Thr
1               5                   10                  15

Ser Val Lys Val Ser Cys Lys Ala Ser Gly Asn Thr Leu Lys Thr Tyr
            20                  25                  30
```

```
Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 154
<211> LENGTH: 471
<212> TYPE: PRT
<213> ORGANISM: Artificial Sequence
<220> FEATURE:
<223> OTHER INFORMATION: Synthetic Construct

<400> SEQUENCE: 154

Gln Val Gln Leu Val Gln Ser Gly Pro Glu Val Arg Lys Pro Gly Thr
1               5                   10                  15

Ser Val Lys Val Ser Cys Lys Ala Pro Gly Tyr Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 155
<211> LENGTH: 471
<212> TYPE: PRT
<213> ORGANISM: Artificial Sequence
<220> FEATURE:
<223> OTHER INFORMATION: Synthetic Construct

<400> SEQUENCE: 155

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Phe Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Asp Trp Asp Arg Ser Thr Asn Thr Ala Tyr
65 70 75 80

Leu Gln Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Asp Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

```
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 156
<211> LENGTH: 471
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Val Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Glu Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110
```

```
Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470
```

<210> SEQ ID NO 157
<211> LENGTH: 471
<212> TYPE: PRT
<213> ORGANISM: Artificial Sequence
<220> FEATURE:
<223> OTHER INFORMATION: Synthetic Construct

<400> SEQUENCE: 157

```
Gln Val Gln Leu Val Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Thr Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
```

```
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 158
<211> LENGTH: 471
<212> TYPE: PRT
<213> ORGANISM: Artificial Sequence
<220> FEATURE:
<223> OTHER INFORMATION: Synthetic Construct

<400> SEQUENCE: 158

Gln Val Gln Leu Val Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Arg Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
```

305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 159
<211> LENGTH: 471
<212> TYPE: PRT
<213> ORGANISM: Artificial Sequence
<220> FEATURE:
<223> OTHER INFORMATION: Synthetic Construct

<400> SEQUENCE: 159

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Asp Trp Asp Arg Ser Thr Asn Thr Ala Tyr
65 70 75 80

Leu Glu Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Asp Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser

```
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 160
<211> LENGTH: 471
<212> TYPE: PRT
<213> ORGANISM: Artificial Sequence
<220> FEATURE:
<223> OTHER INFORMATION: Synthetic Construct

<400> SEQUENCE: 160

Gln Val Gln Leu Val Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Arg Ser Gly Asp Thr Ala Val Tyr Tyr Cys
```

```
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470
```

<210> SEQ ID NO 161
<211> LENGTH: 471
<212> TYPE: PRT
<213> ORGANISM: Artificial Sequence
<220> FEATURE:
<223> OTHER INFORMATION: Synthetic Construct

<400> SEQUENCE: 161

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Asp Trp Asp Arg Ser Thr Asn Thr Ala Tyr
65 70 75 80

Leu Gln Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Glu Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 162
<211> LENGTH: 219
<212> TYPE: PRT
<213> ORGANISM: Artificial Sequence
<220> FEATURE:
<223> OTHER INFORMATION: Synthetic Construct

<400> SEQUENCE: 162

Asp Phe Val Leu Thr Gln Ser Pro Leu Ser Leu Pro Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Gln Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Ala Glu Asp Val Gly Val Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 163
<211> LENGTH: 471
<212> TYPE: PRT
<213> ORGANISM: Artificial Sequence
<220> FEATURE:
<223> OTHER INFORMATION: Synthetic Construct

<400> SEQUENCE: 163

Gln Val Gln Leu Val Gln Ser Gly Pro Glu Val Arg Lys Pro Gly Thr

```
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Arg Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430
```

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470

<210> SEQ ID NO 164
<211> LENGTH: 219
<212> TYPE: PRT
<213> ORGANISM: Artificial Sequence
<220> FEATURE:
<223> OTHER INFORMATION: Synthetic Construct

<400> SEQUENCE: 164

Asp Ile Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 165
<211> LENGTH: 471
<212> TYPE: PRT
<213> ORGANISM: Artificial Sequence
<220> FEATURE:
<223> OTHER INFORMATION: Synthetic Construct

<400> SEQUENCE: 165

Gln Val Gln Leu Val Gln Ser Gly Pro Glu Val Arg Lys Pro Gly Thr
1               5                   10                  15

Ser Val Lys Val Ser Cys Lys Ala Ser Gly Tyr Thr Phe Lys Thr Tyr
            20                  25                  30

Asp Leu His Trp Val Arg Ser Val Pro Gly Gln Gly Leu Gln Trp Met

```
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460
```

Leu Ser Leu Ser Pro Gly Lys
465 470

<210> SEQ ID NO 166
<211> LENGTH: 471
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Thr Arg Asp Arg Ser Thr Asn Thr Ala Tyr
65 70 75 80

Leu Gln Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Asp Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 167
<211> LENGTH: 471
<212> TYPE: PRT
<213> ORGANISM: Artificial Sequence
<220> FEATURE:
<223> OTHER INFORMATION: Synthetic Construct

<400> SEQUENCE: 167

Gln Val Gln Leu Val Gln Ser Gly Pro Glu Val Arg Lys Pro Gly Thr
1 5 10 15

Ser Val Lys Val Ser Cys Lys Ala Ser Gly Tyr Thr Phe Lys Thr Tyr
20 25 30

Asp Leu His Trp Val Arg Ser Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Thr Ile Thr Arg Asp Arg Ser Thr Asn Thr Ala Tyr
65 70 75 80

Leu Gln Leu Ser Gly Leu Thr Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Asp Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 168
<211> LENGTH: 219
<212> TYPE: PRT
<213> ORGANISM: Artificial Sequence
<220> FEATURE:
<223> OTHER INFORMATION: Synthetic Construct

<400> SEQUENCE: 168

Asp Phe Val Leu Thr Gln Ser Pro Leu Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 169
<211> LENGTH: 471
<212> TYPE: PRT
<213> ORGANISM: Artificial Sequence
<220> FEATURE:
<223> OTHER INFORMATION: Synthetic Construct

<400> SEQUENCE: 169

Gln Val Gln Leu Val Gln Ser Gly Pro Glu Val Arg Lys Pro Gly Thr
1               5                   10                  15

Ser Val Lys Val Ser Cys Lys Ala Pro Gly Tyr Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Thr Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

```
Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470
```

<210> SEQ ID NO 170
<211> LENGTH: 219
<212> TYPE: PRT
<213> ORGANISM: Artificial Sequence
<220> FEATURE:
<223> OTHER INFORMATION: Synthetic Construct

<400> SEQUENCE: 170

```
Asp Phe Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 171
<211> LENGTH: 471
<212> TYPE: PRT
<213> ORGANISM: Artificial Sequence
<220> FEATURE:
<223> OTHER INFORMATION: Synthetic Construct

<400> SEQUENCE: 171

Gln Val Gln Leu Val Gln Ser Gly Pro Glu Val Arg Lys Pro Gly Thr
1               5                   10                  15

Ser Val Lys Val Ser Cys Lys Ala Ser Gly Tyr Thr Phe Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 172
<211> LENGTH: 219
<212> TYPE: PRT
<213> ORGANISM: Artificial Sequence
<220> FEATURE:
<223> OTHER INFORMATION: Synthetic Construct

<400> SEQUENCE: 172

Asp Phe Val Leu Thr Gln Ser Pro Leu Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Thr Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 173
<211> LENGTH: 471
<212> TYPE: PRT
<213> ORGANISM: Artificial Sequence
<220> FEATURE:
<223> OTHER INFORMATION: Synthetic Construct

<400> SEQUENCE: 173

Gln Val Gln Leu Val Gln Ser Gly Pro Glu Val Arg Lys Pro Gly Thr
1               5                   10                  15

Ser Val Lys Val Ser Cys Lys Ala Ser Gly Tyr Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Leu His Glu Ala Leu His Ser His Tyr Thr Gln Lys Ser
450 455 460

Leu Ser Leu Ser Pro Gly Lys
465 470

<210> SEQ ID NO 174
<211> LENGTH: 219
<212> TYPE: PRT
<213> ORGANISM: Artificial Sequence
<220> FEATURE:
<223> OTHER INFORMATION: Synthetic Construct

<400> SEQUENCE: 174

Asp Ile Val Leu Thr Gln Ser Pro His Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 175
<211> LENGTH: 471
<212> TYPE: PRT
<213> ORGANISM: Artificial Sequence
<220> FEATURE:
<223> OTHER INFORMATION: Synthetic Construct

<400> SEQUENCE: 175

Gln Val Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr
20 25 30

Asp Leu His Trp Val Arg Ser Val Pro Gly Gln Gly Leu Glu Trp Met
35 40 45

Gly Trp Ile Ser His Glu Gly Asp Lys Lys Val Ile Val Glu Arg Phe
50 55 60

Lys Ala Lys Val Thr Ile Asp Arg Asp Arg Ser Thr Asn Thr Ala Tyr
65 70 75 80

Leu Gln Leu Ser Gly Leu Arg Ser Gly Asp Thr Ala Val Tyr Tyr Cys
85 90 95

Ala Lys Gly Ser Lys His Arg Leu Arg Asp Tyr Ala Leu Tyr Asp Asp
100 105 110

Asp Gly Ala Leu Asn Trp Ala Val Asp Val Asp Tyr Leu Ser Asn Leu
115 120 125

Glu Phe Trp Gly Gln Gly Thr Ala Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

```
Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 176
<211> LENGTH: 219
<212> TYPE: PRT
<213> ORGANISM: Artificial Sequence
<220> FEATURE:
<223> OTHER INFORMATION: Synthetic Construct

<400> SEQUENCE: 176

Asp Ile Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 177
<211> LENGTH: 219
<212> TYPE: PRT
<213> ORGANISM: Artificial Sequence
```

<220> FEATURE:
<223> OTHER INFORMATION: Synthetic Construct

<400> SEQUENCE: 177

Asp Ile Val Leu Thr Gln Ser Pro His Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 178
<211> LENGTH: 219
<212> TYPE: PRT
<213> ORGANISM: Artificial Sequence
<220> FEATURE:
<223> OTHER INFORMATION: Synthetic Construct

<400> SEQUENCE: 178

Asp Ile Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu

```
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 179
<211> LENGTH: 219
<212> TYPE: PRT
<213> ORGANISM: Artificial Sequence
<220> FEATURE:
<223> OTHER INFORMATION: Synthetic Construct

<400> SEQUENCE: 179

Asp Ile Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 180
<211> LENGTH: 219
<212> TYPE: PRT
<213> ORGANISM: Artificial Sequence
<220> FEATURE:
<223> OTHER INFORMATION: Synthetic Construct
```

<400> SEQUENCE: 180

Asp Phe Val Leu Thr Gln Ser Pro Leu Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 181
<211> LENGTH: 219
<212> TYPE: PRT
<213> ORGANISM: Artificial Sequence
<220> FEATURE:
<223> OTHER INFORMATION: Synthetic Construct

<400> SEQUENCE: 181

Asp Phe Val Leu Thr Gln Ser Pro Leu Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 182
<211> LENGTH: 219
<212> TYPE: PRT
<213> ORGANISM: Artificial Sequence
<220> FEATURE:
<223> OTHER INFORMATION: Synthetic Construct

<400> SEQUENCE: 182

Asp Phe Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 183
<211> LENGTH: 219
<212> TYPE: PRT
<213> ORGANISM: Artificial Sequence
<220> FEATURE:
<223> OTHER INFORMATION: Synthetic Construct

<400> SEQUENCE: 183
```

Asp Phe Val Leu Thr Gln Ser Pro His Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 184
<211> LENGTH: 219
<212> TYPE: PRT
<213> ORGANISM: Artificial Sequence
<220> FEATURE:
<223> OTHER INFORMATION: Synthetic Construct

<400> SEQUENCE: 184

Asp Phe Val Leu Thr Gln Ser Pro His Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 185
<211> LENGTH: 219
<212> TYPE: PRT
<213> ORGANISM: Artificial Sequence
<220> FEATURE:
<223> OTHER INFORMATION: Synthetic Construct

<400> SEQUENCE: 185

Asp Phe Val Leu Thr Gln Ser Pro His Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 186
<211> LENGTH: 219
<212> TYPE: PRT
<213> ORGANISM: Artificial Sequence
<220> FEATURE:
<223> OTHER INFORMATION: Synthetic Construct

<400> SEQUENCE: 186

Asp Ile Val Leu Thr Gln Ser Pro Leu Ser Leu Ser Val Thr Pro Gly

```
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 187
<211> LENGTH: 219
<212> TYPE: PRT
<213> ORGANISM: Artificial Sequence
<220> FEATURE:
<223> OTHER INFORMATION: Synthetic Construct

<400> SEQUENCE: 187

```
Asp Ile Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 188
<211> LENGTH: 219
<212> TYPE: PRT
<213> ORGANISM: Artificial Sequence
<220> FEATURE:
<223> OTHER INFORMATION: Synthetic Construct

<400> SEQUENCE: 188

Asp Ile Val Leu Thr Gln Ser Pro Leu Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 189
<211> LENGTH: 219
<212> TYPE: PRT
<213> ORGANISM: Artificial Sequence
<220> FEATURE:
<223> OTHER INFORMATION: Synthetic Construct

<400> SEQUENCE: 189

Asp Ile Val Leu Thr Gln Ser Pro His Ser Leu Ser Val Thr Pro Gly
1 5 10 15

```
Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 190
<211> LENGTH: 219
<212> TYPE: PRT
<213> ORGANISM: Artificial Sequence
<220> FEATURE:
<223> OTHER INFORMATION: Synthetic Construct

<400> SEQUENCE: 190

Asp Ile Val Leu Thr Gln Ser Pro His Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 191
<211> LENGTH: 219
<212> TYPE: PRT
<213> ORGANISM: Artificial Sequence
<220> FEATURE:
<223> OTHER INFORMATION: Synthetic Construct

<400> SEQUENCE: 191

Asp Ile Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 192
<211> LENGTH: 219
<212> TYPE: PRT
<213> ORGANISM: Artificial Sequence
<220> FEATURE:
<223> OTHER INFORMATION: Synthetic Construct

<400> SEQUENCE: 192

Asp Phe Val Leu Thr Gln Ser Pro Leu Ser Leu Ser Val Thr Pro Gly
1               5                   10                  15

Glu Pro Ala Ser Ile Ser Cys Lys Ser Ser His Ser Leu Ile His Gly
            20                  25                  30
```

```
Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 193
<211> LENGTH: 219
<212> TYPE: PRT
<213> ORGANISM: Artificial Sequence
<220> FEATURE:
<223> OTHER INFORMATION: Synthetic Construct

<400> SEQUENCE: 193

```
Asp Phe Val Leu Thr Gln Ser Pro Leu Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 194
<211> LENGTH: 219
<212> TYPE: PRT
<213> ORGANISM: Artificial Sequence
<220> FEATURE:
<223> OTHER INFORMATION: Synthetic Construct

<400> SEQUENCE: 194

Asp Phe Val Leu Thr Gln Ser Pro Leu Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 195
<211> LENGTH: 219
<212> TYPE: PRT
<213> ORGANISM: Artificial Sequence
<220> FEATURE:
<223> OTHER INFORMATION: Synthetic Construct

<400> SEQUENCE: 195

Asp Phe Val Leu Thr Gln Ser Pro His Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
```

35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 196
<211> LENGTH: 219
<212> TYPE: PRT
<213> ORGANISM: Artificial Sequence
<220> FEATURE:
<223> OTHER INFORMATION: Synthetic Construct

<400> SEQUENCE: 196

Asp Ile Val Leu Thr Gln Ser Pro Leu Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu 180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 197
<211> LENGTH: 219
<212> TYPE: PRT
<213> ORGANISM: Artificial Sequence
<220> FEATURE:
<223> OTHER INFORMATION: Synthetic Construct

<400> SEQUENCE: 197

Asp Ile Val Leu Thr Gln Ser Pro Leu Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Asp Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 198
<211> LENGTH: 219
<212> TYPE: PRT
<213> ORGANISM: Artificial Sequence
<220> FEATURE:
<223> OTHER INFORMATION: Synthetic Construct

<400> SEQUENCE: 198

Asp Ile Val Leu Thr Gln Ser Pro Leu Ser Leu Ser Val Thr Pro Gly
1 5 10 15

Glu Ser Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

-continued

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 199
<211> LENGTH: 219
<212> TYPE: PRT
<213> ORGANISM: Artificial Sequence
<220> FEATURE:
<223> OTHER INFORMATION: Synthetic Construct

<400> SEQUENCE: 199

Asp Ile Val Leu Thr Gln Ser Pro His Ser Leu Ser Val Thr Pro Gly
1 5 10 15

Glu Pro Ala Ser Ile Ser Cys Lys Ser Ser His Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Tyr Leu Ala Ser Ser Arg Ala Ser Gly Val Pro
50 55 60

Asp Arg Phe Ser Gly Ser Gly Ser Gly Lys Asp Phe Thr Leu Lys Ile
65 70 75 80

Ser Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 200
<211> LENGTH: 219
<212> TYPE: PRT
<213> ORGANISM: Artificial Sequence
<220> FEATURE:
<223> OTHER INFORMATION: Synthetic Construct

<400> SEQUENCE: 200

Asp Phe Val Leu Thr Gln Ser Pro Leu Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Gly Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 201
<211> LENGTH: 219
<212> TYPE: PRT
<213> ORGANISM: Artificial Sequence
<220> FEATURE:
<223> OTHER INFORMATION: Synthetic Construct

<400> SEQUENCE: 201

Asp Ile Val Leu Thr Gln Ser Pro Leu Ser Leu Ser Val Thr Pro Gly
1               5                   10                  15

Glu Pro Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60
```

```
Asp Arg Phe Ser Gly Ser Gly Ser Gly Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```